(12) United States Patent
Njar et al.

(10) Patent No.: US 9,156,792 B2
(45) Date of Patent: Oct. 13, 2015

(54) RETINAMIDE AND USES THEREOF

(75) Inventors: Vincent C. O. Njar, Lansdale, PA (US); Lalji K. Gediya, Secane, PA (US); Aakanksha Khandelwal, Silver Spring, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 12/991,822

(22) PCT Filed: May 7, 2009

(86) PCT No.: PCT/US2009/043109
§ 371 (c)(1),
(2), (4) Date: Nov. 9, 2010

(87) PCT Pub. No.: WO2010/036404
PCT Pub. Date: Apr. 1, 2010

(65) Prior Publication Data
US 2011/0059974 A1      Mar. 10, 2011

Related U.S. Application Data

(60) Provisional application No. 61/071,647, filed on May 9, 2008.

(51) Int. Cl.
| A61K 31/4164 | (2006.01) |
| A61K 31/53 | (2006.01) |
| A61K 31/4196 | (2006.01) |
| A61K 31/41 | (2006.01) |
| A61K 31/519 | (2006.01) |
| C07D 233/60 | (2006.01) |
| C07D 487/04 | (2006.01) |
| C07D 251/02 | (2006.01) |
| C07D 221/04 | (2006.01) |
| C07D 249/02 | (2006.01) |
| C07D 233/56 | (2006.01) |

(52) U.S. Cl.
CPC .............. *C07D 233/56* (2013.01); *A61K 31/41* (2013.01); *A61K 31/4164* (2013.01); *A61K 31/4196* (2013.01); *A61K 31/519* (2013.01); *A61K 31/53* (2013.01); *C07D 233/60* (2013.01); *C07D 249/02* (2013.01); *C07D 251/02* (2013.01); *C07D 487/04* (2013.01)

(58) Field of Classification Search
CPC .. C07D 487/04; C07D 233/60; C07D 251/02; C07D 221/04; C07D 249/02; A61K 31/4164; A61K 31/53; A61K 31/4196; A61K 31/41; A61K 31/519
See application file for complete search history.

(56) References Cited

U.S. PATENT DOCUMENTS

| 5,137,918 | A | 8/1992 | Weiershausen et al. |
| 7,244,751 | B2 | 7/2007 | Lu et al. |
| 7,265,143 | B2 | 9/2007 | Njar et al. |
| 2003/0162823 | A1* | 8/2003 | Njar et al. ..................... 514/396 |
| 2004/0132825 | A1 | 7/2004 | Bacopoulos et al. |
| 2005/0004007 | A1 | 1/2005 | Grant et al. |
| 2005/0187149 | A1 | 8/2005 | Naoe et al. |
| 2007/0060614 | A1 | 3/2007 | Bacopoulos et al. |
| 2007/0190022 | A1 | 8/2007 | Bacopoulos et al. |
| 2007/0197568 | A1 | 8/2007 | Bunn et al. |

FOREIGN PATENT DOCUMENTS

| DE | 4032187 A1 | 4/1992 |
| WO | 2010/036404 A3 | 4/2010 |

OTHER PUBLICATIONS

Azines definition from IUPAC Recommendations 1995, p. 1321.*
Patel, Jyoti B. et al., "Novel Retinoic Acid Metabolism Blocking Agents Endowed with Multiple Biological Activities are Efficient Growth Inhibitors of Human Breast and Prostate Cancer Cells in Vitro and a Human Breast Tumor Xenograft in Nude Mice," Journal of Medicinal Chemistry, Jul. 23, 2004, vol. 47, pp. 6716-6729.
Patel, JB et al., "Novel retinoic acid metabolism blocking agents have potent inhibitory activities on human breast cancer cells and tumour growth," British Journal of Cancer, Mar. 27, 2007, vol. 96, pp. 1204-1215.
Khandelwal, A. et al., "MS-275 synergistically enhances the growth inhibitory effects of RAMBA VN/66-I in hormone-insensitive PC-3 prostate cancer cells and tumours," British Journal of Cancer, Mar. 18, 2008, vol. 98, pp. 1234-1243.
International Search Report of PCT/US2009/043109, mailing date Apr. 19, 2010.
Written Opinion of PCT/US2009/043109, mailing date Apr. 19, 2010.
Belosay et al., "Histone deacetylation inhibitors synergize with retinoic acid metabolism blocking agent (VN/14-1) in letrozole resistant human breast cancer cells", The Endocrine Society's 88th Annual Meeting, Jun. 24-27, 2006, Boston, MA, USA.
Gediya et al, "Improved Synthesis of Histone Deacetylase Inhibitors (HDIs) (MS-275 and CI-994) and Inhibitory Effects of HDIs Alone or in Combination with RAMBAs or Retinoids on Growth of Human LNCaP Prostate Cancer Cells and Tumor Xenografts", Biorganic & Medicinal Chem 2008, vol. 16(6) pp. 3352-3360.

(Continued)

*Primary Examiner* — Valerie Rodriguez-Garcia
(74) *Attorney, Agent, or Firm* — Westerman, Hattori, Daniels & Adrian, LLP

(57) ABSTRACT

Retinoic acid metabolism blocking agents (RAMBAs). The RAMBAs may be used for treatment of cancer, including breast and prostate cancers. Methods for preparing novel retinamide RAMBAs. The methods include reacting RAMBAs with terminal polar carboxylic acid group with a variety of amines in the presence of suitable coupling reagents. The retinamide RAMBAs are potent inhibitors of the growth of prostate and breast cancer cells and may be useful for the treatment of these diseases in humans.

19 Claims, 1 Drawing Sheet

(56) References Cited

OTHER PUBLICATIONS

Gediya et al, "Design, Synthesis and Evaluation of Novel Mutual Prodrugs (Hybrid Drugs) of All-trans retinoic acid and Histone Deacetylase Inhibitors with Enhanced Anticancer Activities in Breast and Prostate Cancer Cells in Vitro", Journal of Medicinal Chemistry, vol. 51, 2008, 3895-3904.

Gediya et al., "Mutual prodrugs of all-trans retinoic acid and histone deacetylase inhibitors: Potent anticancer agents", Department of Pharmacology and Experimental Therapeutics, University of Maryland School of Medicine, Baltimore, MD 21201, USA.

Gediya et al., "A New Simple and High-Yield Synthesis of Suberoylanilide Hydroxamic Acid and Its Inhibitory Effect Alone or in Combination with Retinoids on Proliferation of Human Prostate Cancer Cells", Journal of Medicinal Chemistry, 2005, vol. 48, 5047-5051.

Khandelwal A et al., "HDAC inhibitor (MS-275) enhances the anticancer activity of retinoic acid metabolism blocking agent (VN/66-1) in human prostate cancer models", In: Proceedings of the American Association for Cancer Research Annual Meeting, Apr. 14-18, 2007, Los Angeles, CA, USA.].

Khandelwal et al., "Preclinical pharmacokinetics, absolute oral bioavailability and anti-cancer activity of VN/14-1 in human prostate cancer PC-3 cells" Presented at the AACR Centennial Conference: Translational Cancer Medicine, Nov. 4-8, 2007, Singapore.

Lim and Goldberg, "Drug Slows Prostate Tumor Growth by Keeping Vitamin A Active", American Association for Cancer Research, News Releases, Nov. 2007, 1-2.

Nagy et al., "Nuclear Receptor Repression Mediated by a Complex Containing SMRT, mSin3A, and Histone Deacetylase", Cell, vol. 89, May 2, 1997, pp. 373-380.

Njar, V et al. "Retinoic acid metabolism blocking agents (RAMBAs) for treatment of cancer and dermatological diseases", Bioorganic & Medicinal Chemistry (2006), vol. 14, pp. 4323-4340.

Qian et al., "In vivo imaging of retinoic acid receptor beta2 transcriptional activation by the histone deacetylase inhibitor MS-275 in retinoid-resistant prostate cancer cells", The Prostate, Jun. 15, 2005;64(1):20-8 (The Sidney Kimmel Comprehensive Cancer Center at Johns Hopkins).

Suzuki et al.; "Synthesis and Histone Deacetylase Inhibitory Activity of New Benzamide Derivatives", Journal of Medicinal Chemistry, 1999, vol. 42, No. 15, 3001-3003.

* cited by examiner

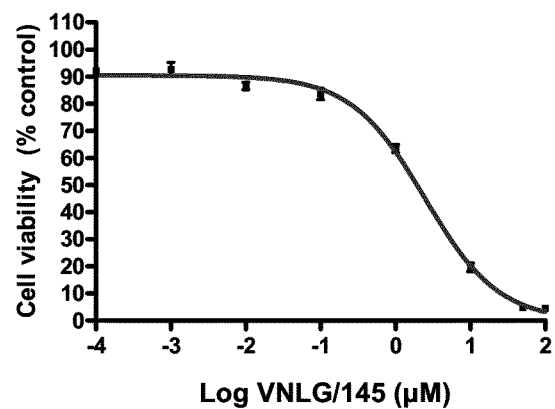

RETINAMIDE AND USES THEREOF

CROSS REFERENCE TO RELATED APPLICATIONS

This Application claims benefit to U.S. Provisional Application 61/071,647, filed May 9, 2008, which is herein incorporated by reference in its entirety.

STATEMENT REGARDING FEDERALLY SPONSORED RESEARCH OR DEVELOPMENT

This invention was made with government support under Grant Number CA117991 awarded by the National Institutes of Health and Grant Number W81XWH-04-1-0101 awarded by the Department of Defense. The U.S. government has certain rights in this invention.

BACKGROUND OF THE INVENTION

Cancer

Despite many years of research, there exists a compelling need to develop new and more effective therapeutic strategies for cancer. The use of many agents used in cancer treatment is limited because of their cytotoxic effects on normal tissues and cells. This is a particular concern for agents that kill cells by damaging DNA and/or inhibiting DNA replication.

Retinoids

Retinoids are a group of natural and synthetic analogues of vitamin A. All-trans-retinoic acid (ATRA), the biologically most active metabolite of vitamin A plays a major role in regulating cellular growth and differentiation.[i] Since retinoids are capable of inhibiting growth, inducing terminal differentiation and apoptosis in cultured cancer cell lines, there is a wide interest in their use in cancer therapy.[ii] The biological effects of retinoids result from modulation of gene expression, mediated through two complex types of nuclear receptors, retinoic acid receptors, and retinoid X receptors (RARs and RXRs).[iii] Each type includes 3 distinct subtypes ($\alpha$, $\beta$, and $\gamma$) encoded by distinct genes. Each RAR and RXR subtype is expressed in specific patterns in different tissues and is thought to have a specific profile of gene-regulating activity. The nuclear receptors function as dimers. RARs form heterodimers with RXRs. RXRs are more versatile, binding to RARs and other nuclear receptors, including thyroid hormone receptors and vitamin D receptors. Therefore, ATRA and other retinoids, through a variety of mechanisms, can modulate the expression of an extraordinarily large number of genes.[iv]

One of the most impressive effects of retinoids is on acute promyelocytic leukemia (APL). Treatment of APL patients with high doses of ATRA results in most of the cases in complete remission (Castaigne et al., 1990). Other research has been conducted on retinoid-based therapies for other cancers.[v]

Exogenous application of retinoids such as ATRA inhibits the growth and induces apoptosis in prostate cancer cell lines. Pasquali et al showed that the concentration of ATRA was 5-8 times lower in prostate carcinoma tissue compared with normal prostate and benign prostate hyperplasia.[vi] In vivo studies showed that ATRA inhibited induction and caused the disappearance of prostate tumors in animals.[vii] In spite of these encouraging results, the effects of ATRA therapy on human prostate cancer in the clinic have been disappointing.

One of the causes of the scarce therapeutic effects seems to be the rapid in vivo metabolism of ATRA into inactive metabolites.[viii] The inhibition of cytochrome P450 mediated ATRA metabolism by retinoic acid metabolism blocking agents (RAMBAs) is a promising approach in order to increase the levels of ATRA.[ix] Liarozole, the first RAMBA to undergo clinical investigations, was shown to increase ATRA levels in the tumor, resulting in anti-tumor activity.[x] Although, clinical development of this compound for prostate cancer therapy was discontinued for undisclosed reasons, it was recently approved in Europe and USA as an orphan drug for the treatment of congenital ichthyosis.[xi]

PCA tumors that arise after anti-hormonal therapy generally are less differentiated. Differentiation therapy remains a promising therapeutic approach in the treatment and chemoprevention of a variety of cancers, including PCA. Among the differentiation agents, retinoids, rexinoids, retinoid-related molecules (RRIVIs) and histone deacetylase inhibitors (HDACIs) have shown promising biological activities as single agents in several preclinical studies of both hematological and solid malignancies.[xii]

A goal of differentiation therapy is to induce malignant cells to pass the block to maturation by allowing them to progress to more differentiated cell types with less proliferative ability. Others have led the way in the discovery of agents that inhibit the enzyme histone deacetylase, thereby altering chromatin structure and changing gene expression patterns.[xiii] RAs exert their effects via a nuclear receptor complex that interacts with promoters of RA-responsive genes.[xiv]

Applicants have reported on a family of compounds that inhibit the P450 enzyme(s) responsible for the metabolism of all-trans retinoic acid (ATRA).[xv] These compounds, also referred to as retinoic acid metabolism blocking agents (RAMBAs), are able to enhance the antiproliferative effects of ATRA in breast and prostate cancer cells in vitro.[xvi] In addition, the RAMBAs were shown to induce differentiation and apoptosis in these cancer cell lines. Applicants' observed that the breast cancer cell lines were exquisitely more sensitive to the RAMBAs.[xvii]

By introduction of nucleophilic ligand at C-4 of ATRA or 13-CRA, and modification of the terminal carboxylic acid group, Applicants invented a series of potent RAMBAs some of which are by far the most potent retinoic acid metabolism inhibitors known.[xviii,xix] See U.S. Pat. No. 7,265,143, which is hereby incorporated by reference in its entirety.

Applicants also demonstrated that these RAMBAs inhibited the growth of several breast and prostate cancer cell lines and could exquisitely enhance the ATRA-mediated antiproliferative activity in vitro and in vivo.[xx,xxi,xxii] It was shown that VN/14-1 binds and activates the RAR$\alpha,\beta,\gamma$ receptors, albeit it is significantly less potent than ATRA. Furthermore, none of the RAMBAs showed significant binding to either cellular retinoic binding proteins (CRABP I or II).[xxiii] It has also been demonstrated that some RAMBAs inhibited the growth of established breast and prostate tumor xenografts and that their mechanisms of action may in part be due to induction of differentiation, apoptosis and cell cycle arrest.[xxiv,xxv,xxvi,xxvii]

Some of Applicants' proprietary RAMBAs appear to be the most potent ATRA metabolism inhibitors known.[xxviii] Furthermore, some of these proprietary RAMBAs also exhibit retinoidal and cell antiproliferative activities in a number of human cancer cell lines. These multiple biological activities have prompted Applicants to classify them as "atypical RAMBAs".

The anti-neoplastic activities of RAMBAs may be cell type dependent. Applicants have shown that some RAMBAs (e.g., VN/14-1) are more effective in breast cancer cell lines while others (e.g., VN/66-1) are more effective in prostate cancer cell lines.[xxix,xxx,xxxi,xxxii]

The apparent lack of sensitivity of the breast cancer cells (MDA-MB-231) and two prostate cancer cell lines (LNCaP and PC-3) to ATRA and some of Applicants' proprietary RAMBAs may be due to the differential expressions of various genes that are essential for retinoid activity.

There continues to be an urgent need to develop new therapeutic agents with defined targets to prevent and treat cancer, including prostate and breast cancer.

BRIEF SUMMARY OF THE INVENTION

Applicants' invention includes new RAMBAs that are potentially more potent than known RAMBAs.

One embodiment of Applicants' invention are novel RAMBAs without the phenolic hydroxyl group as shown in some of the RAMBAs of U.S. Pat. No. 7,265,143. Acylation presents a likely avenue for metabolic instability. 4-methoxyphenylretinamide has previously been identified as a major inactive metabolite of the closely related 4-hydroxyphenyl retinamide (4-HPR) in several animal and human studies.[xxxiii]

One embodiment of Applicants' invention includes replacing the phenol moiety with a more metabolically stable functionality, with a goal of modulating the physical properties of these analogs without affecting the enzyme and antiproliferative potencies already achieved by the RAMBAs of U.S. Pat. No. 7,265,143, for example, VN/66-1.

Applicants' invention also includes enantiomers of the new RAMBAs of the present application (structural formulae 2A, 3A, 3B, 4B, 4C and 5) and their use and enantiomers of certain RAMBAs of U.S. Pat. No. 7,265,143 and their use.

Anilineamide RAMBAs

The phenolic hydroxyl moiety may replaced with its classical isosteres, for example, halogens such as F and Cl, or non-classical bioisosteres, for example, $-CF_3$, $-CN$, and $-SH$.[xxxiv]

General Formulae 2A represents new anilineamide RAMBAs of the present invention.

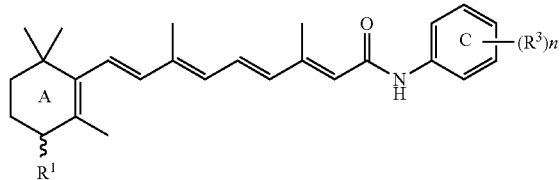

2A where $R^1$ is an azole group, a sulfur containing group, an oxygen containing group, a nitrogen containing group, a pyridyl group, an ethinyl group, a cyclopropyl-amine group, an ester group, a cyano group, a heteroaryl ring or an 1H-imidazole group, or $R^1$ forms, together with the C-4 carbon atom, an oxime, an oxirane or aziridine group;

each $R^3$ is independent and is selected from a halogen group, a cyano group, a thiol group, or an alkyl group substituted with at least one of a halogen group, a cyano group, and a thiol group; and n is from 0 to 5.

Non-limiting examples of such sulfur containing groups include thiirane, thiol and alkylthiol derivatives. Examples of such alkylthiol derivatives include $C_1$ to $C_{10}$ alkyl thiols.

Non-limiting examples of oxygen containing groups include $-OR_4$, where $R_4$ is hydrogen or an alkyl group (preferably a 1-10 carbon alkyl, more preferably methyl or ethyl), cyclopropylether or an oxygen containing group that forms, together with the 4-position carbon, an oxirane group.

Non-limiting examples of nitrogen containing groups include the formula $-NR_5R_6$, where $R_5$ and $R_6$ are independently selected from the group consisting of hydrogen and alkyl groups (preferably a 1-10 carbon alkyl, more preferably methyl or ethyl), or $R_5$ and $R_6$ may together form a ring. Preferably the ring formed by $R_5$ and $R_6$ is a imidazolyl ring or a triazole ring.

Azole substituent groups may be imidazoles and triazoles, including attachment through a nitrogen ring atom. The azole substituent groups may be 1H-imidazole-1-yl, 1H-1,2,4-triazol-1-yl and 4H-1,2,4-triazol-1-yl.

$R^1$ may be cyano, amino, azido, cyclopropylamino, or $R^1$ may be a nitrogen containing group that forms, together with the 4-position carbon, an aziridine group or an oxime group.

$R^1$ may also be a pyridyl group or an allylic azole group, preferably methyleneazolyl.

The definitions for $R^1$ of an ester includes substituent groups that contain an ester moiety, including substituent groups attached via an ester moiety.

Non-limiting examples of the alkyl group include linear and branched alkyl groups, including primary, secondary and tertiary alkyl groups, and substituted and unsubstituted alkyl groups.

The $R^3$ substituent groups may be F, $-CN$, $-SH$ and $-CF_3$.

An example of General Formula 2A is General Formula 2A'

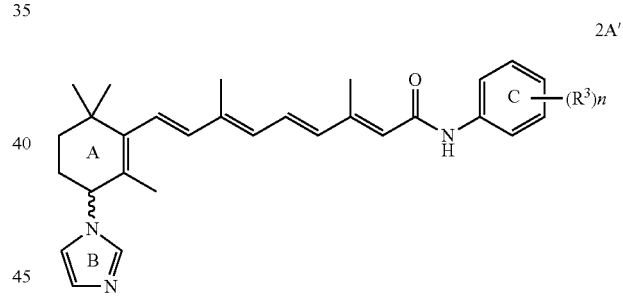

where $R^3$ and n are as defined for General Formula 2A.

Exemplary compounds of Formula 2A are Compounds VNLG/146, VNLG/153, and Compounds 4-33.

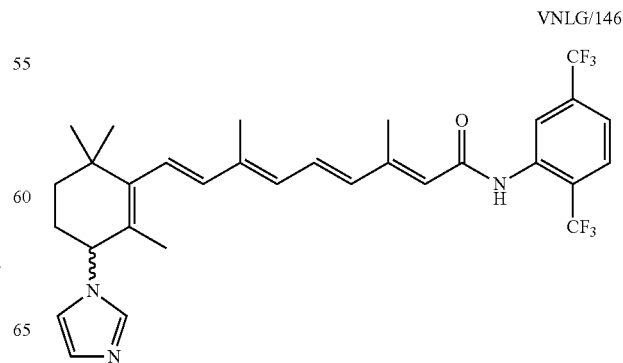

VNLG/146

VNLG/153
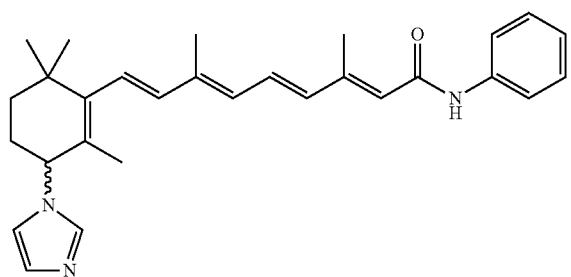
3
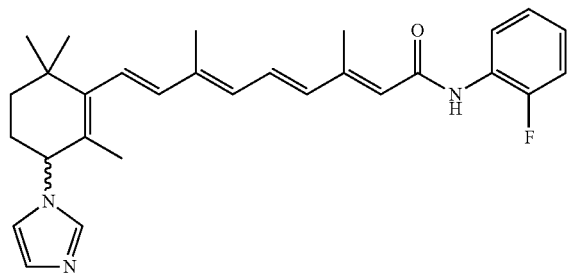
5
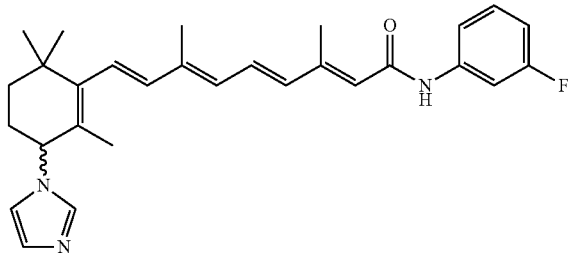
6
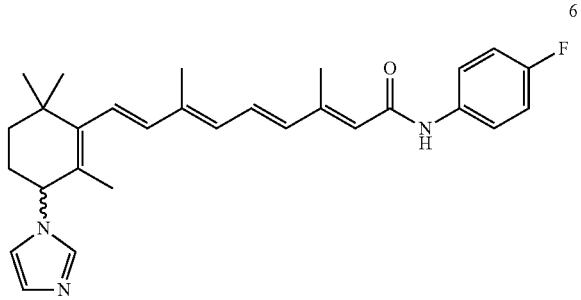
7
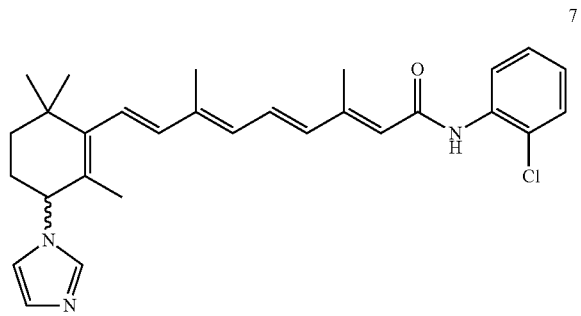
8
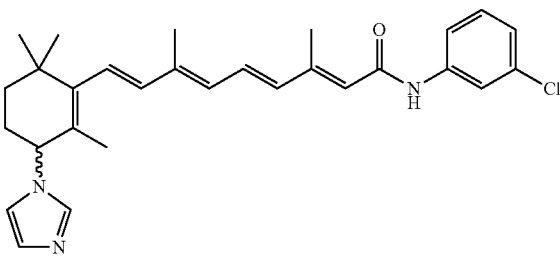
9
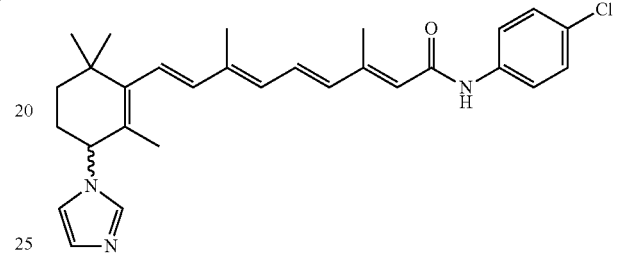
10
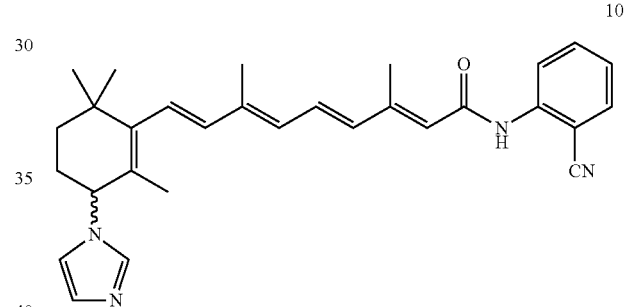
11
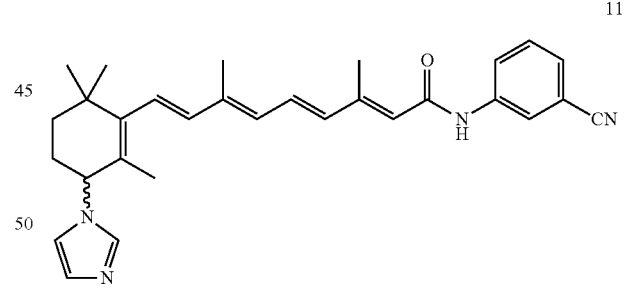
12
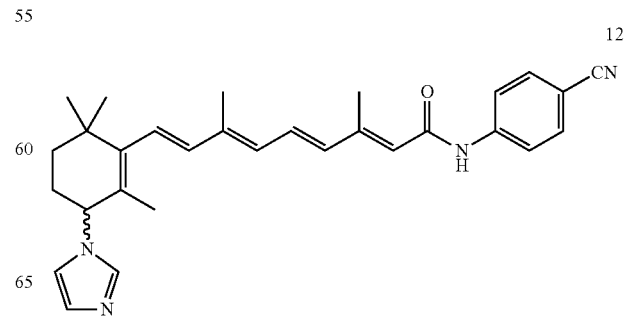

13
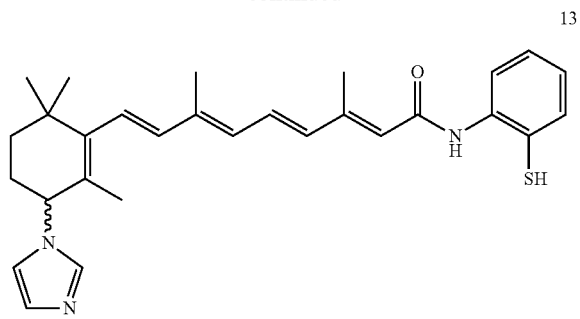
14
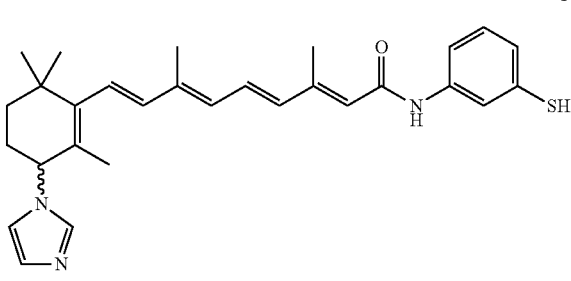
15
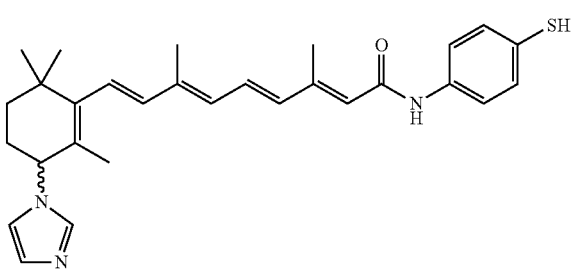
16
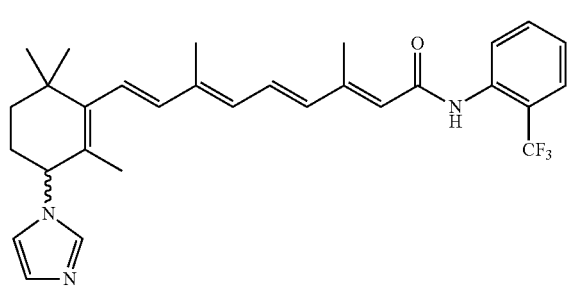
17
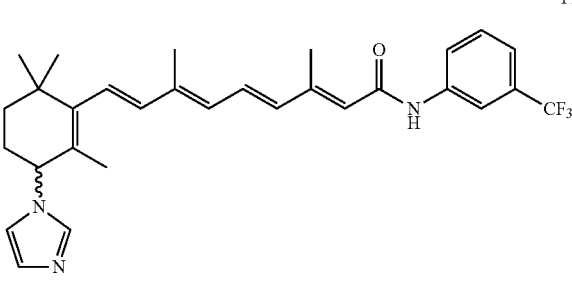
18
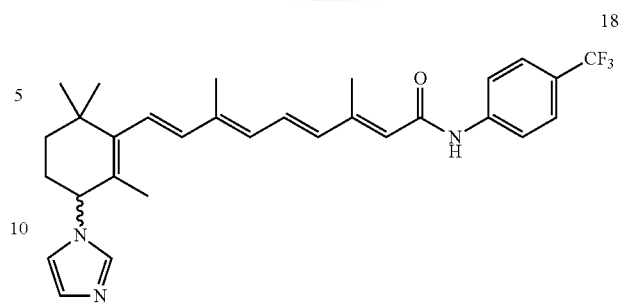
19
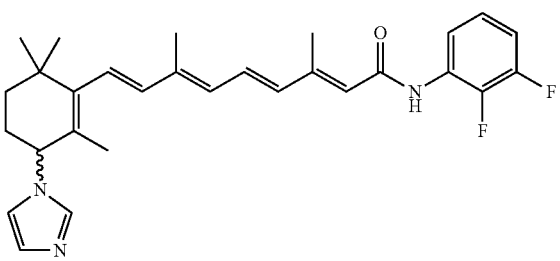
20
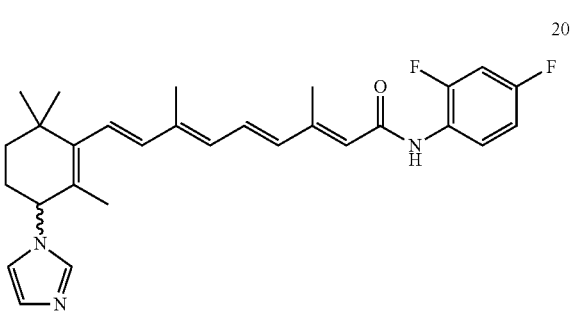
21
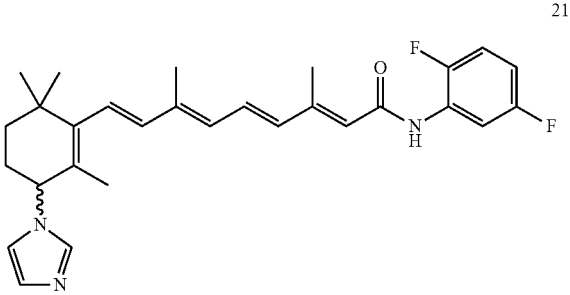
22
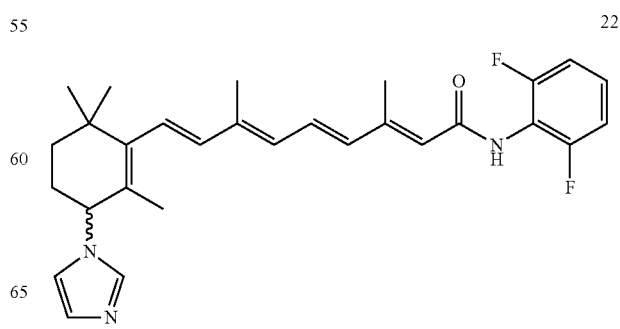

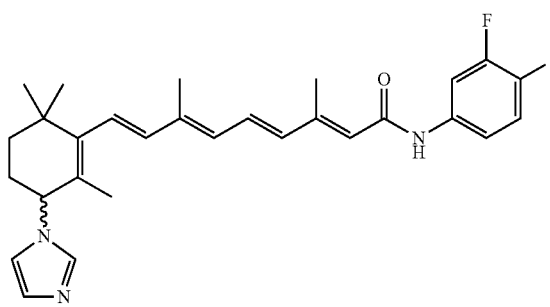
23
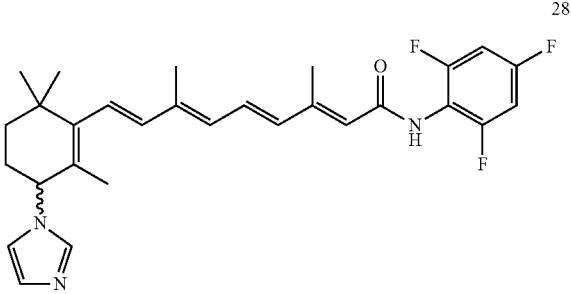
28
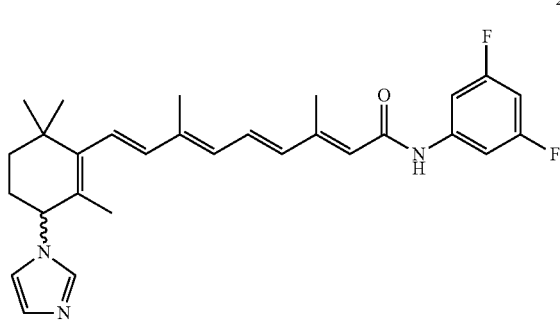
24
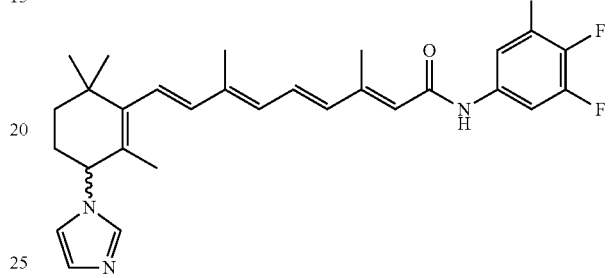
29
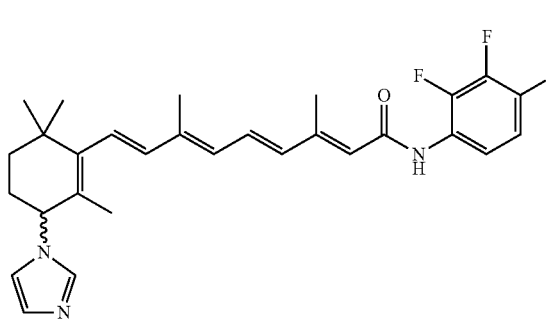
25
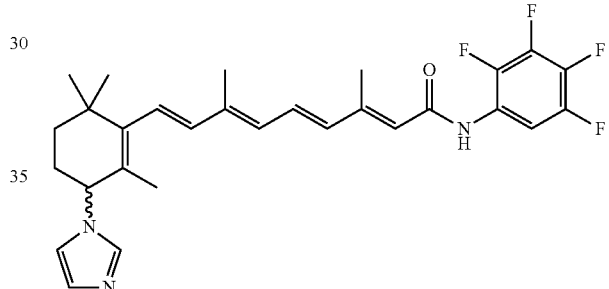
30
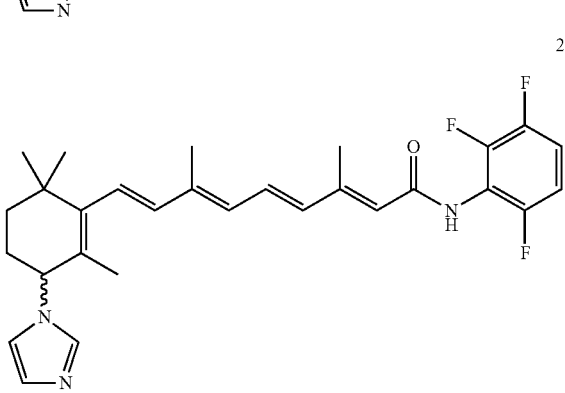
26
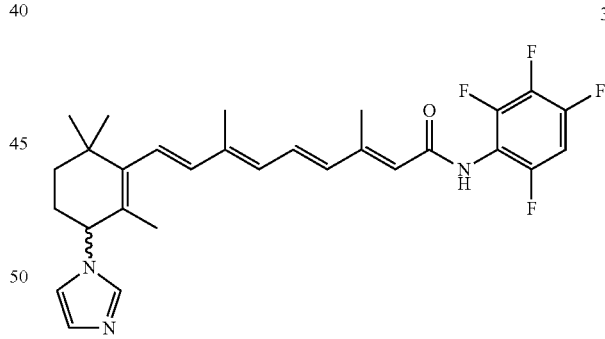
31
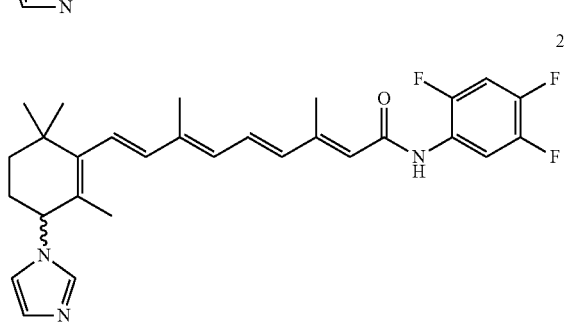
27
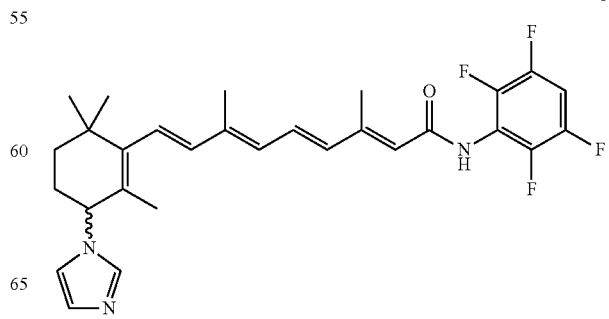
32

33

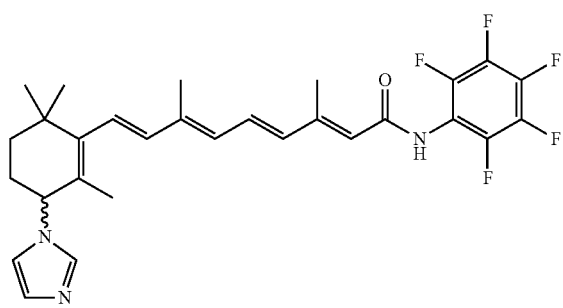

Sulfamoylated and Carbamate RAMBAs

Applicants' invention also includes blocking metabolic conjugation of the phenolic —OH group of the RAMBAs of U.S. Patent by conversion to a corresponding sulfamate and carbamate. This strategy has been successfully used to improve the antiproliferative activity and metabolic stability of 2-methoxyestradiol[xxxv xxxvi xxxvii xxxviii] as well as several dual aromatase-steroid sulfatase inhibitors, some of which have been tested in phase I clinical trials.[xxxix xl]

General Formulae 3A and 3B are new sulfamoylated and carbamate RAMBAs of the present invention.

3A

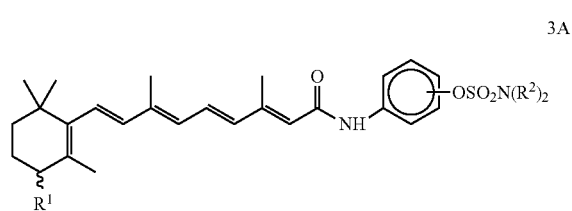

Where $R^1$ has the same definitions as set forth for Formula 2A above; Each $R^2$ is independent and is a hydrogen or an alkyl group. Non-limiting examples of the alkyl group include linear and branched alkyl groups, including primary, secondary and tertiary alkyl groups, and substituted and unsubstituted alkyl groups.

3B

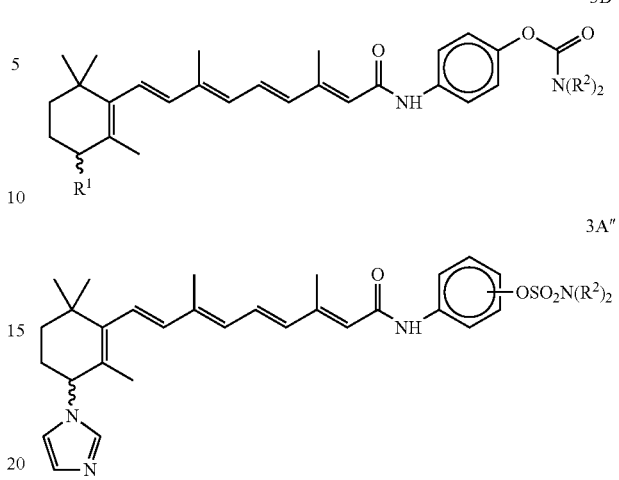

Where $R^1$ and $R^2$ have the same definitions as set forth for Formula 3A above.

Non-limiting examples of General Formulae 3A and 3B include General Formulae 3A', 3B', 3A" and 3B" below.

3A'

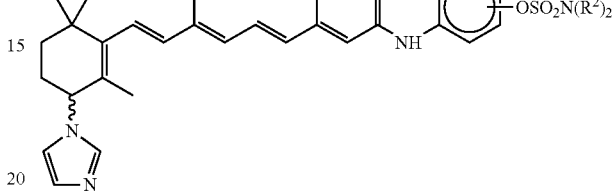

3B'

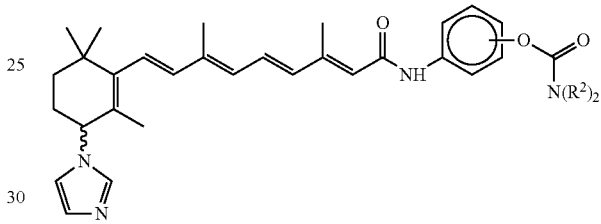

3A"

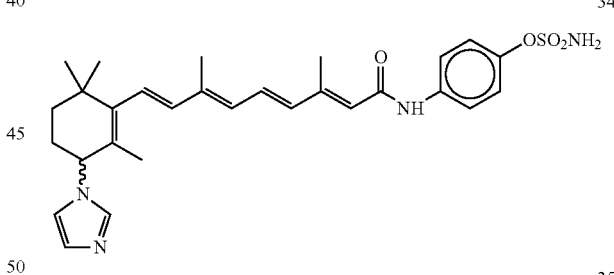

3B"

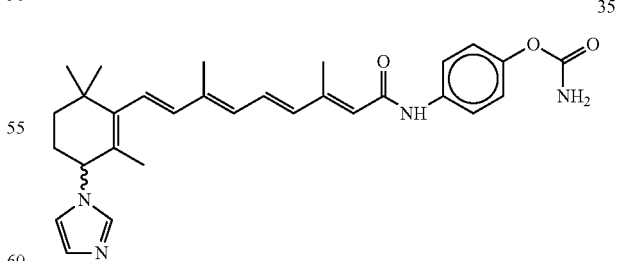

Where $R^1$ and $R^2$ have the same definitions as set forth for Formula 3A above.

Non-limiting examples of General Formulae 3A and 3B are Formula 34 and 35 below:

34

35

Heterocyclic Amide RAMBAs

Applicants' invention also includes new heterocyclic amine containing RAMBAs. General Formulae 4B and 4C are new heterocyclic amine containing RAMBAs of the present invention.

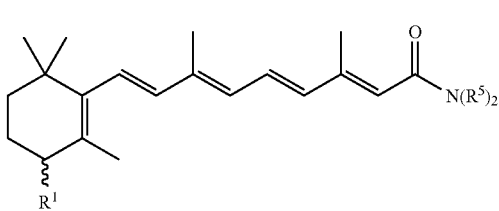

4B

Where R¹ has the same definitions as set forth for Formula 2A above;

Each R⁵ is independently selected from a hydrogen atom, an alkyl group, and a ring containing a nitrogen atom.

Non-limiting examples of the ring containing a nitrogen atom include monocyclic and multicyclic rings, which consist of carbon atoms and one or more nitrogen atoms. The rings may also include other heterocyclic atoms, such as O, S and Si. The rings may be substituted or unsubstituted. Non-limiting examples of the ring containing a nitrogen atom include an amine group, an azine group, a triazine group, an azirene group, an azete group, an diazetidine group, an azole group, a triazole group, a tetrazole group, an imidazole group, an azocane group, a pyridine group, piperidine group, benzimidazole group, and purine groups. The ring containing a nitrogen atom may be substituted or unsubstituted and may be fused with another ring. The ring containing a nitrogen atom may be attached to the nitrogen atom via a carbon group or via a nitrogen group of the ring.

Non-limiting examples of the ring containing a nitrogen atom 2,3,4 triazoles, 1,3 imidazoles, 2,3,4,5 tetrazole.

Non-limiting examples of the alkyl group include linear and branched alkyl groups, including primary, secondary and tertiary alkyl groups, and substituted and unsubstituted alkyl groups. A non-limiting example is a tertiary butyl group.

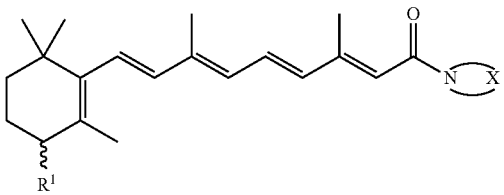

4C

Where R¹ has the same definitions as set forth for Formula 4A above; and

X forms, together with the nitrogen atom, a heterocyclic ring. The heterocyclic ring may be substituted or unsubstituted and may be fused with another ring.

Non-limiting examples of the ring formed by X include monocyclic and multicyclic rings, which consist of carbon atoms and one or more nitrogen atoms. The rings may also include other heterocyclic atoms, such as O, S and Si. The rings may be substituted or unsubstituted. Non-limiting examples of the ring formed by X atom include an amine group, an azine group, a triazine group, an azirene group, an azete group, an diazetidine group, an azole group, a triazole group, a tetrazole group, an imidazole group, an azocane group, a pyridine group, piperidine group, benzimidazole group, and purine groups.

The fused ring may contain all ring carbon atoms or be heterocyclic.

A non-limiting example of a fused heterocyclic rings is a purine group.

Examples of General Formulae 4B and 4C are Formula 4A, 4B' and 4C' below:

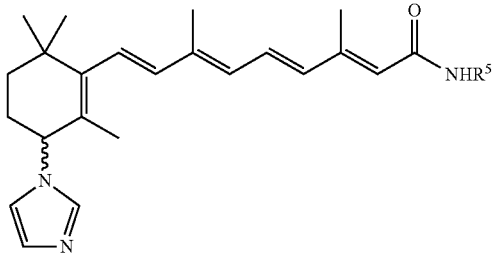

4A

R⁵ has the same definitions as set forth for R⁵ in Formula 5B above.

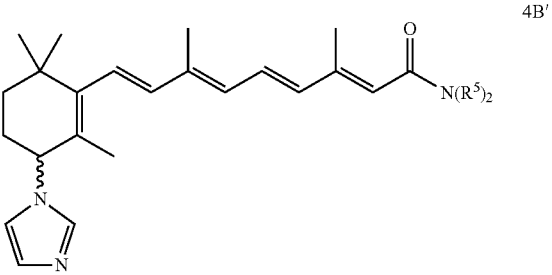

4B'

Where R⁵ and n have the same definitions as set forth for Formula 4B above.

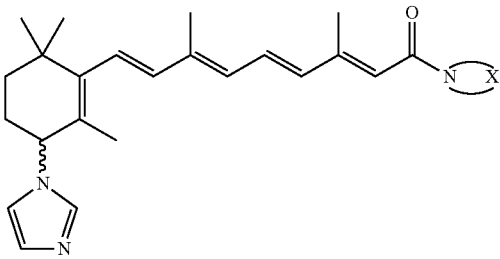

4C'

Where X has the same definitions as set forth for Formula 4C above.

Exemplary compounds of Formula 4B and 4C are Compounds 36-48 and VNLG/148 and VNLG/145 below:

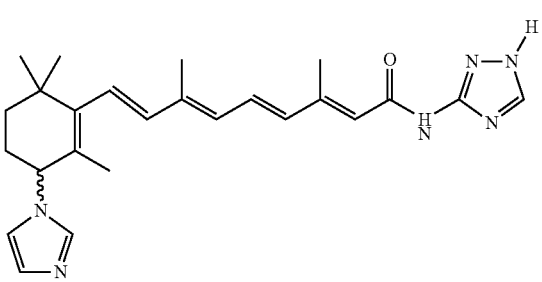

36

15
-continued
37
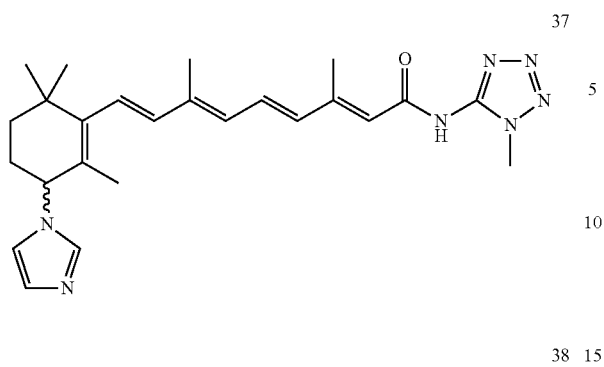
38
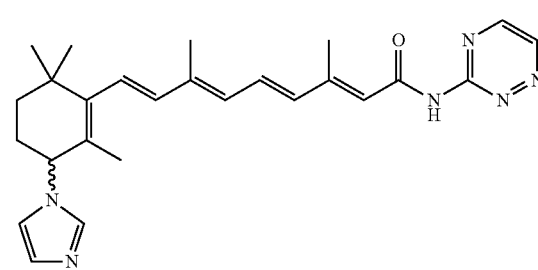
39B
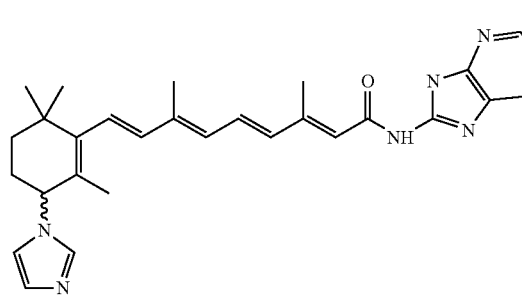
39C
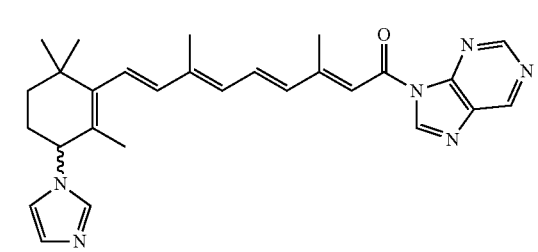
40B
16
-continued
40C
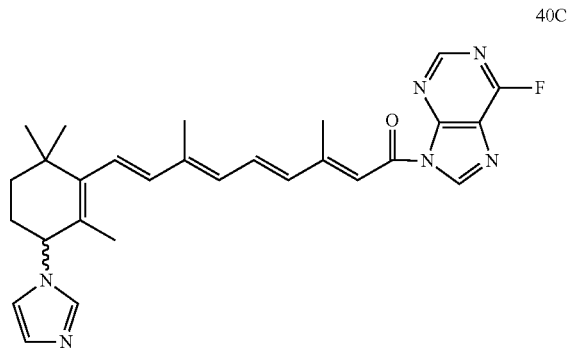
41B
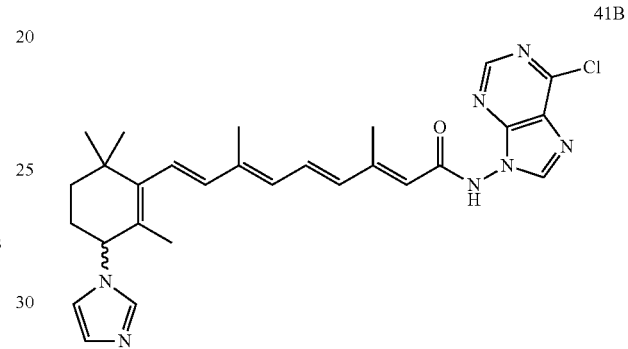
41C
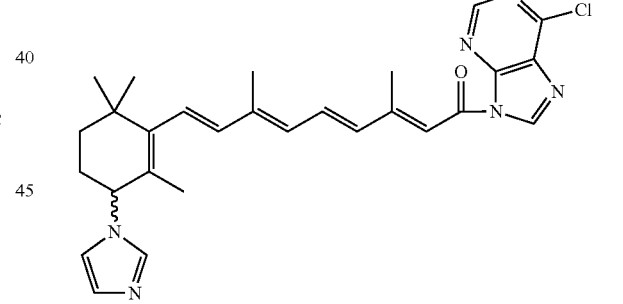
42B
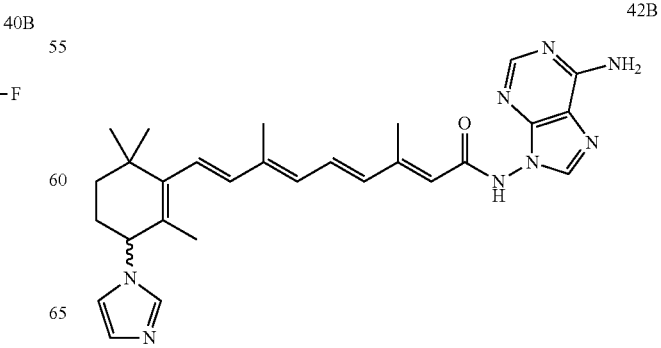

42C
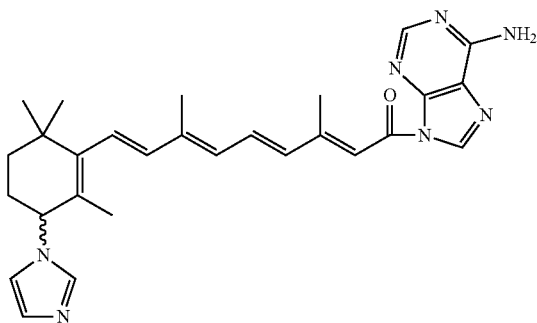
43B
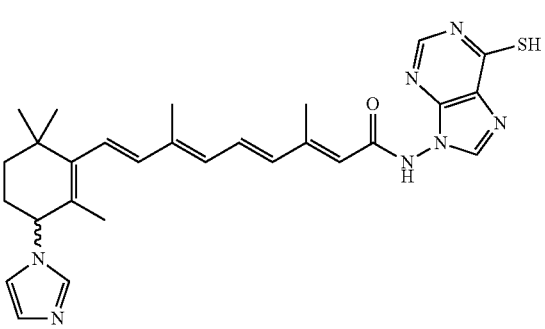
43C
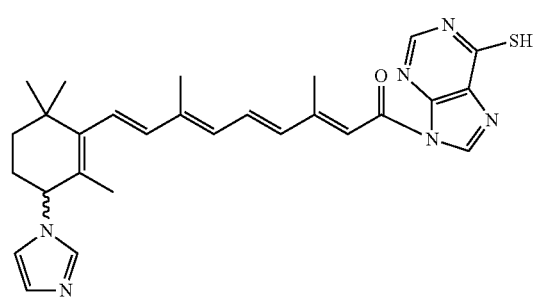
44B
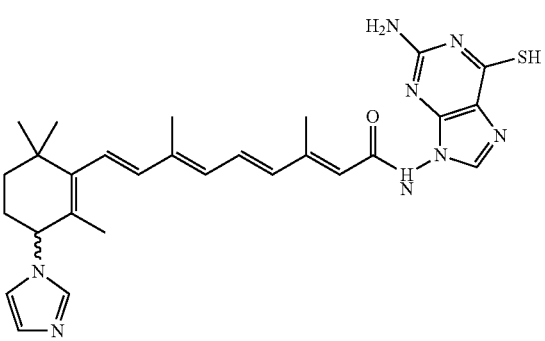
44C
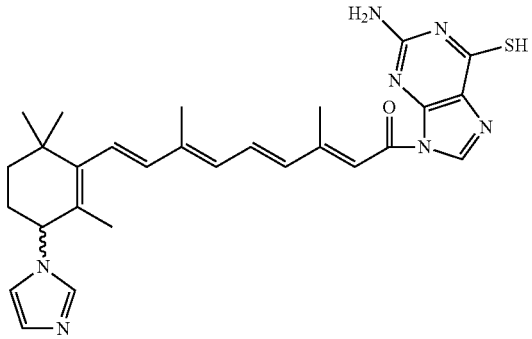
45B
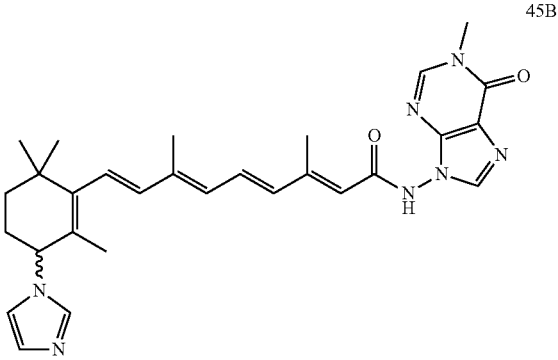
45D
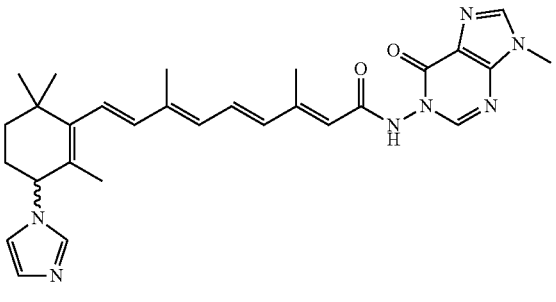
46B
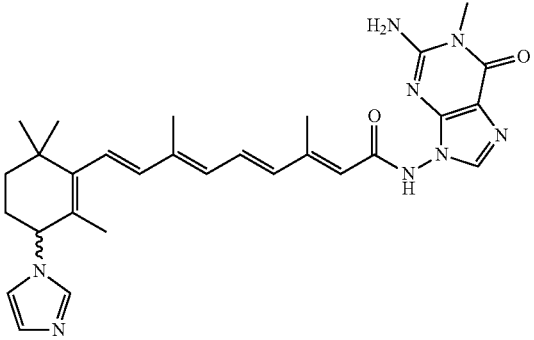

46C
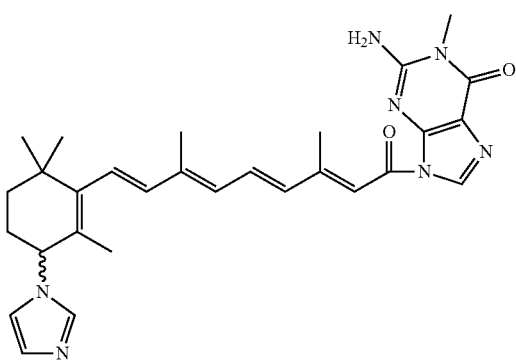
48B
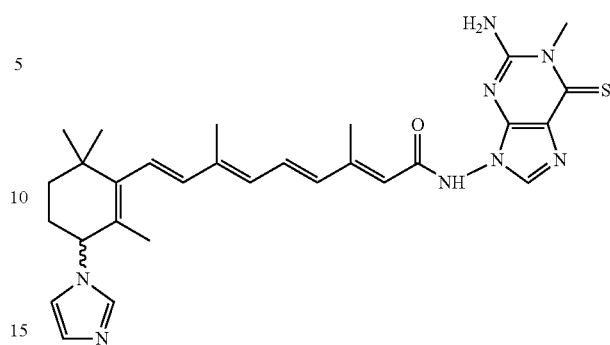
46D
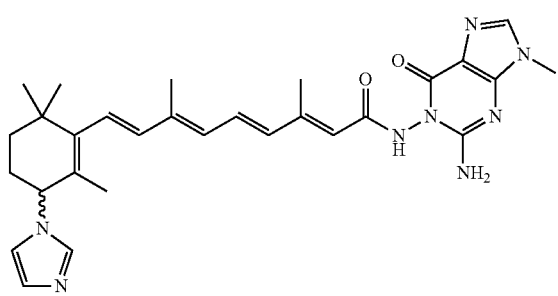
48C
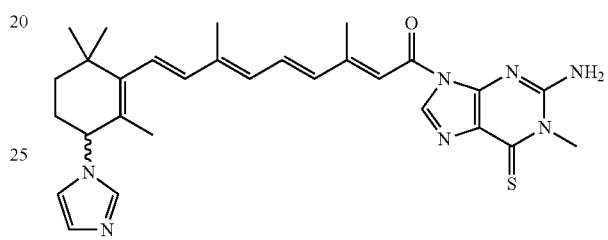
46E
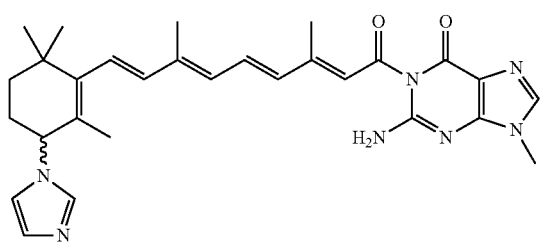
47D
47B
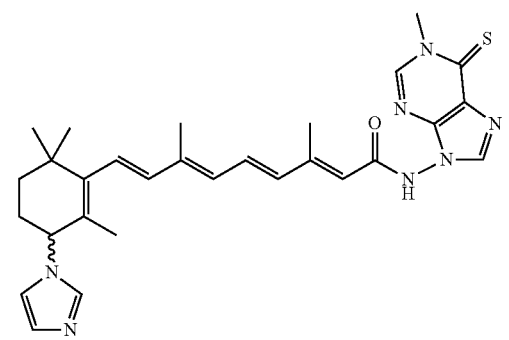
47E
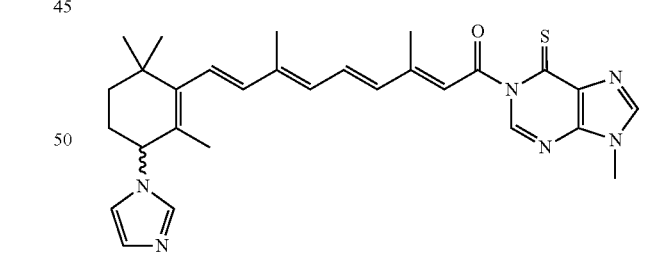
47C
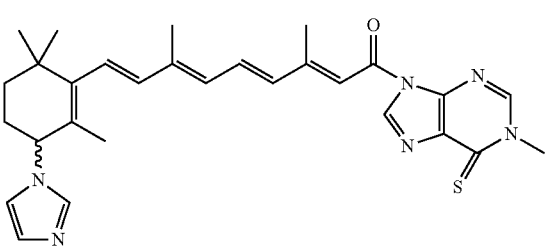
48D
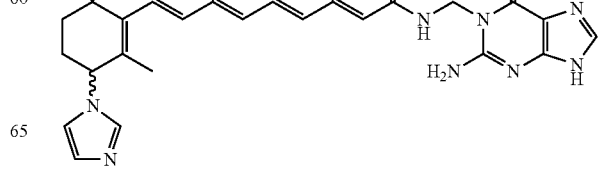

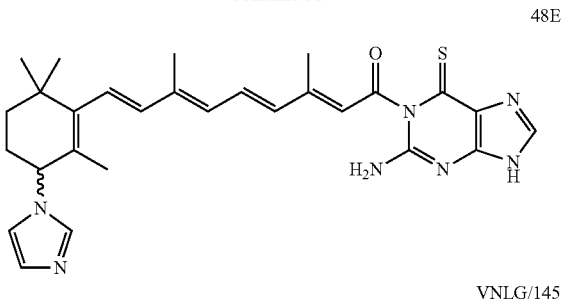

VNLG/145

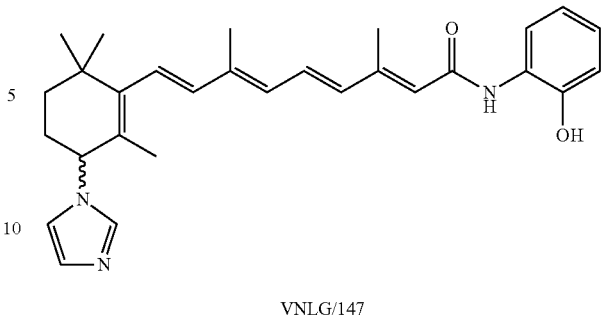

VNLG/147

Synthetic purine derivatives possess great potential to interfere with important cellular functions[xli] and a number of major purine-based drugs exist which find current application for the treatment of cancer[xlii xliii] and a variety of other diseases.[xliv] A further interesting pharmacological property of purine derivatives is that they can be transported across biological membranes by nucleobase active and passive transport systems, which have been characterized in a variety of mammalian cells.[xlv]

Non-4-Position-Hydroxyl RAMBAs

Applicants' invention also includes RAMBA compounds where the hydroxyl group of ring C is not in the 4-position. For Example, General Formula 5 and VNLG/147.

General Formula 5

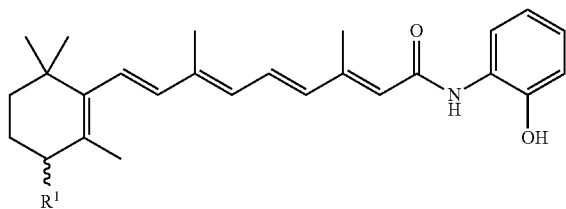

Where $R^1$ has the same definitions as set forth for Formula 2A above.

A non-limiting example of General Formula 5 is VNLG/147.

Enantiomers

The present invention also includes enantiomers of the new RAMBAs of the present application and their use and enantiomers of certain RAMBAs of U.S. Pat. No. 7,265,143 and their use.

VN/66-1 exists as a racemate of two enantiomers as a result of chiral C-4 and studies have been conducted with racemic (±)-VN/66-1. Racemic (±)-VN/12-1 (a potent RAMBA and also the methyl ester of (±)-VN/14-1) is considerably (up to 28-fold) a more potent RAMBA than either of the pure (4S)-(+)- or (4R)-(−)-VN/12-1 enantiomers.[xlvi] However, Applicants consider that the enantiomers may exhibit differential anti-neoplastic activities on PCa cell lines. It has been demonstrated from previous studies that the anti-neoplastic activities of the atypical RAMBAs, including (±)-VN/66-1 are independent of their RAMBA activity.[xlvii xlviii xlix l li lii liii]

Specifically contemplated are synthesis and use of (+)- or (−)- and (±)-VN/66-1 and (+)- or (−)-analogs of the RAMBAs of the present application.

One embodiment of the present invention involves the use of Applicants' new RAMBAs and enantiomers to treat cancer.

It is another object of the present invention to use Applicants' new RAMBAs and enantiomers to treat melanoma, leukemia, including acute promyelocytic leukemia, lymphoma, osteogenic sarcoma, breast, prostate, ovarian, lung, epithelial tumors, colon cancer, pancreatic cancer or other types of cancers.

One embodiment of the present invention is the use of Applicants' RAMBAs and enantiomers to treat breast cancer.

One embodiment of the present invention is the use of Applicants' RAMBAs and enantiomers to treat prostate cancer.

The pharmaceutical composition may contain a pharmaceutically acceptable inactive ingredient. The pharmaceutically acceptable inactive ingredient may be at least one selected from the group consisting of diluent, carrier, solvent, disintregrant, lubricant, stabilizer, and coating.

The method of treatment may be oral administration and the pharmaceutical composition may be formulated for oral administration.

The method of treatment may be parentral administration and the pharmaceutical composition may be formulated for parentral administration, including subcutaneous, intramuscular, intracapsular, intraspinal, intrasternal, or intravenous.

The compound may be used in a pharmaceutical composition. The pharmaceutical composition may be formulated for oral administration, parentral administration or for injectable administration.

In making the compositions of the present invention, the compounds of the present invention can be mixed with a pharmaceutically acceptable carrier or an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier, or medium for the compounds. Thus, the compositions can be in the form of tablets, pills, powers, lozenges, sachets, cachets, elixirs, suspensions, emulsions, solutions, syrups, soft and hard gelatin capsules, and other orally ingestible formulations.

The pharmaceutical compositions may be in the form of a solution, suspension, tablet, capsule or the like, prepared according to methods well known in the art. It is also contemplated that administration of such compositions may be by the oral, injectable and/or parenteral routes depending upon the needs of the artisan. The compounds of the present invention can be administered by nasal or oral inhalation, oral ingestion, injection (intramuscular, intravenous, and intraperitoneal), transdermally, or other forms of administration.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include lubricating agents such as talc, magnesium stearate, and mineral oil; wetting agents; emulsifying and suspending agents; preserving agents such as methyl- and propyl-hydroxybenzoates, sweetening agents; and flavoring agents. The compositions of the present invention can also be formulated so as to provide quick, sustained or delayed release of the compounds of the present invention after administration to the patient by employing procedures known in the art.

The term "pharmaceutically acceptable carrier" refers to those components in the particular dosage form employed which are considered inert and are typically employed in the pharmaceutical arts to formulate a dosage form containing a particular active compound. This may include without limitation solids, liquids and gases, used to formulate the particular pharmaceutical product. Examples of carriers include diluents, flavoring agents, solubilizers, suspending agents, binders or tablet disintegrating agents, encapsulating materials, penetration enhancers, solvents, emollients, thickeners, dispersants, sustained release forms, such as matrices, transdermal delivery components, buffers, stabilizers, and the like. Each of these terms is understood by those of ordinary skill.

Aerosol formulations for use in this invention typically include propellants, such as a fluorinated alkane, surfactants and co-solvents and may be filled into aluminum or other conventional aerosol containers which are then closed by a suitable metering valve and pressurized with propellant, producing a metered dose inhaler. Aerosol preparations are typically suitable for nasal or oral inhalation, and may be in powder or solution form, in combination with a compressed gas, typically compressed air. Additionally, aerosols may be useful topically.

The amount of the compounds used in the treatment methods is that amount which effectively achieves the desired therapeutic result in animals. Naturally, the dosages of the various compounds of the present invention will vary somewhat depending upon the parent compound, rate of in vivo hydrolysis, etc. Those skilled in the art can determine the optimal dosing of the compounds of the present invention selected based on clinical experience and the treatment indication. The amount of the compounds of the present invention may be 0.1 to 100 mg/kg of body weight, more preferably, 5 to 40 mg/kg.

Suitable solid carriers are known, e.g., magnesium carbonate, magnesium stearate, talc, lactose and the like. These carriers are typically used in oral tablets and capsules.

Suitable carriers for oral liquids include, e.g., water, ethanol, propylene glycol and others.

Topical preparations useful herein include creams, ointments, solutions, suspensions and the like. These may be formulated to enable one to apply the appropriate dosage topically to the affected area once daily, up to 3-4 times daily as appropriate. Topical sprays may be included herein as well.

Depending upon the particular compositions selected, transdermal delivery may be an option, providing a relatively steady state delivery of the medication which is preferred in some circumstances. Transdermal delivery typically involves the use of a compound in solution, with an alcoholic vehicle, optionally a penetration enhancer, such as a surfactant and other optional ingredients. Matrix and reservoir type transdermal delivery systems are examples of suitable transdermal systems. Transdermal delivery differs from conventional topical treatment in that the dosage form delivers a systemic dose of medication to the patient.

The delivery may be enhanced by promoting a more pharmacologically effective amount of the compound reaching a site of action, preferably a cancerous tumor site. The delivery may also be enhanced by promoting a more effective delivery of the compound across a cell membrane or within the cell and across the intra-cellular space.

The RAMBAs can be converted into a pharmaceutically acceptable salt or pharmaceutically acceptable solvate or other physical forms (e.g., polymorphs by way of example only and not limitation) via known in the art methods. The RAMBA compounds of the present invention can also be administered as a prodrug or as a separate compound.

The method of treatment may be injectable administration and the pharmaceutical composition may be formulated for injectable administration.

As used herein, "treat" and all its forms and tenses (including, for example, treat, treating, treated, and treatment) refer to both therapeutic treatment and prophylactic or preventative treatment. Those in need of treatment include those already with a pathological condition of the invention (including, for example, cancer) as well as those in which a pathological condition of the invention is to be prevented. For example, "treat" means alter, apply, effect, improve, care for or deal with medically or surgically, ameliorate, cure, stop and/or prevent an undesired biological (pathogenic) process. The skilled artisan is aware that a treatment may or may not cure.

As used herein, the effective amount or "therapeutically effective amounts" of the compound of the present invention to be used are those amounts effective to produce beneficial results in the recipient animal or patient. Such amounts may be initially determined by knowledge in the art, by conducting in vitro tests or by conducting metabolic studies in healthy experimental animals.

A therapeutically effective amount of a compound of the present invention as a treatment varies depending upon the host treated and the particular mode of administration.

In addition to a single therapy, which is the case with the administration of, for example, a single compound of the invention, cancer treatments are commonly combined with other methods of treating cancer. Combination therapy includes combining the method of treating cancer as described in the invention and one or more cancer therapeutic methods. Cancer therapeutic methods include surgical therapy, radiation therapy, administering an anticancer agent (including, for example, antineoplastics (including, for example, novantrone, bicalutamide, esterified estrogens, goserelin, histrelin, leuprolide, nilandron, triptorelin pamoate, docetaxel, taxotere, carboplatin, and cisplatin) or combinations thereof, and angiogenesis inhibitors), immunotherapy, antineoplastons, investigational drugs, vaccines, less conventional therapies (sometimes referred to as novel or innovative therapies, which include, for example, chemoembolization, hormone therapy, local hyperthermia, photodynamic therapy, radiofrequency ablation, stem cell transplantation, and gene therapy), prophylactic therapy (including, for example, prophylactic mastectomy or prostatectomy), and alternative and complementary therapies (including, for example, dietary supplements, megadose vitamins, herbal preparations, special teas, physical therapy, acupuncture, massage therapy, magnet therapy, spiritual healing, meditation, pain management therapy, and naturopathic therapy (including, for example, botanical medicine, homeopathy, Chinese medicine, and hydrotherapy)).

The method of treatment and the pharmaceutical composition may further comprise an all-trans retinoic acid (ATRA) and/or another RAMBA, including the use of multiple RAMBAs of the present invention.

BRIEF DESCRIPTION OF THE SEVERAL VIEWS OF THE DRAWINGS

FIG. 1 shows the antiproliferative effects of VNLG/145 PC-3 cell proliferation measured after 6 days of treatment using a MTT assay. Data are means (SEM<±5%) of at least three independent experiments.

DETAILED DESCRIPTION OF THE INVENTION

Synthesis
Anilineamide RAMBAs

Scheme 1 and Scheme 2 below are examples of the syntheses of the Anilineamide RAMBAs. The examples involves the coupling of the imidazolyl carboxylic acid (VN/14-1) with various anilines using 1,3-dicyclohexylcarbodiimide (DCC) and 1-hydroxybenzotriazole (HOBT) in dimethylformamide (DMF) to yield the corresponding amides. This synthesis has been used for synthesis of VNLG/145, VNLG/146, VNLG/147, VNLG/148, VNLG/152, and VNLG/153 and VN/66-1.

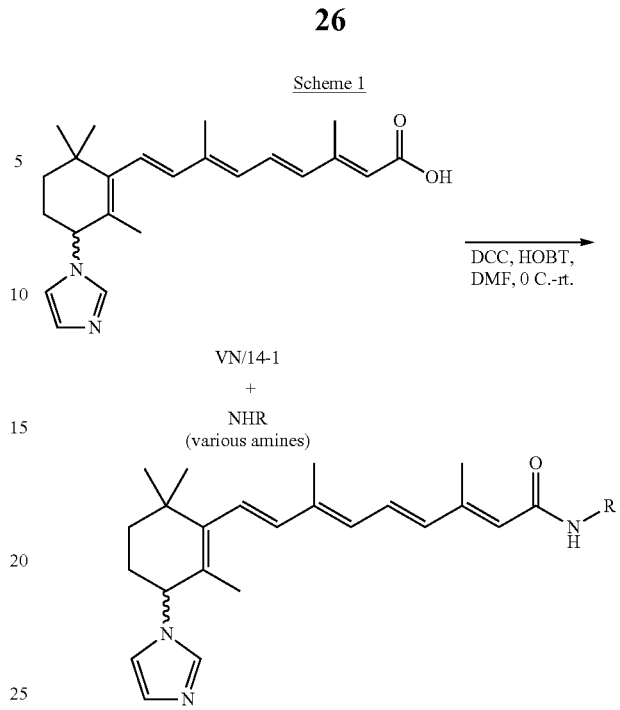

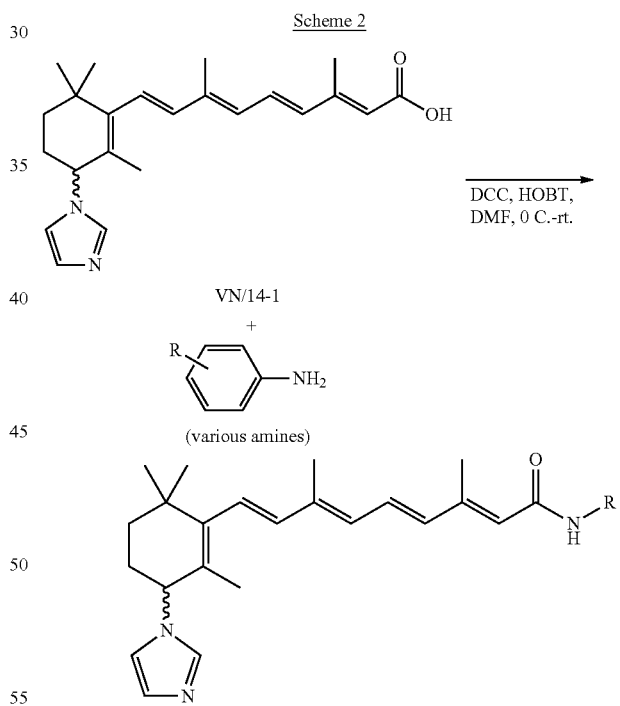

Sulfamoylated and Carbamate RAMBAs

Scheme 3 below shows an example of the synthesis of Compounds 34 and 35. VN/66-1 may be sulfamoylated under standard conditions[liv,iv], with sulfomoyl chloride in dimethyl acetamide to give Compound 34. The carbamate (35) may be synthesized in two steps from VN/66-1, first reacted with trichloroacetyl isocyanate to give the N-trichloroacetyl carbamate, followed by hydrolysis with $K_2CO_3$ in MeOH/THF/$H_2O$) to give Compound 35. N,N-dialkyl derivatives of 34 and 35 may be synthesized by reaction with appropriate alkyl halides under basic conditions.[lvi]

Scheme 3: Synthesis of compounds 34 and 35

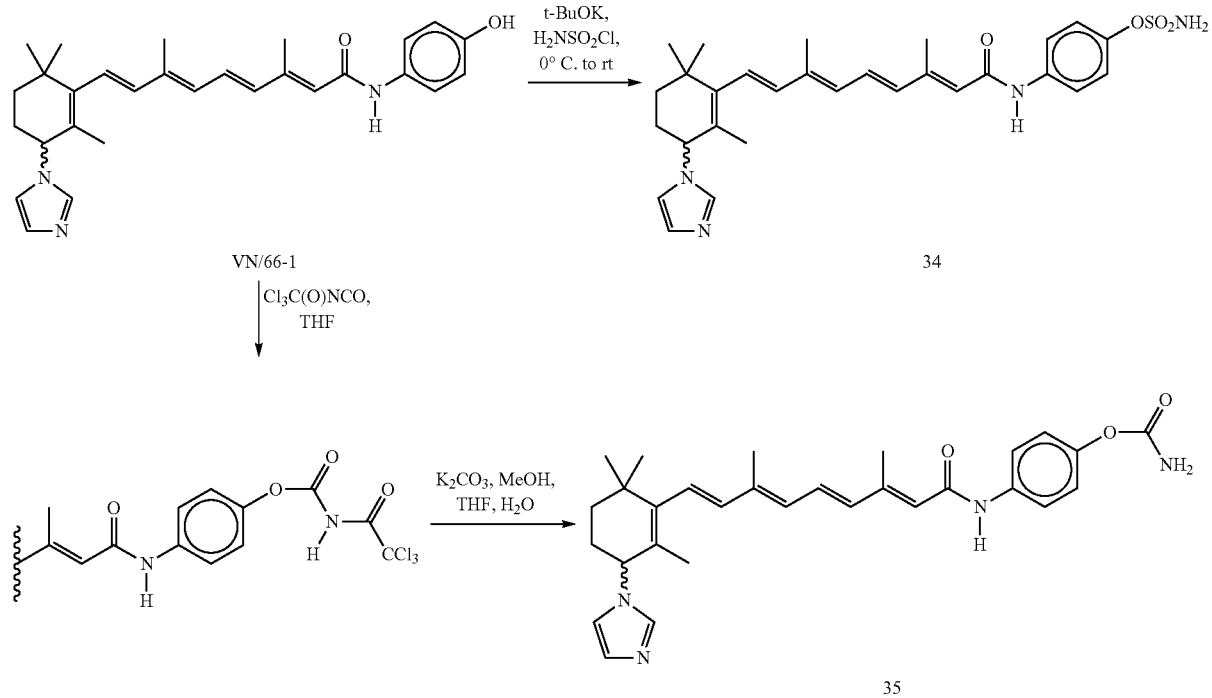

Heterocyclic Amide RAMBAs

The heterocyclic and amide RAMBAs of the present invention may be synthesized as outlined in Scheme 4 below. Some reactions will involve the coupling of the imidazolyl carboxylic acid (VN/14-1) with various anilines using 1,3-dicyclohexylcarbodiimide (DCC) and 1-hydroxybenzotriazole (HOBT) in dimethylformamide (DMF) to yield the corresponding amides. While other compounds will involve formation (i.e., reactions with carbonyldiimidazole (CDI)) of imidazolide intermediates followed by coupling with appropriate amino heterocyles.[lvii] For synthesis of Compounds 42, 44, 46 and 48, the primary amino groups will first be protected with di-tert-butyl dicarbonate $(Boc)_2O$[lviii] prior to use for coupling reactions. The Boc groups will then be readily deprotected to give the desired compounds. With the recent availability of simple procedures for the synthesis of large numbers of substituted purines[lix], purine related compounds may be synthesized.

Scheme 4

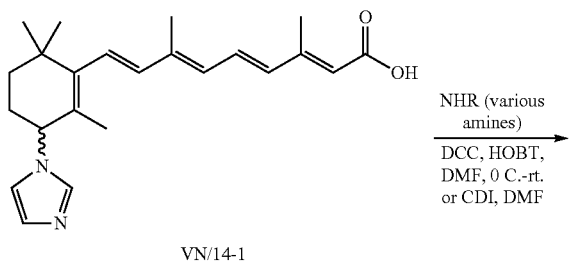

-continued

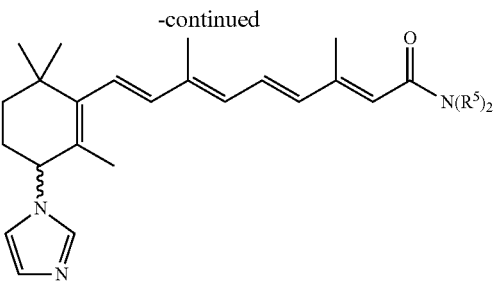

Non-4-Position-Hydroxyl RAMBAs

The compounds of General Formulae 5 may be made with synthesis methods similar to those for making VN/66-1.

In the above synthesis methods, the starting RAMBA may be a racemate or a (+) or (−) enantiomer to obtain an enantiomer of the RAMBAs of the present invention.

The synthesized compounds (intermediates and final products) may be purified by chromatographic procedures (flash column chromatography, TLC or HPLC) and/or crystallization. The compounds may be fully characterized by spectroscopic methods (IR, UV, NMR and MS) and elemental analyses. The melting points of all compounds may be determined with a Fisher-Johns melting point apparatus.

Enantiomers

Synthesis of VN/66-1 enantiomers: One synthesis of enatiopure (4S)-(+)-VN/66-1 and (4R)-(−)-VN/66-1 is outlined in Scheme 1 below, starting from racemic (4S,R)-(±)-4-hydroxymethylretinoate which will be readily synthesized from commercially available all-trans-retinoic acid (ATRA) as previously described.[lx, lxi] Next the recent efficient and high yielding procedure reported by Learmonth[lxii] will be used to resolve the racemic allylic alcohol (1) to give the enantiopure alcohols 2 and 3. The procedure involves use of diacetyl-L- tartaric acid anhydride to precipitate the diastereoisomeric precursor (1a) of (4S)-(+)-1 and diacetyl-D-tartaric acid anhydride to precipitate the diastereoisomeric precursor (1b) of (R)-(−)-1 followed by mild hydrolysis to give eantiopure alcohols (Scheme 1). Based on previous studies, it is expected that the terminal methyl ester group will be stable under the mild hydrolysis of the diastereoisomers.[lxiii, lxiv] These two alcohols are expected to have optical purity in the range 92 to 99%, which will be purified to 100% ee either by several recrystallizations or by HPLC using a Chiralcel OJ semi-preparative column.[lxv] The enantiopure alcohols 2 and 3 will each be used to synthesize enatiopure (4S)-(+)-VN/66-1 and (4R)-(−)-VN/66-1 as previously described[lxvi, lxvii] and will be characterized by HPLC, $^1$H-NMR and optical rotation. It has been previously reported that conversion of the allylic alcohol to the corresponding imidazole via reaction with carbonyl diimidazole proceeds via $SN_i$ mechanism with retention of configuration[lxviii] corroborated by earlier studies.[lxix]

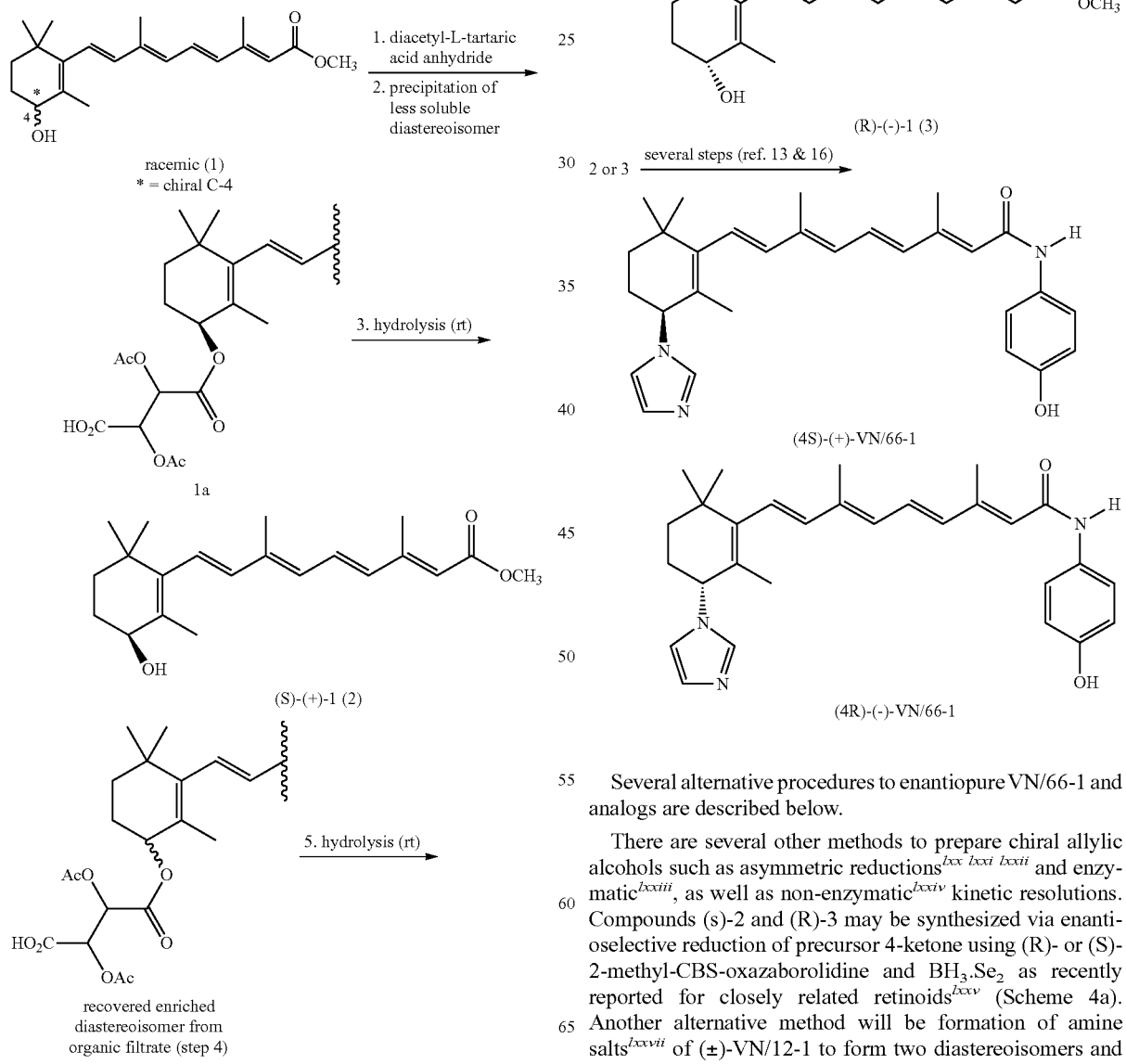

Scheme 1: Syntheses of enantiopure C-4 alcohols and (4S)-(+)-VN/66-1 and (4R)-(−)-VN/66-1

Several alternative procedures to enantiopure VN/66-1 and analogs are described below.

There are several other methods to prepare chiral allylic alcohols such as asymmetric reductions[lxx, lxxi, lxxii] and enzymatic[lxxiii], as well as non-enzymatic[lxxiv] kinetic resolutions. Compounds (s)-2 and (R)-3 may be synthesized via enantioselective reduction of precursor 4-ketone using (R)- or (S)-2-methyl-CBS-oxazaborolidine and $BH_3.Se_2$ as recently reported for closely related retinoids[lxxv] (Scheme 4a). Another alternative method will be formation of amine salts[lxxvii] of (±)-VN/12-1 to form two diastereoisomers and subsequent separation by crystallization.

Another alternative method will be formation of amine salts[lxxvii] of (±)-VN/66-1 to form two diastereoisomers and subsequent separation by crystallization.

The coupling of some amines may be difficult. Applicants propose to use alternative strategies of amide syntheses as outlined in Scheme 4b below. These procedures involve either key pyridylthioester intermediate[lxxviii] or solid phase synthesis that involves reaction of the carboxylic acid with an activating chlorinating reagent.[lxxix]

(+)-VN/66-1 and (−)-VN/66-1 may also be tested to check for differential anti-neoplastic activities against the four prostate cancer cell lines.

Applicants also consider that the enantiopure (+)- and (−)-VN/66-1 may be more stable in in vitro and more importantly, in vivo.

In vitro stability of entiopure (+)- or (−)-VN/66-1 and the derivatives of VN/66-1 may be assessed by treating PCa cells Scheme 4a & b: Alternative syntheses of enantiopure alcohols and retinamides a.

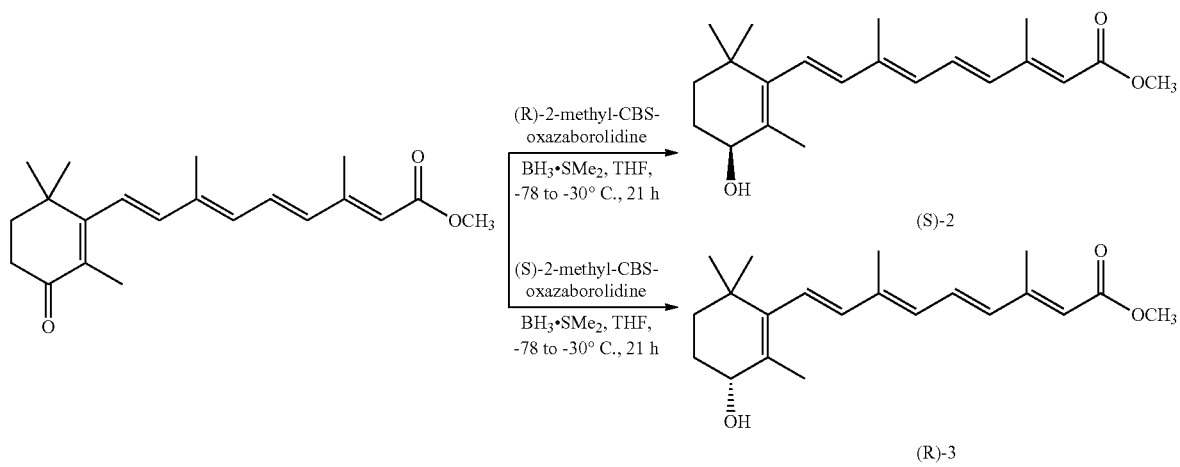

b.

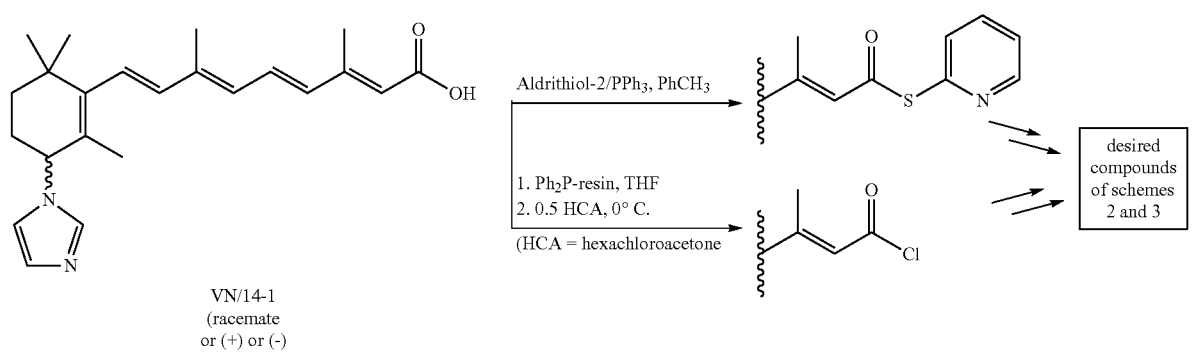

Evaluation

The new compounds synthesized may be screened at 1 and 10 µM concentrations for their ability to inhibit ATRA metabolizing enzymes using established procedure.[lxxx lxxxi lxxxii lxxxiii lxxxiv] Compounds may also be evaluated to determine their concentrations that will cause 50% enzyme inhibition ($IC_{50}$ values).

Potent RAMBAs from U.S. Pat. No. 7,265,143 VN/14-1 and VN/66-1 and liarozole can be used to determine the relative potencies of the new compounds.

Assessments of VN/66-1 Enantiomers In Vitro and In Vivo:

The RAMBA activities of the pure enantiomers, racemic VN/66-1 and 4-HPR (standard) and also their growth inhibitory effects on four PCa cell lines (LNCaP, LAPC4, $C_4$-2B and LAPC4-BR may be tested. The RAMBA activities of with their $IC_{50}$ and $IC_{90}$ concentrations. Cells and media may be extracted at specific time intervals over the usual MTT assay conditions, and than analyzed by chiral HPLC column. To further evaluate their stabilities in vivo, animals may be dosed with 10 mg/kg of pure (+)- or (−)-VN/66-1. Blood will be drawn at specified times, processed and than analyzed as described above.

Examples

Applicants synthesized novel retinamides of the present invention with reactions that involve coupling of our imidazolyl carboxylic acid (VN/14-1) with appropriate amines/ anilines using 1,3-dicyclohexylcarbodiiimide (DCC) and 1-hydroxybenzotriazole (HOBT) in dimethylformamide (DMF) as outlined in Scheme 1 below.

Scheme 1: Synthesis of Novel Retinamides (VNLG/145-VNLG/153)

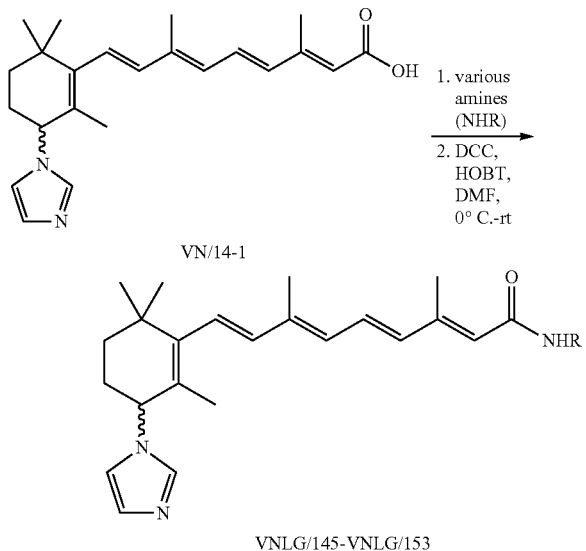

Compounds VNLG/145, VNLG/146, VNLG/147, VNLG/148, VNLG/152 and VNLG/153 were tested and evaluated for their ability to inhibit the growth (proliferation) of PC-3 prostate cancer cells using the MTT [3-(4,5-dimethylthiazol-2-yl)-2,5-diphenyltetrazolium bromide] assay (Gediyal et al. 2005). VN/66-1 of U.S. Pat. No. 7,265,143 was tested side by side for comparison. The $GI_{50}$ values (concentrations that cause 50% growth inhibition) were determined from dose-response curves. See in FIG. 1 for VNLG/145.

The growth inhibitory experiments with the other compounds gave plots that were similar to FIG. 1.

The structures of the six compounds of the present invention and the parent VN/66-1 and their $GI_{50}$ values are presented in Table 1 below.

TABLE 1

| Compounds | GI50 Values (µM) |
|---|---|
| VNLG/145 | 1.86 ± 0.05 |
| VNLG/146 | 14.13 ± 7.12 |
| VNLG/147 | 1.70 ± 0.07 |

TABLE 1-continued

| Compounds | GI50 Values (μM) |
|---|---|
| 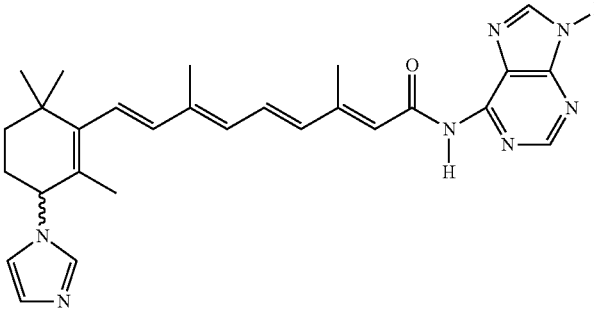 VNLG/148 | 5.62 ± 0.37 |
| 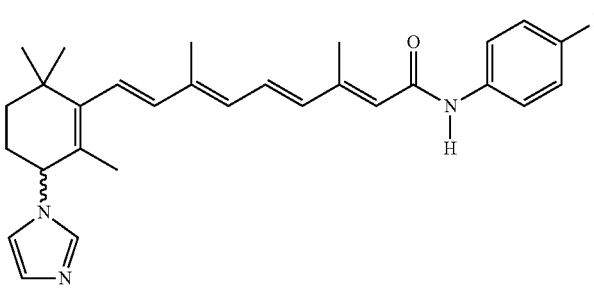 VNLG/152 | 0.61 ± 0.11 |
| 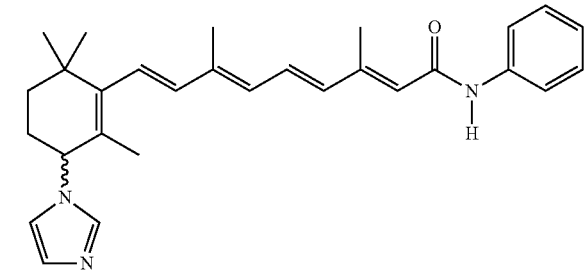 VNLG/153 | 1.17 ± 0.05 |
| 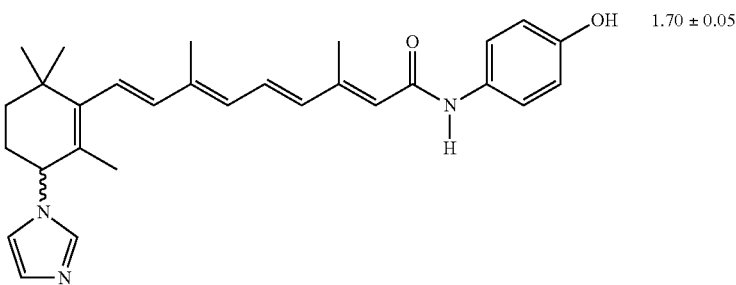 VN/66-1 | 1.70 ± 0.05 |

VNLG/152 is the same as Compound 6 above.

VNLG/152 and VNLG/153 exhibited potencies better than VN/66-1.

VNLG/145 and VNLG/147 exhibited potencies similar to VN/66-1.

It is contemplated that VNLG/145, VNLG/146, VNLG/147, VNLG/148, VNLG/152 and VNLG/153 (except for VNLG/147 (with a 2-hydroxy group)) may exhibit superior in vivo antineoplastic activity attributable to putative superior absorption, distribution, metabolism, and excretion (ADME) properties.

As used herein in the specification, "a" or "an" may mean one or more. As used herein in the claims, when used in conjunction with the word "comprising," the words "a" or "an" may mean one or more than one. As used herein "another" may mean at least a second or more. Furthermore, unless otherwise required by context, singular terms shall include pluralities and plural terms shall include the singular.

It is believed that the present invention and many of its attendant advantages will be understood by the forgoing description. It is also believed that it will be apparent that various changes may be made in the form, construction and arrangement of the components thereof without departing from the scope and spirit of the invention or without sacrificing all of its material advantages. The form herein before described being merely an explanatory embodiment thereof.

[i] Sonneveld et al, *Human retinoic acid (RA) 4-hydroxylase (CYP26) is highly specific for all-trans-RA and can be induced through RA receptors in human breast and colon carcinoma cells*, Cell Growth Differ, 9: 629-637, 1998

[ii] Lotan et al., *Retinoids and apoptosis, implications for cancer chemoprevention and therapy*, J Natl Cancer Inst, 87: 1655-1657, 1995

[iii] Mangelsdorf et al., *The nuclear receptor superfamily, the second decade*, Cell, 83: 835-839, 1995

[iv] Jonk, L. J., de Jonge, M. E., Vervaart, J. M., Wissink, S., and Kruijer, W. Isolation and developmental expression of retinoic-acid-induced genes. Dev Biol, 161: 604-614, 1994

[v] Altucci et al., *The promise of retinoids to fight against cancer*, Nat Rev Cancer, 1: 181-193, 2001.; Njar et al., *Retinoids in clinical use*, Med Chem, 2: 431-438, 2006

[vi] Pasquali et al., *Abnormal level of retinoic acid in prostate cancer tissues*, J Clin Endocrinol Metab, 81: 2186-2191, 1996

[vii] Altucci et al., *The promise of retinoids to fight against cancer*, Nat Rev Cancer, 1: 181-193, 2001.; Njar et al., Retinoids in clinical use, Med Chem, 2: 431-438, 2006

[viii] Miller, W. H., Jr., *The emerging role of retinoids and retinoic acid metabolism blocking agents in the treatment of cancer*, Cancer, 83: 1471-1482, 1998; Njar, V. C., *Cytochrome p450 retinoic acid 4-hydroxylase inhibitors, potential agents for cancer therapy*, Mini Rev Med Chem, 2: 261-269, 2002; Njar et al., *Retinoic acid metabolism blocking agents (RAMBAs) for treatment of cancer and dermatological diseases*, Bioorg Med Chem, 14: 4323-4340, 2006; Njar et al., *Potent inhibition of retinoic acid metabolism enzyme(s) by novel azolyl retinoids*, Bioorg Med Chem Lett, 10: 1905-1908, 2000

[ix] Miller, W. H., Jr. *The emerging role of retinoids and retinoic acid metabolism blocking agents in the treatment of cancer*, Cancer, 83: 1471-1482, 1998; Njar, V. C. *Cytochrome p450 retinoic acid 4-hydroxylase inhibitors, potential agents for cancer therapy*, Mini Rev Med Chem, 2: 261-269, 2002; Njar et al., *Retinoic acid metabolism blocking agents (RAMBAs) for treatment of cancer and dermatological diseases*, Bioorg Med Chem, 14: 4323-4340, 2006; Belosay et al., *Effects of novel retinoic acid metabolism blocking agent (VN/14-1) on letrozole-insensitive breast cancer cells*, Cancer Res, 66-11485-11493, 2006; Huynh et al., *Inhibitory effects of retinoic acid metabolism blocking agents (RAMBAs) on the growth of human prostate cancer cells and LNCaP prostate tumour xenografts in SCID mice*, Br J Cancer, 94: 513-523, 2006; Patel et al., *Novel retinoic acid metabolism blocking agents endowed with multiple biological activities are efficient growth inhibitors of human breast and prostate cancer cells in vitro and a human breast tumor xenograft in nude mice*, J Med Chem, 47-6716-6729, 2004l; Patel et al., *Novel retinoic acid metabolism blocking agents have potent inhibitory activities on human breast cancer cells and tumour growth*, Br J Cancer, 96-1204-1215, 2007

[x] Debruyne et al., *Liarozol—a novel treatment approach for advanced prostate cancer: results of a large randomized trial versus cyproterone acetate*, Liarozole Study Group. Urology, 52: 72-81, 1998

[xi] Njar et al., *Retinoids in clinical use*, Med Chem, 2: 431-438, 2006; Njar et al., *Retinoic acid metabolism blocking agents (RAMBAs) for treatment of cancer and dermatological diseases*, Bioorg Med Chem, 14: 4323-4340, 2006; Lucker et al., *Topical liarozole in ichthyosis, a double-blind, left-right comparative study followed by a long-term open maintenance study*, Br J Dermatol, 152: 566-569, 2005

[xii] Altucci et al., *The promise of retinoids to fight against cancer*, Nat Rev Cancer, 1: 181-193, 2001; Bolden et al., *Anticancer activities of histone deacetylase inhibitors*, Nat Rev Drug Discov, 5: 769-784, 2006; Lindemann et al., *Histone-deacetylase inhibitors for the treatment of cancer*, Cell Cycle, 3: 779-788, 2004; Njar et al., *Retinoids in clinical use*, Med Chem, 2: 431-438, 2006a

[xiii] Marks et al., *Histone deacetylases and cancer, causes and therapies*, Nat Rev Cancer 2001, 1, (3), 194-202

[xiv] Mangelsdorf et al., *The nuclear receptor superfamily, the second decade, Cell* 1995, 83, (6), 835-9

[xv] Patel et al., *Novel retinoic acid metabolism blocking agents endowed with multiple biological activities are efficient growth inhibitors of human breast and prostate cancer cells in vitro and a human breast tumor xenograft in nude mice, J Med Chem* 2004, 47, (27), 6716-29

[xvi] Njar et al., *Retinoic acid metabolism blocking agents (RAMBAs) for treatment of cancer and dermatological diseases, Bioorg Med Chem* 2006, 14, (13), 4323-40

[xvii] Belosay et al., *Effects of novel retinoic acid metabolism blocking agent (VN/14-1) on letrozole-insensitive breast cancer cells, Cancer Res* 2006, 66, (23), 11485-93.; Patel et al., *Novel retinoic acid metabolism blocking agents have potent inhibitory activities on human breast cancer cells and tumour growth, Br J Cancer* 2007, 96, (8), 1204-15

[xviii] Njar, V. C., Nnane, I. P., and Brodie, A. M. Potent inhibition of retinoic acid metabolism enzyme(s) by novel azolyl retinoids. Bioorg Med Chem Lett, 10: 1905-1908, 2000

[xix] Patel, J. B., Huynh, C. K., Handratta, V. D., Gediya, L. K., Brodie, A. M., Goloubeva, O. G., Clement, O. O., Nanne, I. P., Soprano, D. R., and Njar, V. C. Novel retinoic acid metabolism blocking agents endowed with multiple biological activities are efficient growth inhibitors of human breast and prostate cancer cells in vitro and a human breast tumor xenograft in nude mice. J Med Chem, 47: 6716-6729, 2004

[xx] Huynh, C. K., Brodie, A. M., and Njar, V. C. Inhibitory effects of retinoic acid metabolism blocking agents (RAMBAs) on the growth of human prostate cancer cells and LNCaP prostate tumour xenografts in SCID mice. Br J Cancer, 94: 513-523, 2006

[xxi] Patel, J. B., Huynh, C. K., Handratta, V. D., Gediya, L. K., Brodie, A. M., Goloubeva, O. G., Clement, O. O., Nanne, I. P., Soprano, D. R., and Njar, V. C. Novel retinoic acid metabolism blocking agents endowed with multiple biological activities are efficient growth inhibitors of human breast and prostate cancer cells in vitro and a human breast tumor xenograft in nude mice. J Med Chem, 47-6716-6729, 2004

[xxii] Patel, J. B., Mehta, J., Belosay, A. Sabnis, G, Khandelwal, A. Brodie, A. M. Soprano, D. R. and Njar, V. C. Novel retinoic acid metabolism blocking agents have potent inhibitory activities on human breast cancer cells and tumour growth. Br J Cancer, 96: 1204-1215, 2007

[xxiii] Patel, J. B., Mehta, J., Belosay, A., Sabnis, G, Khandelwal, A., Brodie, A. M., Soprano, D. R., and Njar, V. C. Novel retinoic acid metabolism blocking agents have potent inhibitory activities on human breast cancer cells and tumour growth. Br J Cancer, 96: 1204-1215, 2007

[xxiv] Belosay, A., Brodie, A. M., and Njar, V. C. Effects of novel retinoic acid metabolism blocking agent (VN/14-1) on letrozole-insensitive breast cancer cells. Cancer Res, 66: 11485-11493, 2006

[xxv] Huynh, C. K., Brodie, A. M., and Njar, V C Inhibitory effects of retinoic acid metabolism blocking agents (RAMBAs) on the growth of human prostate cancer cells and LNCaP prostate tumour xenografts in SCID mice. Br J Cancer, 94: 513-523, 2006

[xxvi] Patel, J. B., Huynh, C. K., Handratta, V. D., Gediya, L. K., Brodie, A. M., Goloubeva, O. G., Clement, O. O., Nanne, I. P., Soprano, D. R., and Njar, V. C. Novel retinoic acid metabolism blocking agents endowed with multiple biological activities are efficient growth inhibitors of human breast and prostate cancer cells in vitro and a human breast tumor xenograft in nude mice. J Med Chem, 47: 6716-6729, 2004

[xxvii] Patel, J. B., Mehta, J., Belosay, A. Sabnis, G, Khandelwal, A. Brodie, A. M. Soprano, D. R. and Njar, V. C. Novel retinoic acid metabolism blocking agents have potent inhibitory activities on human breast cancer cells and tumour growth. Br J Cancer, 96: 1204-1215, 2007

[xxviii] Njar et al., *Retinoic acid metabolism blocking agents (RAMBAs) for treatment of cancer and dermatological diseases*, Bioorg Med Chem, 14: 4323-4340, 2006

[xxix] Belosay, A., Brodie, A. M., and Njar, V. C. Effects of novel retinoic acid metabolism blocking agent (VN/14-1) on letrozole-insensitive breast cancer cells. Cancer Res, 66: 11485-11493, 2006

[xxx] Huynh, C. K., Brodie, A. M., and Njar, V C Inhibitory effects of retinoic acid metabolism blocking agents (RAMBAs) on the growth of human prostate cancer cells and LNCaP prostate tumour xenografts in SCID mice. Br J Cancer, 94: 513-523, 2006

[xxxi] Patel, J. B., Huynh, C. K., Handratta, V. D., Gediya, L. K., Brodie, A. M., Goloubeva, O. G., Clement, O. O., Nanne, I. P., Soprano, D. R., and Njar, V. C. Novel retinoic acid metabolism blocking agents endowed with multiple biological activities are efficient growth inhibitors of human breast and prostate cancer cells in vitro and a human breast tumor xenograft in nude mice. J Med Chem, 47-6716-6729, 2004

[xxxii] Patel, J. B., Mehta, J., Belosay, A. Sabnis, G, Khandelwal, A. Brodie, A. M. Soprano, D. R. and Njar, V. C. Novel retinoic acid metabolism blocking agents have potent inhibitory activities on human breast cancer cells and tumour growth. Br J Cancer, 96: 1204-1215, 2007

[xxxiii] Mehta, R. R., Hawthorne, M. E., Graves, J. M., and Mehta, R. G. Metabolism of N-[4-hydroxyphenyl]retinamide (4-HPR) to N-[4-methoxyphenyl]retinamide (4-MPR) may serve as a biomarker for its efficacy against human breast cancer and melanoma cells. Eur J Cancer, 34: 902-907, 1998

[xxxiv] Silverman, R. B. The organic chemistry of drug design and drug action, p. 1-422. San Diego: Academic Press, 1992

[xxxv] Bubert, C., Leese, M. P., Mahon, M. F., Ferrandis, E., Regis-Lydi, S., Kasprzyk, P. G., Newman, S. P., Ho, Y. T., Purohit, A., Reed, M. J., and Potter, B. V. 3,17-Disubstituted 2-Alkylestra-1,3,5(10)-trien-3-ol Derivatives: Synthesis, In Vitro and In Vivo Anticancer Activity. J Med Chem, 50: 4431-4443, 2007

[xxxvi] Leese, M. P., Hejaz, H. A. Mahon, M. F. Newman, S. P. Purohit, A. Reed, M. J. and Potter, B. V. A-ring-substituted estrogen-3-O-sulfamates: potent multitargeted anticancer agents. J Med Chem, 48: 5243-5256, 2005

[xxxvii] Leese, M. P. Leblond, B. Smith, A. Newman, S. P. Di Fiore, A. De Simone, G. Supuran, C. T., Purohit, A., Reed, M. J., and Potter, B. V. 2-substituted estradiol bis-sulfamates, multitargeted antitumor agents: synthesis, in vitro SAR, protein crystallography, and in vivo activity. J Med Chem, 49: 7683-7696, 2006

[xxxviii] Day, J. M. Newman, S. P. Comninos, A. Solomon, C. Purohit, A. Leese, M. P. Potter, B. V. and Reed, M. J. The effects of 2-substituted oestrogen sulphamates on the growth of prostate and ovarian cancer cells. J Steroid Biochem Mol Biol, 84: 317-325, 2003

[xxxix] Stanway, S. J. Purohit, A. Woo, L. W. Sufi, S. Vigushin, D. Ward, R. Wilson, R. H. Stanczyk, F. Z., Dobbs, N., Kulinskaya, E., Elliott, M., Potter, B. V., Reed, M. J., and Coombes, R. C. Phase I study of STX 64 (667 Coumate) in breast cancer patients: the first study of a steroid sulfatase inhibitor. Clin Cancer Res, 12: 1585-1592, 2006

[xl] Woo, L. W., Bubert, C., Sutcliffe, O. B., Smith, A., Chander, S. K., Mahon, M. F., Purohit, A., Reed, M. J., and Potter, B. V. Dual aromatase-steroid sulfatase inhibitors. J Med Chem, 50: 3540-3560, 2007

[xli] Chapman, T. Drug discovery: the leading edge. Nature, 430: 109-115, 2004

[xlii] Hoffmann, M., Chrzanowska, M., Hermann, T., and Rychlewski, J. Modeling of purine derivatives transport across cell membranes based on their partition coefficient determination and quantum chemical calculations. J Med Chem, 48: 4482-4486, 2005

[xliii] Johnson, S. A. and Thomas, W. Therapeutic potential of purine analogue combinations in the treatment of lymphoid malignancies. Hematol Oncol, 18: 141-153, 2000

[xliv] Legraverend, M. and Grierson, D. S. The purines: potent and versatile small molecule inhibitors and modulators of key biological targets. Bioorg Med Chem, 14: 3987-4006, 2006

[xlv] de Koning, H. and Diallinas, G. Nucleobase transporters (review). Mol Membr Biol, 17: 75-94, 2000

[xlvi] Patel, J. B., Huynh, C. K. Handratta, V. D. Gediya, L. K. Brodie, A. M. Goloubeva, O. G. Clement, O. O., Nanne, I. P., Soprano, D. R., and Njar, V. C. Novel retinoic acid metabolism blocking agents endowed with multiple biological activities are efficient growth inhibitors of human breast and prostate cancer cells in vitro and a human breast tumor xenograft in nude mice. J Med Chem, 47-6716-6729, 2004

[xlvii] Belosay, A., Brodie, A. M., and Njar, V. C. Effects of novel retinoic acid metabolism blocking agent (VN/14-1) on letrozole-insensitive breast cancer cells. Cancer Res, 66: 11485-11493, 2006

[xlviii] Huynh, C. K., Brodie, A. M., and Njar, V C Inhibitory effects of retinoic acid metabolism blocking agents (RAMBAs) on the growth of human prostate cancer cells and LNCaP prostate tumour xenografts in SCID mice. Br J Cancer, 94: 513-523, 2006

[xlix] Patel, J. B., Huynh, C. K. Handratta, V. D. Gediya, L. K. Brodie, A. M. Goloubeva, O. G. Clement, O. O., Nanne, I. P., Soprano, D. R., and Njar, V. C. Novel retinoic acid metabolism blocking agents endowed with multiple biological activities are efficient growth inhibitors of human breast and prostate cancer cells in vitro and a human breast tumor xenograft in nude mice. J Med Chem, 47: 6716-6729, 2004

[l] Patel, J. B., Mehta, J., Belosay, A., Sabnis, G, Khandelwal, A., Brodie, A. M., Soprano, D. R., and Njar, V. C. Novel retinoic acid metabolism blocking agents have potent inhibitory activities on human breast cancer cells and tumour growth. Br J Cancer, 96: 1204-1215, 2007

[ii] Gediya, L. K., Chopra, P., Purushottamachar, P., Maheshwari, N., and Njar, V. C. A new simple and high-yield synthesis of suberoylanilide hydroxamic acid and its inhibitory effect alone or in combination with retinoids on proliferation of human prostate cancer cells. J Med Chem, 48: 5047-5051, 2005

[iii] Gediya, L. Belosay, A, Khandelwal, A. Purushottamachar, P. Njar, V. C. O. Improved synthesis of histone deacetylase inhibitors (HDACIs) (MS-275 and CI-994) and inhibitory effects of HDACIs alone and in combination with RAMBAs or retinoids on growth of human LNCaP prostate cancer cells and tumor xenografts. Submitted to J. Med. Chem., 2007

[iiii] Khandelwal, A., Gediya, L. K., Njar, V. C. O, Synergistic effects of MS-275 and VN/66-1 in a hormone-refractory prostate cancer model. Submitted to Cancer Research, 2007

[liv] Leese, M. P., Hejaz, H. A. Mahon, M. F. Newman, S. P. Purohit, A. Reed, M. J. and Potter, B. V. A-ring-substituted estrogen-3-O-sulfamates: potent multitargeted anticancer agents. J Med Chem, 48: 5243-5256, 2005

[lv] Leese, M. P., Leblond, B., Smith, A., Newman, S. P., Di Fiore, A., De Simone, G., Supuran, C. T., Purohit, A., Reed, M. J., and Potter, B. V. 2-substituted estradiol bis-sulfamates, multitargeted antitumor agents: synthesis, in vitro SAR, protein crystallography, and in vivo activity. J Med Chem, 49: 7683-7696, 2006

[lvi] Leese, M. P. Leblond, B. Smith, A. Newman, S. P. Di Fiore, A. De Simone, G. Supuran, C. T., Purohit, A., Reed, M. J., and Potter, B. V. 2-substituted estradiol bis-sulfamates, multitargeted antitumor agents: synthesis, in vitro SAR, protein crystallography, and in vivo activity. J Med Chem, 49: 7683-7696, 2006

[lvii] Frickel, F.-F., Nuerrenbach, A. Amides of retinoic acid with 5-amino tetrazole. USA, 1984

[lviii] Boenoist, E., Loussouarn, A., Remaud, P., Chatal, J., Gestine, J. Convinient and simplified approaches to N-mom-protected triaminepropane derivatives: Key intermediates for bifunctional chelating agent. Synthesis: 1113-1118, 1998

[lix] Yang, J. Dan Q. Q., Liu, J. Wei, Z. Wu, J. and Bai, X. Preparation of a fully substituted purine library. J Comb Chem, 7: 474-482, 2005

[lx] Njar, V. C Nnane, I. P. and Brodie, A. M. Potent inhibition of retinoic acid metabolism enzyme(s) by novel azolyl retinoids. Bioorg Med Chem Lett, 10: 1905-1908, 2000

[lxi] Patel, J. B., Huynh, C. K. Handratta, V. D. Gediya, L. K., Brodie, A. M. Goloubeva, O. G., Clement, O. O., Nanne, I. P., Soprano, D. R., and Njar, V. C. Novel retinoic acid metabolism blocking agents endowed with multiple biological activities are efficient growth inhibitors of human breast and prostate cancer cells in vitro and a human breast tumor xenograft in nude mice. J Med Chem, 47: 6716-6729, 2004

[lxii] Learmonth, D. A. Method for preparation of (S)-(+) and (R)-(−)10,11-dihydro-10-hydroxy-5H-dibenz/B,F/azephine-5-carboxamide. USA: Portela & C.A., S. A., 2006

[lxiii] Njar, V. C Nnane, I. P. and Brodie, A. M. Potent inhibition of retinoic acid metabolism enzyme(s) by novel azolyl retinoids. Bioorg Med Chem Lett, 10: 1905-1908, 2000

[lxiv] Patel, J. B., Huynh, C. K. Handratta, V. D. Gediya, L. K. Brodie, A. M. Goloubeva, O. G. Clement, O. O., Nanne, I. P., Soprano, D. R., and Njar, V. C. Novel retinoic acid metabolism blocking agents endowed with multiple biological activities are efficient growth inhibitors of human breast and prostate cancer cells in vitro and a human breast tumor xenograft in nude mice. J Med Chem, 47: 6716-6729, 2004

[lxv] O'Neill, P. M., Rawe, S. L., Borstnik, K., Miller, A., Ward, S. A., Bray, P. G., Davies, J., Oh, C. H., and Posner, G. H. Enantiomeric 1,2,4-trioxanes display equivalent in vitro antimalarial activity versus *Plasmodium falciparum* malaria parasites: implications for the molecular mechanism of action of the artemisinins Chembiochem, 6: 2048-2054, 2005

[lxvi] Njar, V. C., Nnane, I. P., and Brodie, A. M. Potent inhibition of retinoic acid metabolism enzyme(s) by novel azolyl retinoids. Bioorg Med Chem Lett, 10: 1905-1908, 2000

[lxvii] Patel, J. B., Huynh, C. K. Handratta, V. D. Gediya, L. K. Brodie, A. M. Goloubeva, O. G. Clement, O. O., Nanne, I. P., Soprano, D. R., and Njar, V. C. Novel retinoic acid metabolism blocking agents endowed with multiple biological activities are efficient growth inhibitors of human breast and prostate cancer cells in vitro and a human breast tumor xenograft in nude mice. J Med Chem, 47: 6716-6729, 2004

[lxviii] Njar, V. C. O. High-yield synthesis of novel imidazoles and triazoles from alocohols and phenols. Synthesis, 14: 2019-2028, 2000

[lxix] Totleben, M. J., Freeman, J. P., and Szmuszkovicz, J. Imidazole Transfer from 1,1'-Carbonyldimidazole and 1,1'-(Thiocarbonyl)diimidazole to Alcohols. A New Protocol for the Conversion of Alcohols to Alkylheterocycles. J Org Chem, 62: 7319-7323, 1997

[lxx] Dominguez, M., Alvarez, R., Borras, E., Farres, J., Pares, X., and de Lera, A. R. Synthesis of enantiopure C3- and C4-hydroxyretinals and their enzymatic reduction by ADH8 from *Xenopus laevis*. Org Biomol Chem, 4: 155-164, 2006

[lxxi] Tiecco, M. Testaferri, L. Santi, C. Tomassini, C. Bonini, R. Marini, F. Bagnoli, L., and Temperini, A. A chiral electrophilic selenium reagent to promote the kinetic resolution of racemic allylic alcohols. Org Lett, 6: 4751-4753, 2004

[lxxii] Yadav, J. S., Reddy, B. V. S., Reddy, K. S. Ultrasound-accelerated synthesis of chiral allylic alcohols promoted by indium metal. Tetrahedron, 59: 55333-55336, 2003

[lxxiii] Kamal, A., Sandbhor, M., Shaik, A., Sravanthi, V. One-pot synthesis and resolution of chiral allylic alcohols. Tetrehedron Asymmetry, 14: 2839-2844, 2003

[lxxiv] Vedejs, E. and MacKay, J. A. Kinetic resolution of allylic alcohols using a chiral phosphine catalyst. Org Lett, 3: 535-536, 2001

[lxxv] Dominguez, M., Alvarez, R., Borras, E., Farres, J., Pares, X., and de Lera, A. R. Synthesis of enantiopure C3- and C4-hydroxyretinals and their enzymatic reduction by ADH8 from *Xenopus laevis*. Org Biomol Chem, 4: 155-164, 2006

[lxxvi] Fujima, Y. Ikunaka, M. Inoue, T. Matsumoto, J. Synthesis of (S)-3-(N-methylamino)-1-(2-thienyl)propan-1-ol: Revisiting Eli Lilly's resolution-racemization-recycle synthesis of duloxetine for its robust processes. Org. Process Res. Dev., 10: 905-913, 2006

[lxxvii] Fujima, Y. Ikunaka, M. Inoue, T. Matsumoto, J. Synthesis of (S)-3-(N-methylamino)-1-(2-thienyl)propan-1-ol: Revisiting Eli Lilly's resolution-racemization-recycle synthesis of duloxetine for its robust processes. Org. Process Res. Dev., 10: 905-913, 2006

[lxxviii] Frye, S. V. Haffner, C. D. Maloney, P. R. Hiner, R. N. Dorsey, G. F. Noe, R. A. Unwalla, R. J. Batchelor, K. W., Bramson, H. N., Stuart, J. D., and et al. Structure-activity relationships for inhibition of type 1 and 2 human 5 alpha-reductase and human adrenal 3 beta-hydroxy-delta 5-steroid dehydrogenase/3-keto-delta 5-steroid isomerase by 6-azaandrost-4-en-3-ones: optimization of the C17 substituent. J Med Chem, 38: 2621-2627, 1995

[lxxix]Curley, R. W., Mershon, S. M. Solid phase synthesis of arylretinamides. U.S. Pat. No. 6,696,606 B2: The Ohio State University Research Foundation, 2004

[lxxx]Huynh, C. K., Brodie, A. M., and Njar, V. C. Inhibitory effects of retinoic acid metabolism blocking agents (RAMBAs) on the growth of human prostate cancer cells and LNCaP prostate tumour xenografts in SCID mice. Br J Cancer, 94: 513-523, 2006

[lxxxi]Patel, J. B., Huynh, C. K. Handratta, V. D. Gediya, L. K. Brodie, A. M. Goloubeva, O. G. Clement, O. O., Nanne, I. P., Soprano, D. R., and Njar, V. C. Novel retinoic acid metabolism blocking agents endowed with multiple biological activities are efficient growth inhibitors of human breast and prostate cancer cells in vitro and a human breast tumor xenograft in nude mice. J Med Chem, 47: 6716-6729, 2004

[lxxxii]Patel, J. B., Mehta, J., Belosay, A. Sabnis, G, Khandelwal, A. Brodie, A. M. Soprano, D. R. and Njar, V. C. Novel retinoic acid metabolism blocking agents have potent inhibitory activities on human breast cancer cells and tumour growth. Br J Cancer, 96: 1204-1215, 2007

[lxxxiii]Belosay, A. Jelovac, D. Long, B. Njar, V. C. O., Brodie, A. Histone deacetylase inhibitors synergize with retinoic acid metabolism blocking agent (VN/14-1) in letrozole resistant human breast cancer cells. In The Endocrine Society's 88th Annual Meeting, Boston, Mass., USA, Jun. 24-27, 2006

[lxxxiv]Gediya, L. K. Chopra, P. Purushottamachar, P. Maheshwari, N. and Njar, V. C. A new simple and high-yield synthesis of suberoylanilide hydroxamic acid and its inhibitory effect alone or in combination with retinoids on proliferation of human prostate cancer cells. J Med Chem, 48: 5047-5051, 2005

We claim:

1. A compound of structural formulae 2A, 3A, 3B, 4B, 4C or 5:

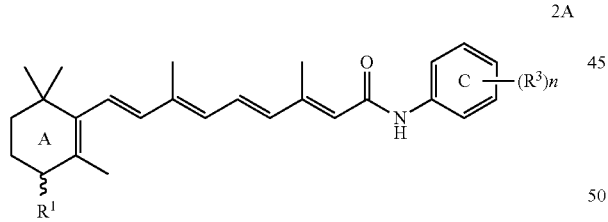

2A where $R^1$ is
a thirane group,
a —SH group,
an -alkyl-SH group,
—$OR^4$, where $R^4$ is hydrogen or alkyl,
a cyclopropyl ether,
an oxirane group formed together with the 4-position carbon,
—$NR_5R_6$, where $R_5$ and $R_6$ are independently selected from the group consisting of hydrogen and alkyl groups, or $R_5$ and $R_6$ may together form an imidazolyl ring or a triazole ring,
a pyridyl group, an ethinyl group, a cyclopropyl-amino group, a cyano group, an azido group, an allylic azole group, or an 1H-imidazole group, or $R^1$ forms, together with the C-4 carbon atom, an oxime, or aziridine group;

each $R^3$ is independent and is selected from a halogen group, a cyano group, a —SH group, and an alkyl group substituted with at least one of a halogen group, a cyano group, or a —SH group; and n is from 0 to 5;

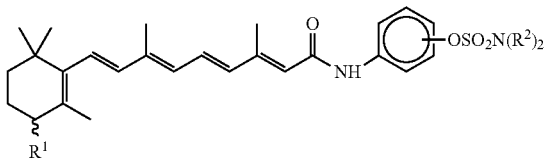

3A where $R^1$ is the same as in Formula 2A above; and
each $R^2$ is independent and is a hydrogen or an alkyl group;

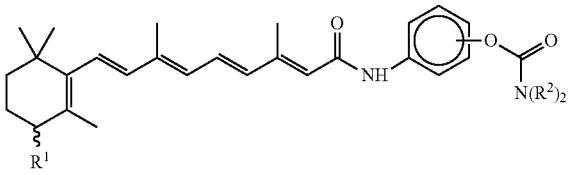

3B where $R^1$ and $R^2$ are the same as in Formula 3A above;

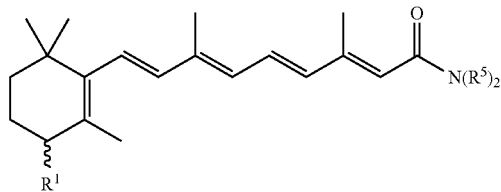

4B where $R^1$ is the same as in Formula 2A above; and
each $R^5$ is independently selected from a hydrogen atom, an unsubstituted alkyl group, and a ring containing a nitrogen atom, where the ring containing a nitrogen atom is selected from an azine ring, a triazine ring, an azirene ring, an azete ring, an diazetidine ring, an azole ring, a triazole ring, a tetrazole ring, an imidazole ring, an azocane ring, a pyridine ring, piperidine ring, or a purine ring;

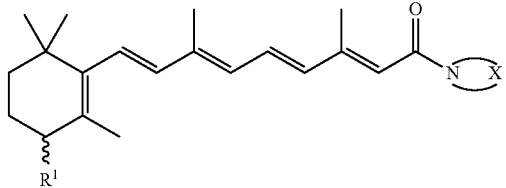

4C where $R^1$ is the same as in Formula 2A above
and
X forms, together with the nitrogen atom, an azine ring, a triazine group, an azirine group, an azete group, an diazetidine group, an azocane group, a pyridine group, piperidine group, benzimidazole group, or a purine group;

Formula 5:

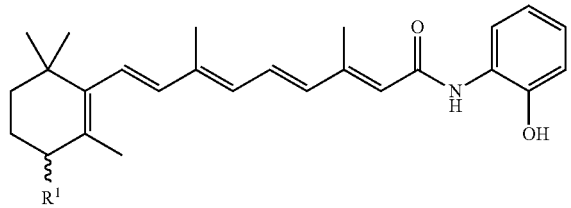

where R¹ is the same as in Formula 2A above.

2. The compound of claim 1 wherein the structural formula is formula 2A':

2A'

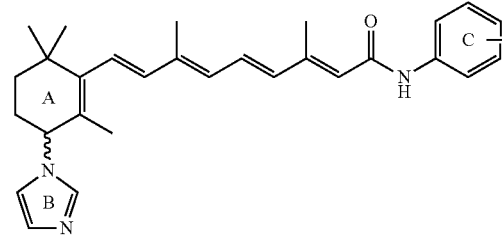

where each R³ and n are the same as in Formula 2A.

3. The compound of claim 2 wherein the structural formula is formula VNLG/146, VNLG/153, or Compounds 4-33:

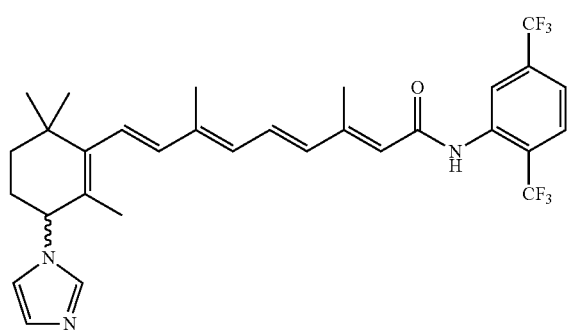

VNLG/146

VNLG/153

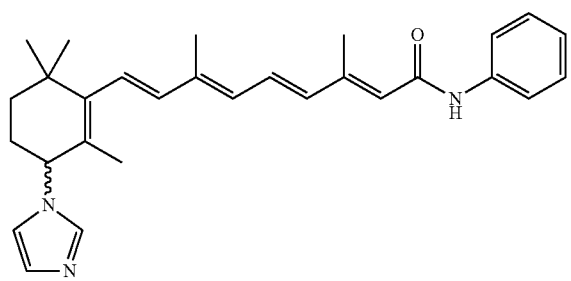

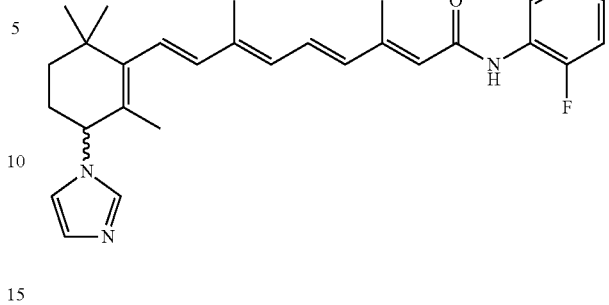

4

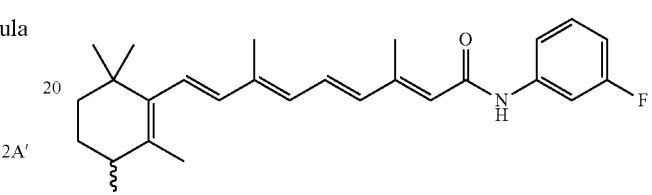

5

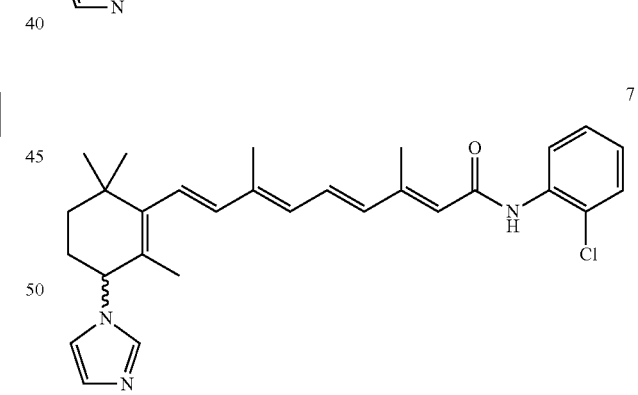

6

7

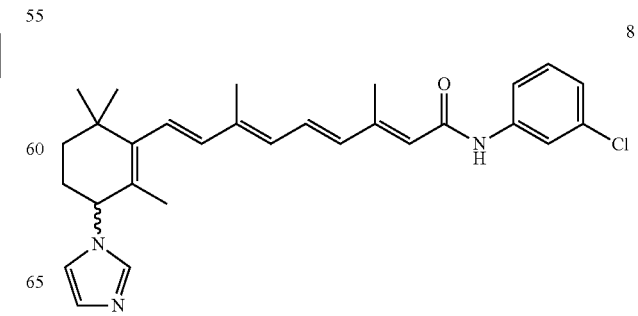

8

9
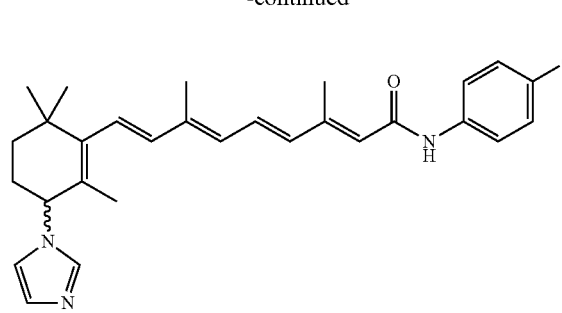
10
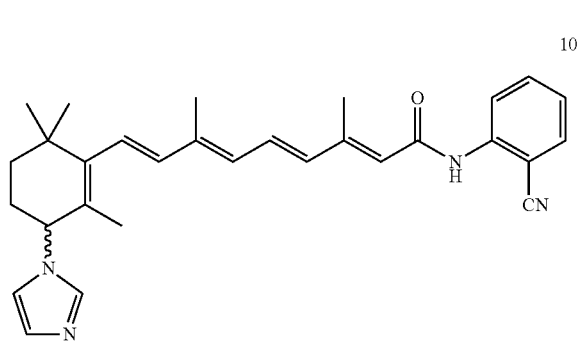
11
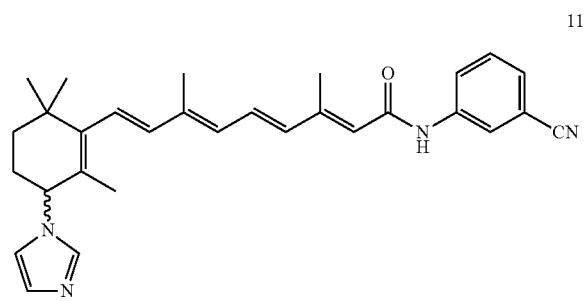
12
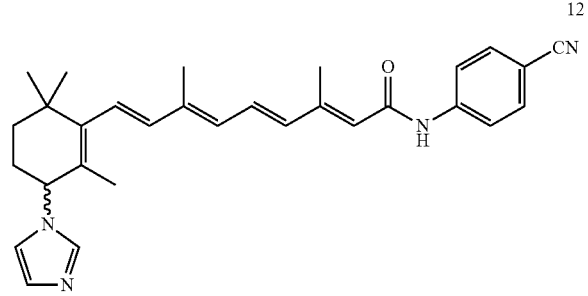
13
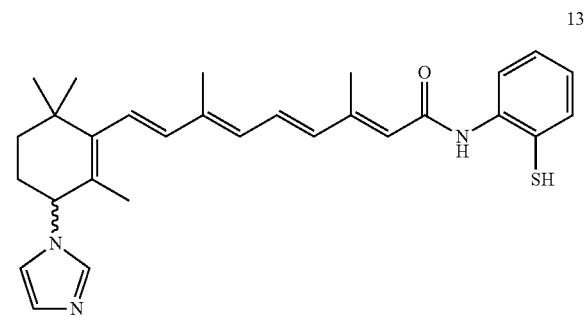
14
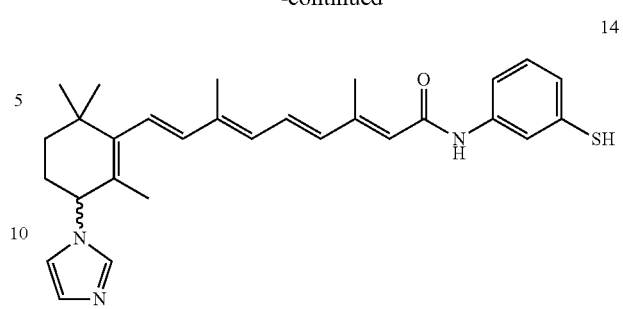
15
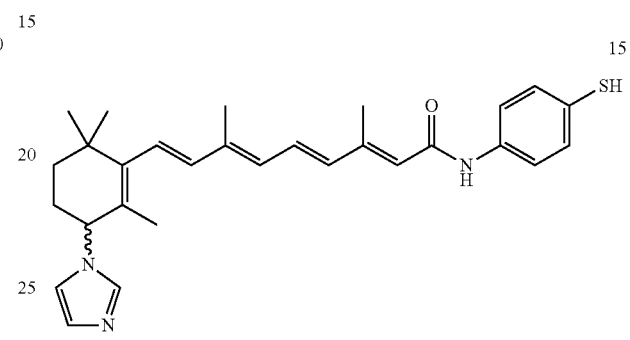
16
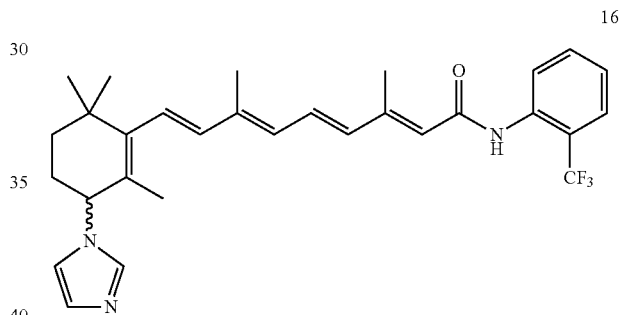
17
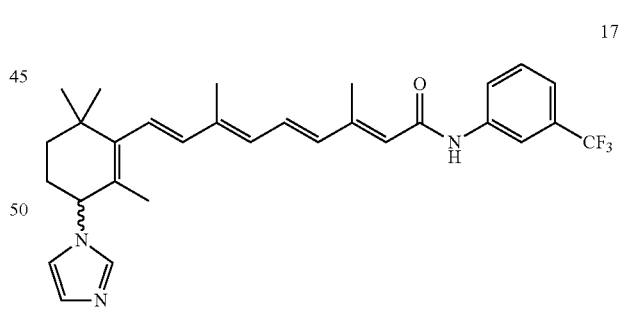
18
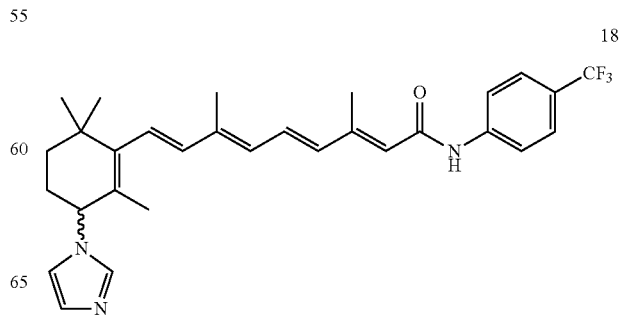

19
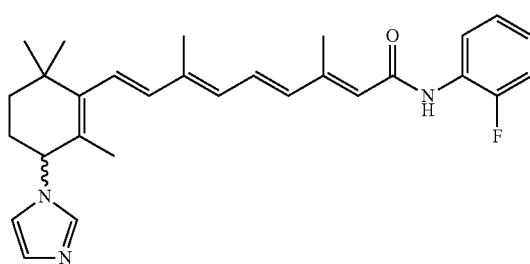
20
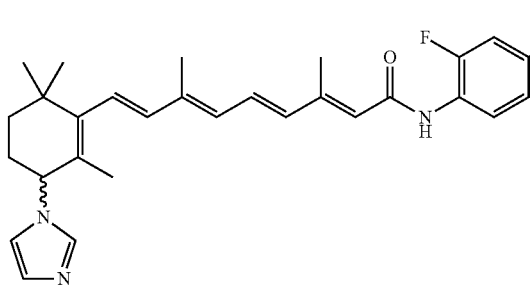
21
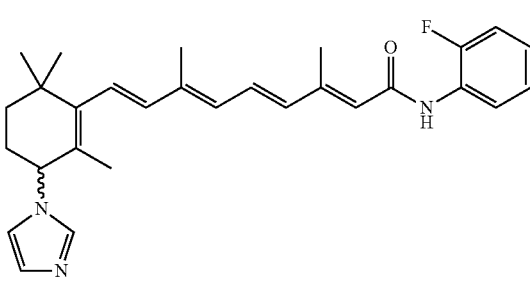
22
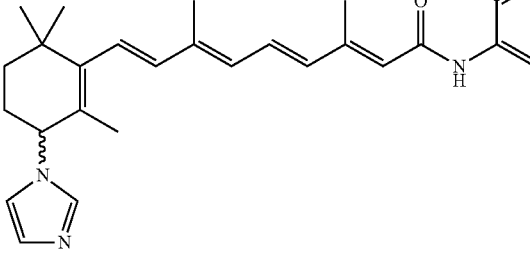
23
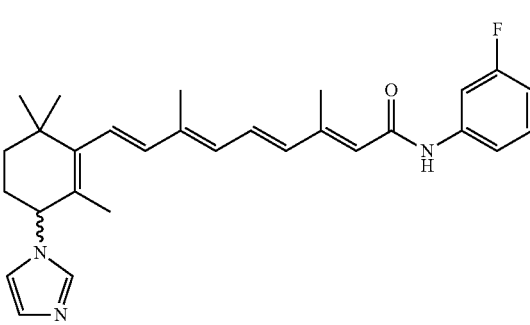
24
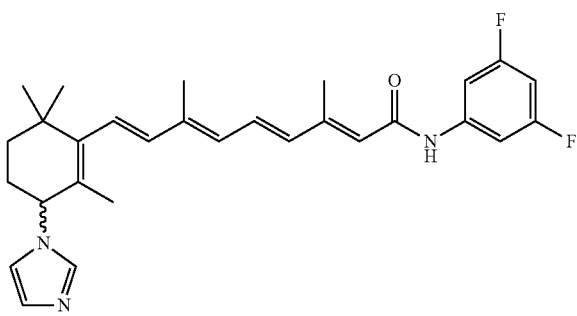
25
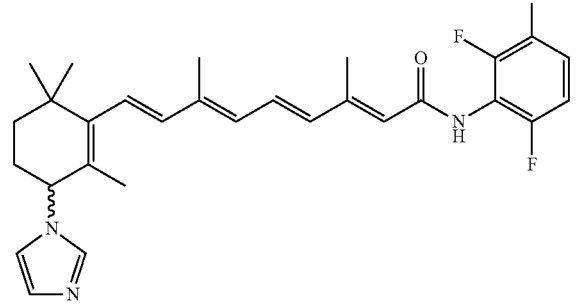
26
27
28
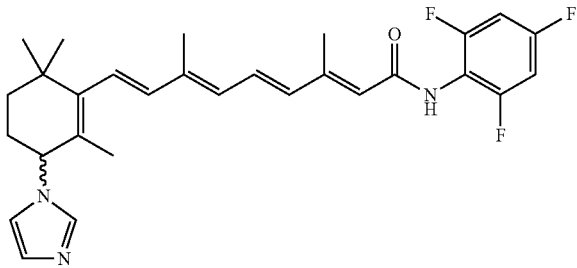

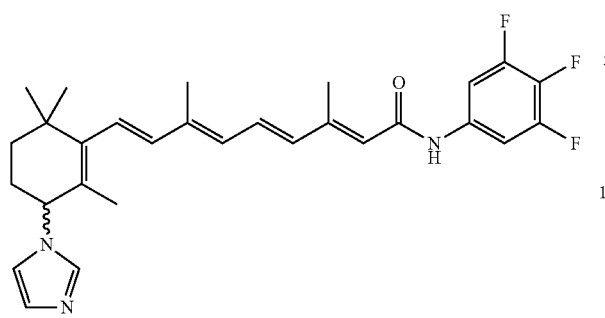
29
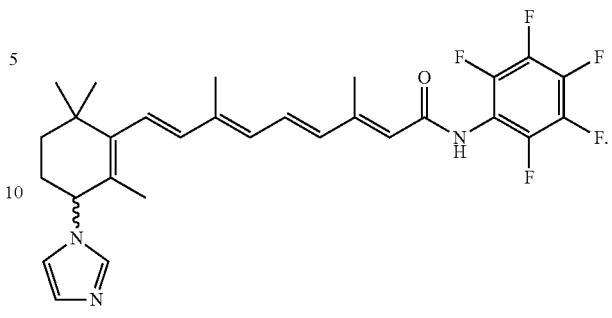
33
4. The compound of claim 1 wherein the structural formula is selected from one of Formulae 3A', 3B', 3A" or 3B":
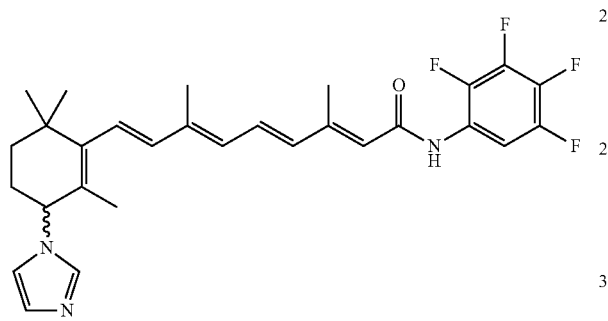
30
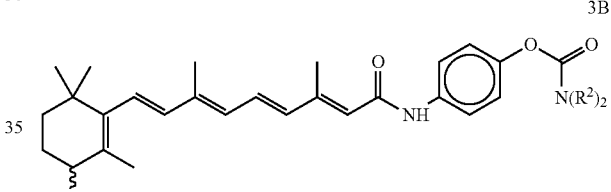
3A'
where $R^1$ and $R^2$ are the same as in Formula 3A;
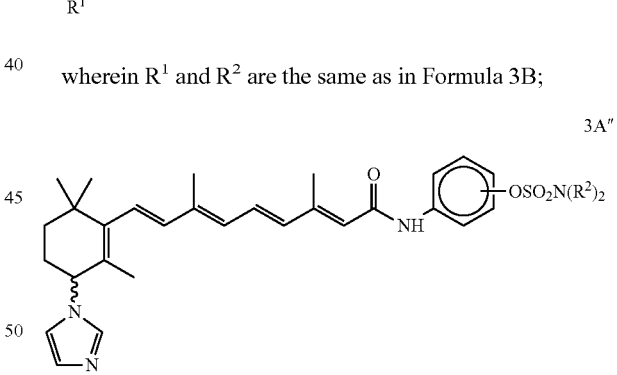
3B'
wherein $R^1$ and $R^2$ are the same as in Formula 3B;
3A"
wherein each $R^2$ is the same as in formula 3A;
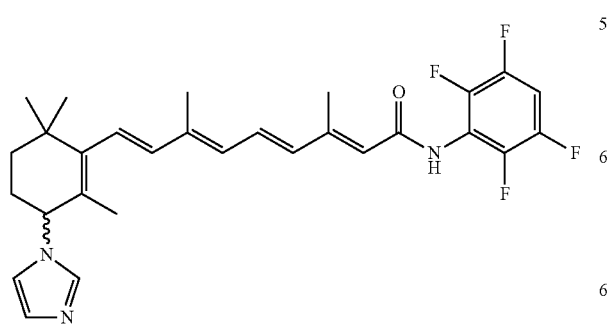
32
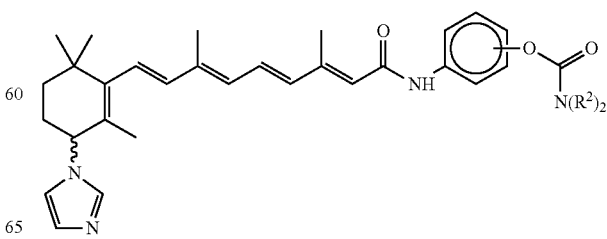
3B"
wherein each $R^2$ is the same as in formula 3B.

5. The compound of claim 4 wherein the structural formula is Formula 34 or 35:

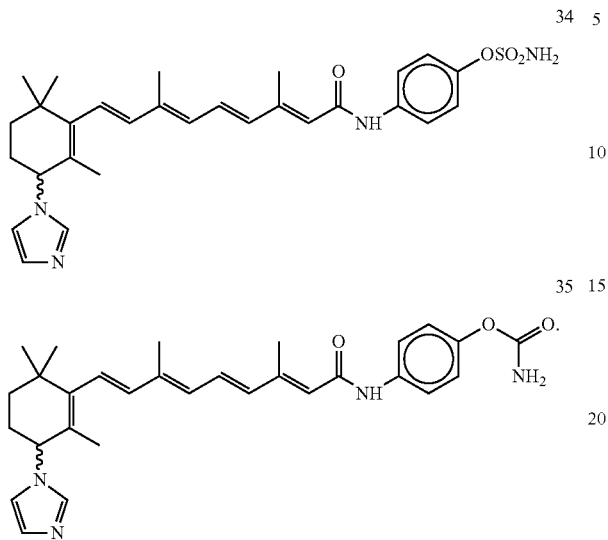

6. A compound having of the structural Formula 4A, 4B' or 4C':

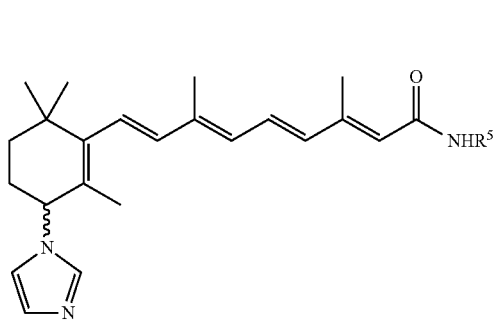

where R⁵ is selected from a hydrogen atom, an alkyl group, and a ring containing a nitrogen atom, where the ring containing a nitrogen atom is selected from an azine ring, a triazine group, an azirene group, an azete group, an diazetidine group, an azole group, a triazole group, a tetrazole group, an imidazole group, an azocane group, a pyridine group, piperidine group, benzimidazole group, or a purine group;

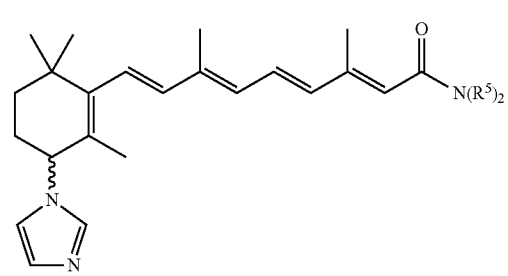

where each R⁵ is independently selected from a hydrogen atom, an alkyl group, and a ring containing a nitrogen atom, where the ring containing a nitrogen atom is selected from an azine ring, a triazine group, an azirene group, an azete group, an diazetidine group, an azole group, a triazole group, a tetrazole group, an imidazole group, an azocane group, a pyridine group, piperidine group, benzimidazole group, or a purine group;

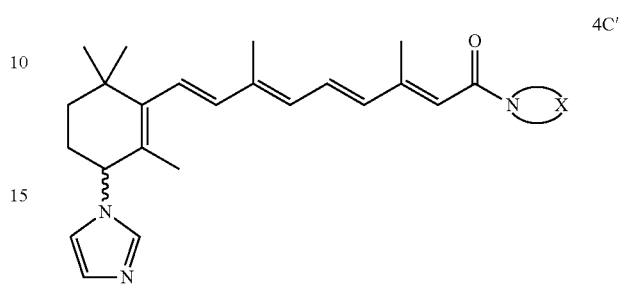

where X forms, together with the nitrogen atom, an azine ring, a triazine group, an azirine group, an azete group, an diazetidine group, an azocane group, a pyridine group, piperidine group, benzimidazole group, or a purine group.

7. A compound of the structural Formula 36-38, 39B-C, 40B-C, 41B-C, 42B-C, 43B-C, 44B-C, 45B, 45D, 46B-E, 47B-E, 48B-E, VNLG/148 or VNLG/145:

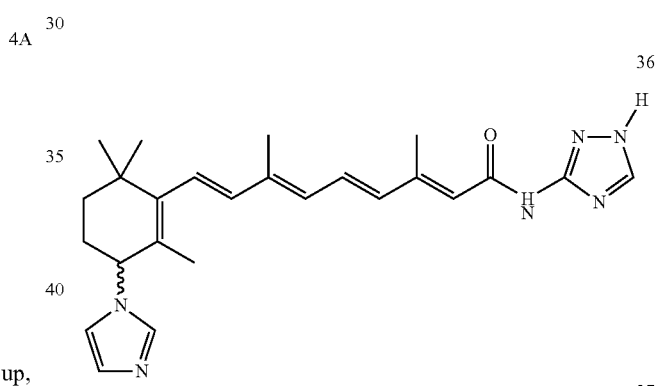

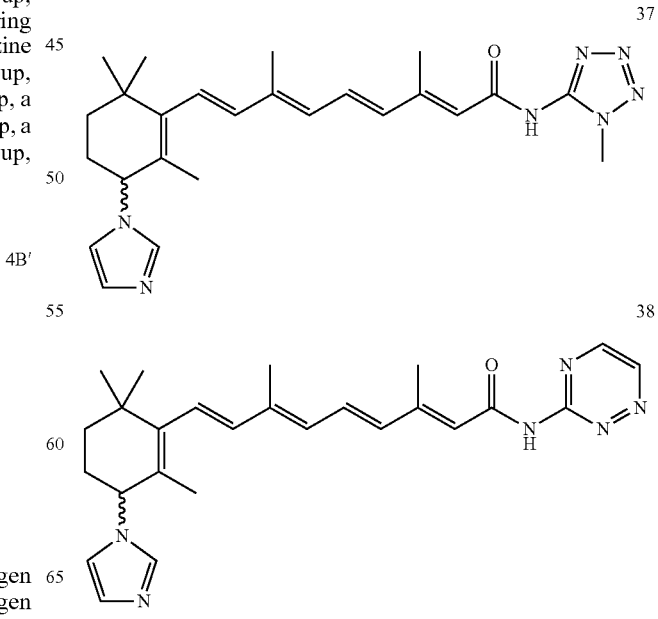

39B
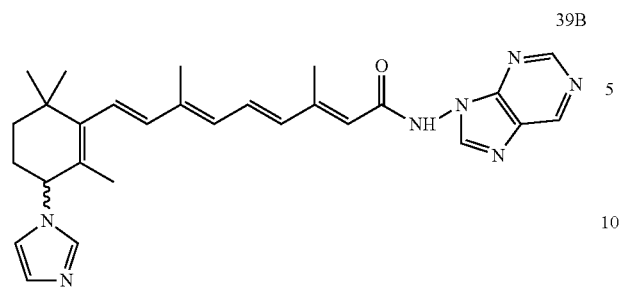
39C
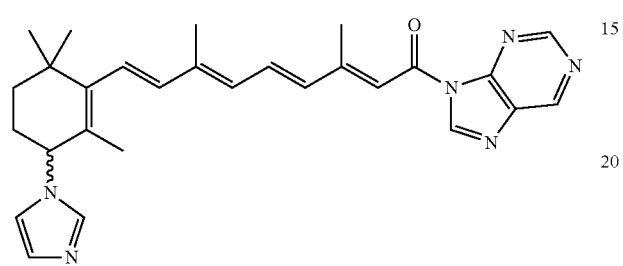
40B
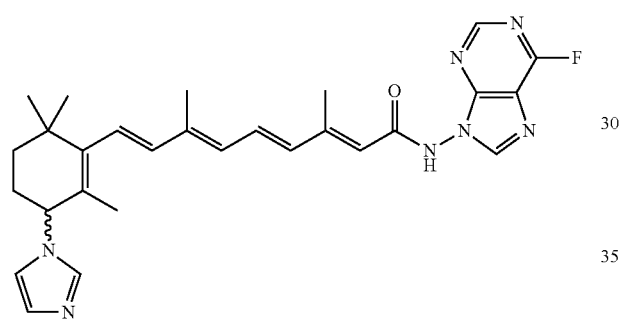
40C
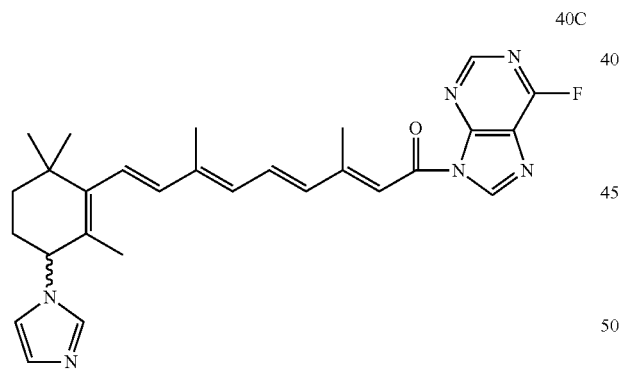
41B
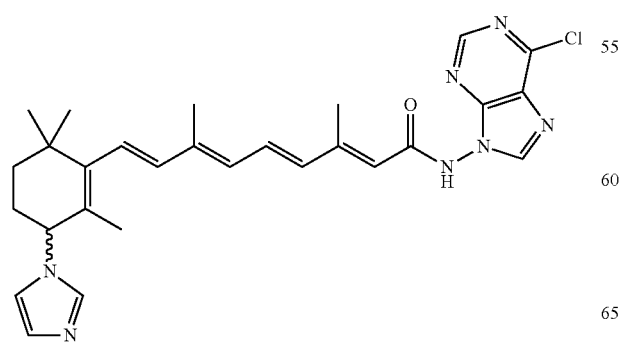
41C
42B
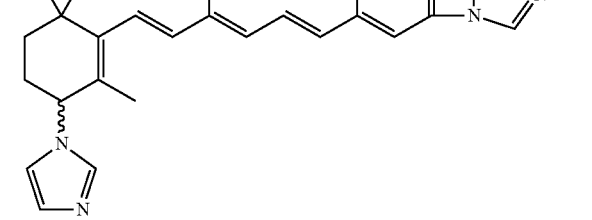
42C
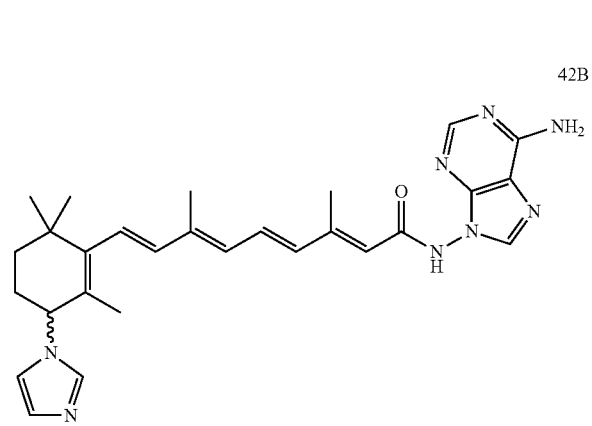
43B
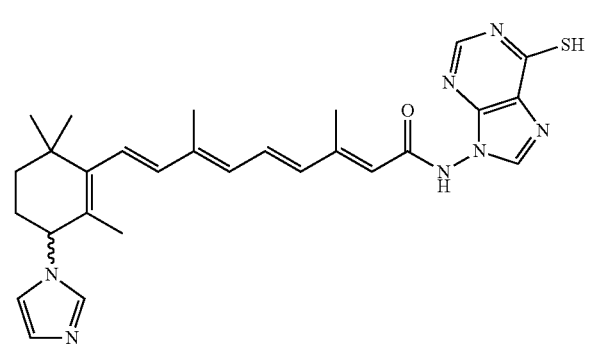
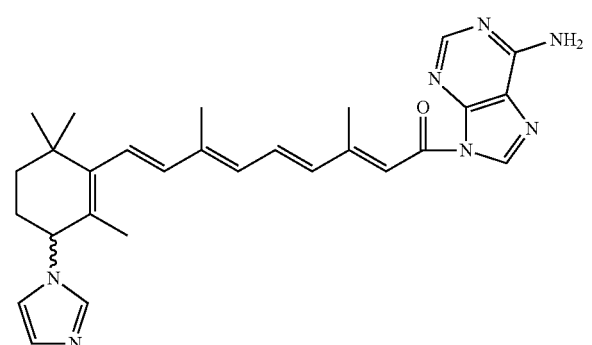

43C
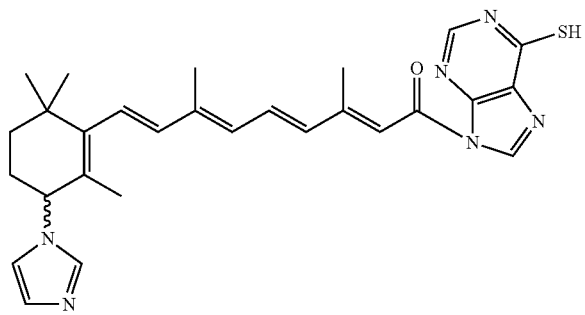
45D
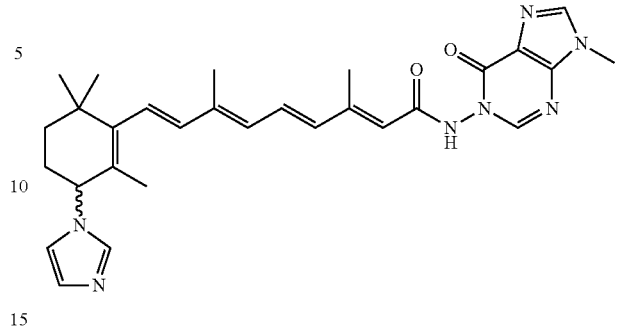
44B
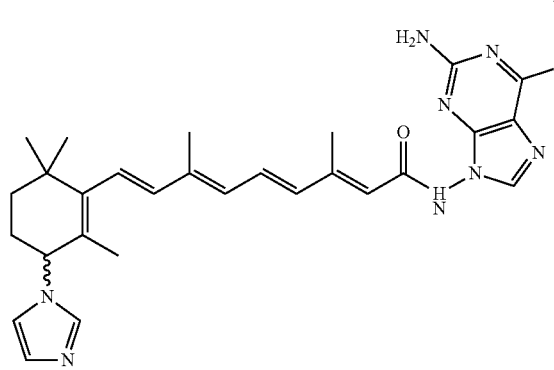
46B
44C
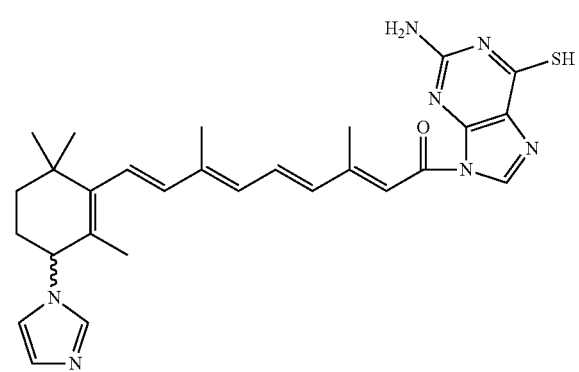
46C
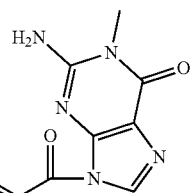
45B
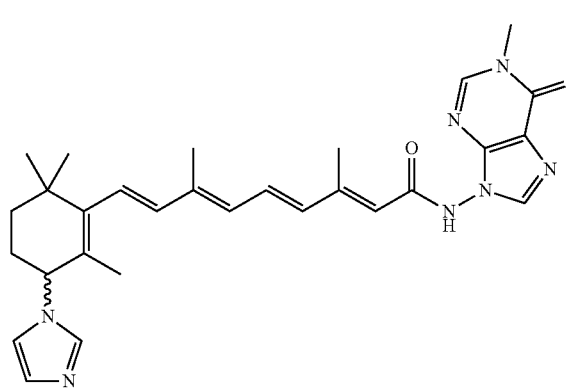
46D
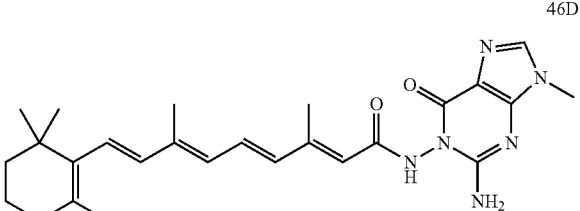

46E
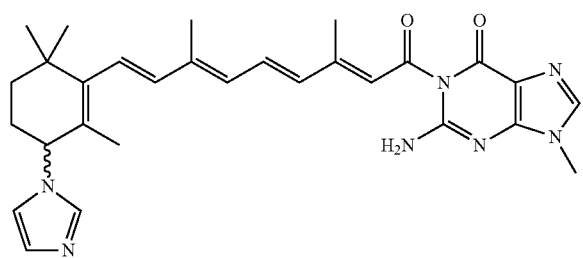
47D
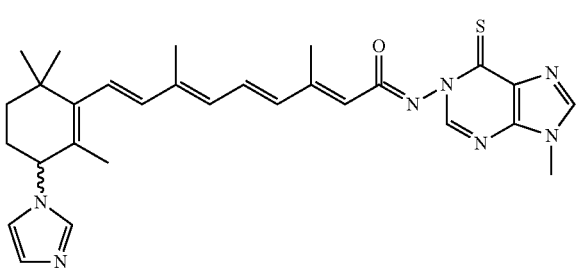
47B
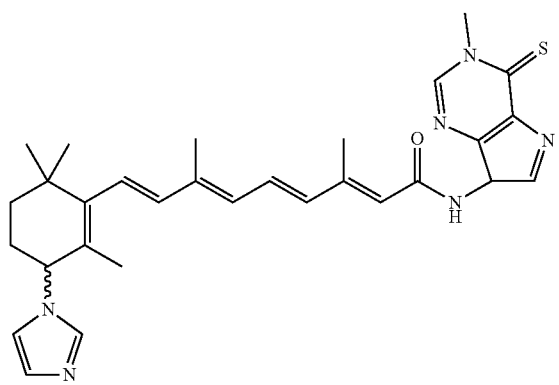
47E
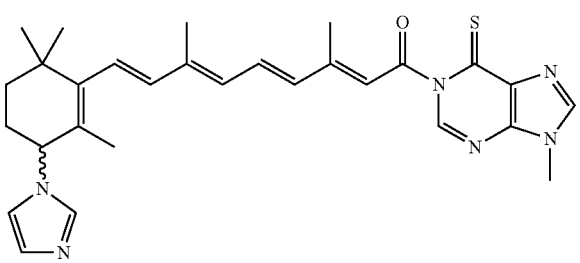
47C
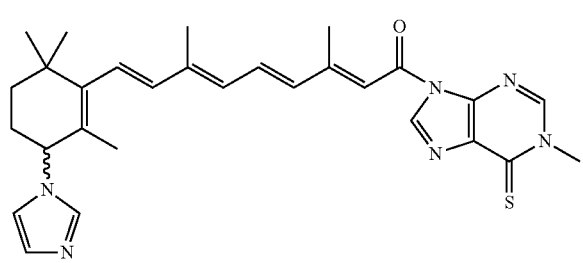
48D
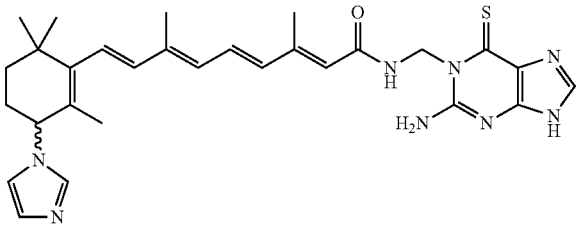
48B
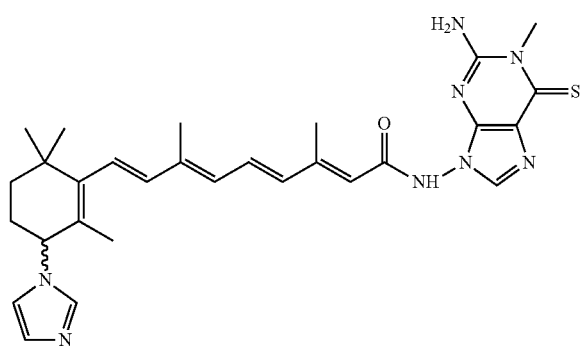
48E
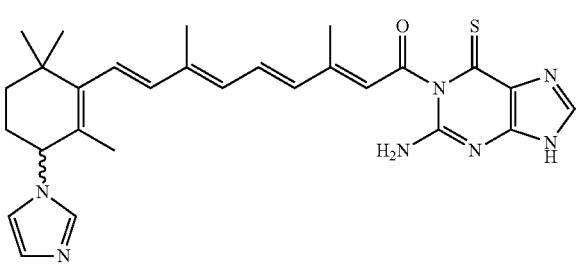
48C
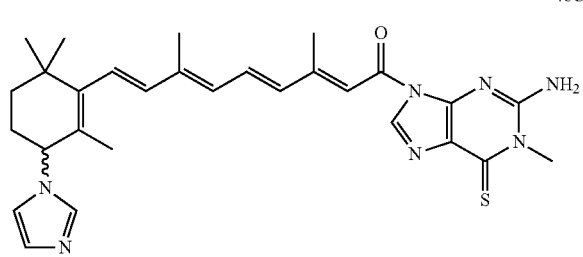
VNLG/145
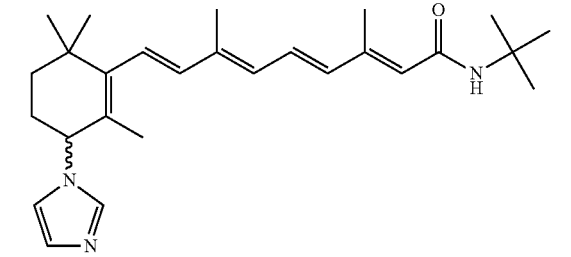

-continued

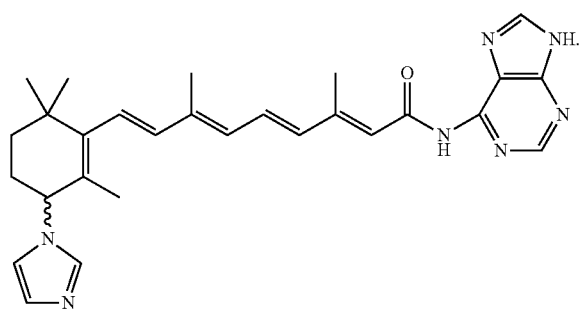
VNLG/148

8. The compound of claim 1 wherein the structural formula is Formula VNLG/152, Formula VNLG/153 or VNLG 146:

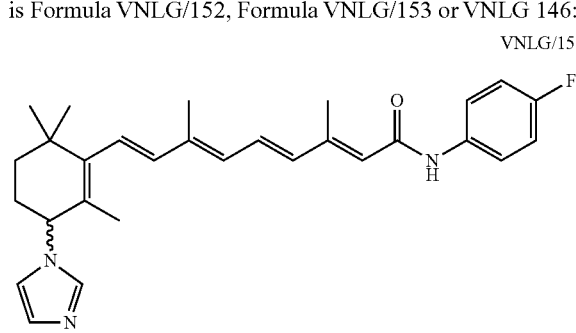
VNLG/152

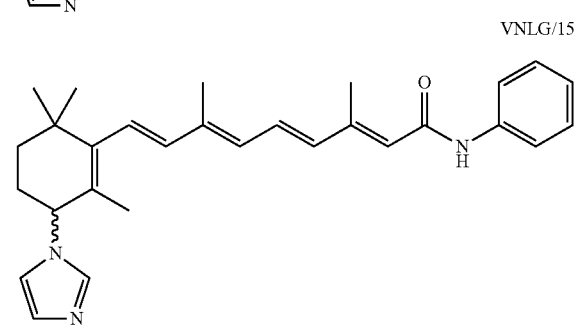
VNLG/153

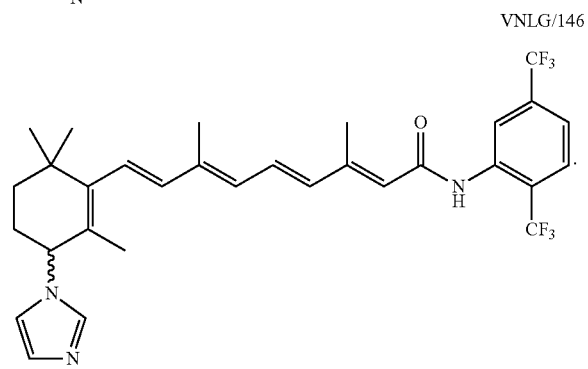
VNLG/146

9. The compound of claim 1, wherein the compound is:

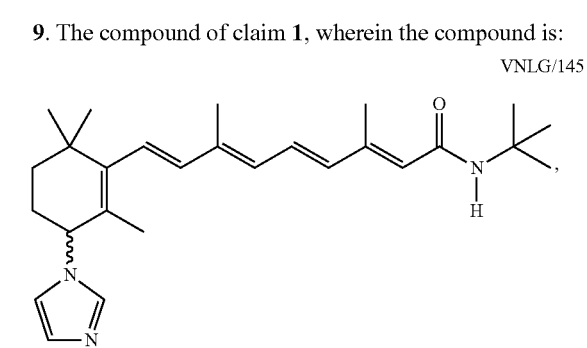
VNLG/145

-continued

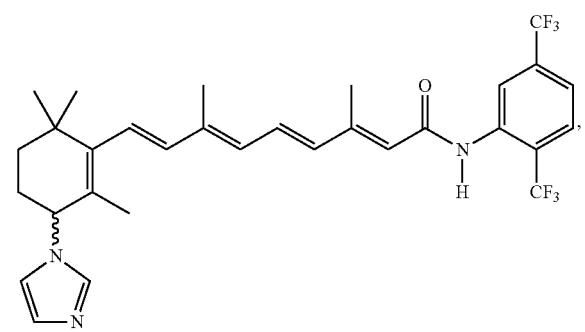
VNLG/146

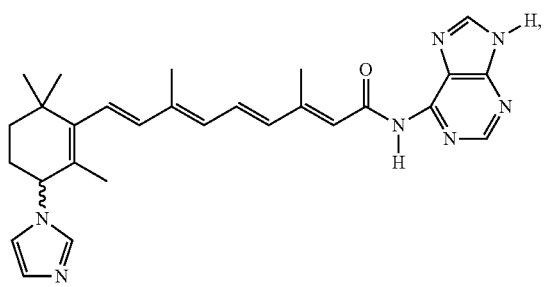
VNLG/147

VNLG/148

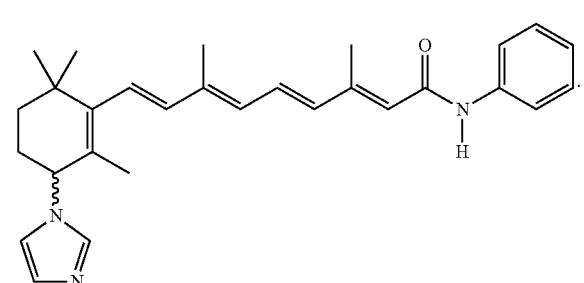
VNLG/152

VNLG/153

10. A pharmaceutical composition comprising at least one of the compounds of claim 1 and a pharmaceutically acceptable inactive ingredient.

11. A method of treating breast or prostate cancer in a subject in need thereof, comprising administering a therapeutically effective amount of at least one compound of structural formulae 2A, 3A, 3B, 4B, 4C or 5:

2A
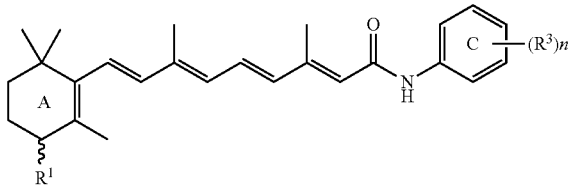

where $R^1$ is
- a thirane group,
- a —SH group,
- an -alkyl-SH group,
- —$OR^4$, where $R^4$ is hydrogen or alkyl,
- a cyclopropyl ether,
- an oxirane group formed together with the 4-position carbon,
- —$NR_5R_6$ where $R_5$ and $R_6$ are independently selected from the group consisting of hydrogen and alkyl groups, or $R_5$ and $R_6$ may together form an imidazolyl ring or a triazole ring,
- a pyridyl group, an ethinyl group, a cyclopropyl-amino group, a cyano group, an azido group, an allylic azole group, or an 1H-imidazole group, or
- $R^1$ forms, together with the C-4 carbon atom, an oxime, or aziridine group;

each $R^3$ is independent and is selected from a halogen group, a cyano group, a —SH group, and an alkyl group substituted with at least one of a halogen group, a cyano group, or a —SH group; and n is from 0 to 5;

3A
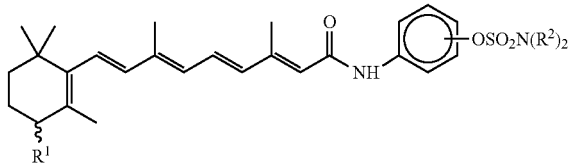

where $R^1$ is the same as in Formula 2A above;
each $R^2$ is independent and is a hydrogen or an alkyl group;

3B
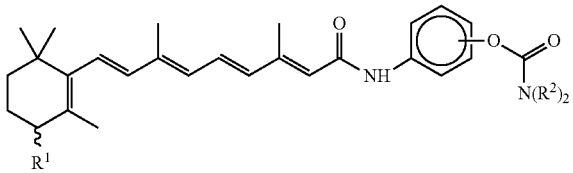

where $R^1$ and $R^2$ are the same as in Formula 3A above;

4B
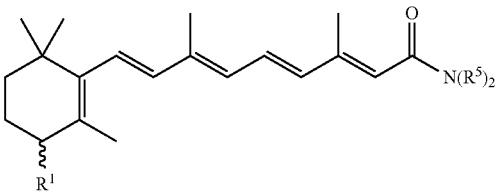

where $R^1$ is the same as in Formula 2A above, and
each $R^5$ is independently selected from a hydrogen atom, an alkyl group, and a ring containing a nitrogen atom; where the ring containing a nitrogen atom is selected from an azine ring, a triazine ring, an azirene ring, an azete ring, an diazetidine ring, an azole ring, a triazole ring, a tetrazole ring, an imidazole ring, an azocane ring, a pyridine ring, piperidine ring, benzimidazole ring, or a purine ring;

4C
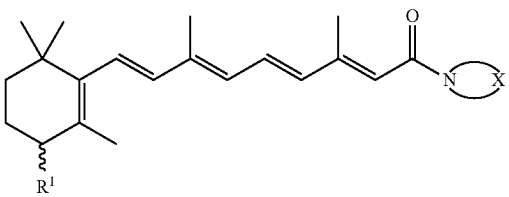

where $R^1$ is the same as in Formula 2A above, and X forms, together with the nitrogen atom, an azine ring, a triazine group, an azirine group, an azete group, an diazetidine group, an azocane group, a pyridine group, piperidine group, benzimidazole group, or a purine group;

Formula 5:

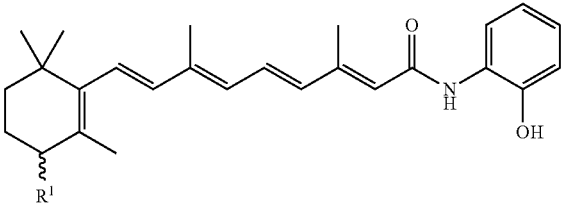

where $R^1$ is the same as in Formula 2A above.

12. The method of treating breast or prostate cancer in a subject in need thereof of claim 11 wherein the structural formula is formula 2A':

2A'
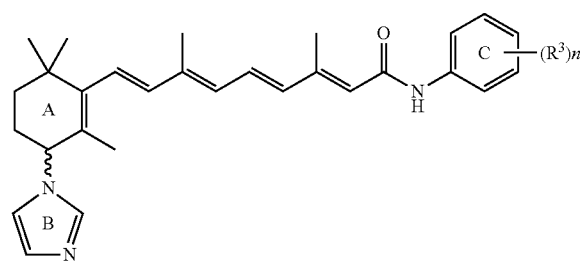

each $R^3$ and n are the same as in Formula 2A.

13. The method of treating breast or prostate cancer in a subject in need thereof of claim 12 wherein the structural formula is formula VNLG/146, VNLG/153, or one of Compounds 4-33:
VNLG/146
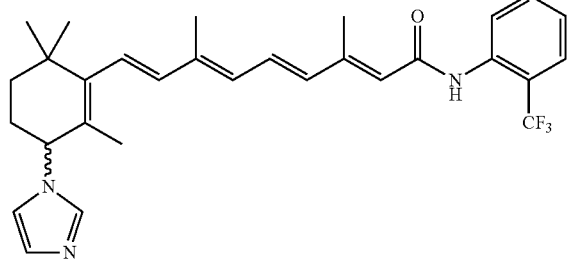
VNLG/153
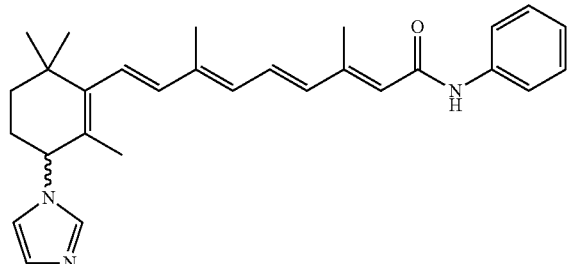
4
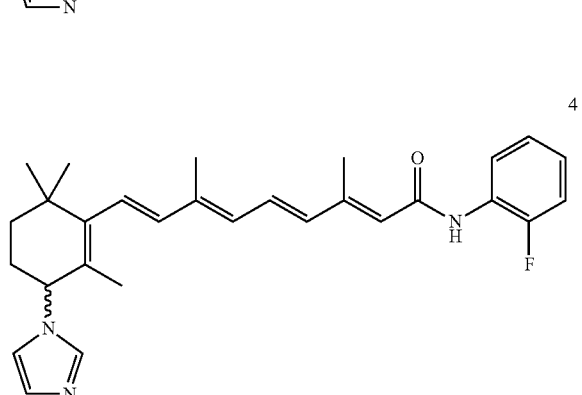
5
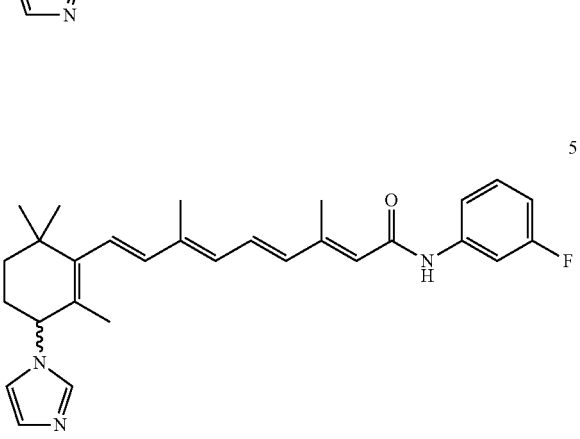
-continued
6
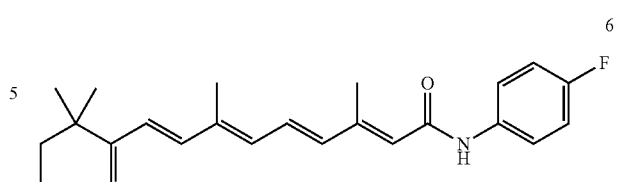
7
8
9
10

-continued
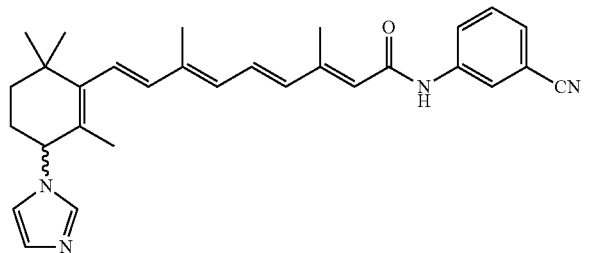
11
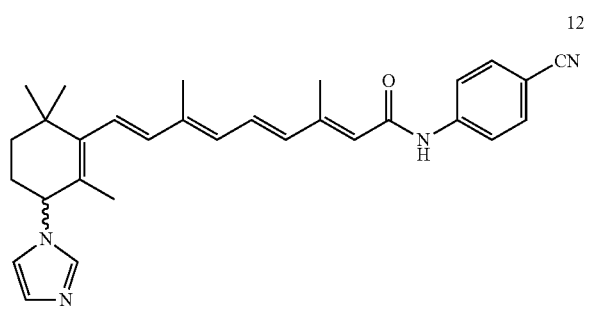
12
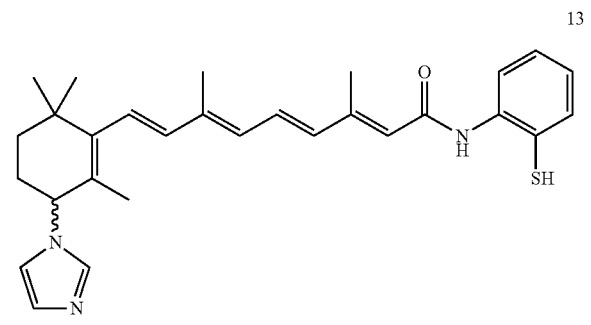
13
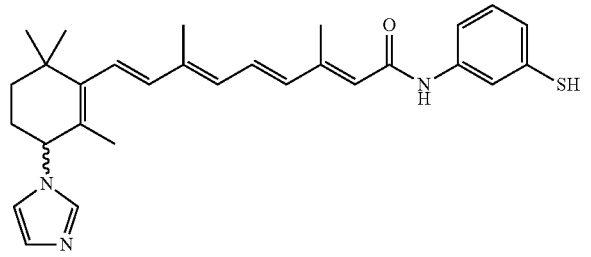
14
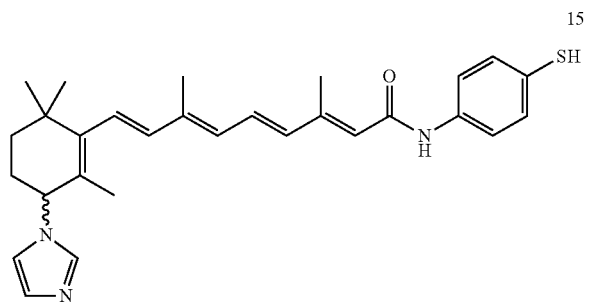
15
-continued
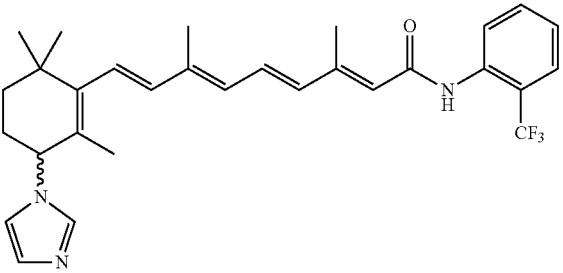
16

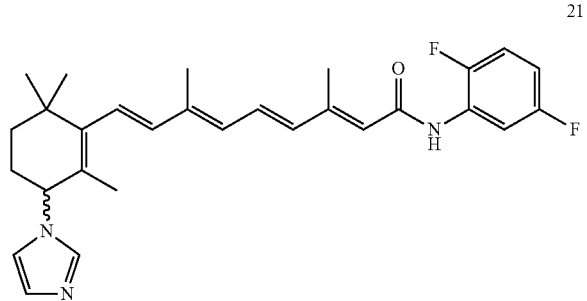
21
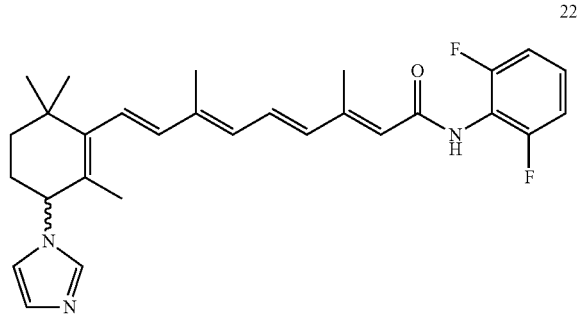
22
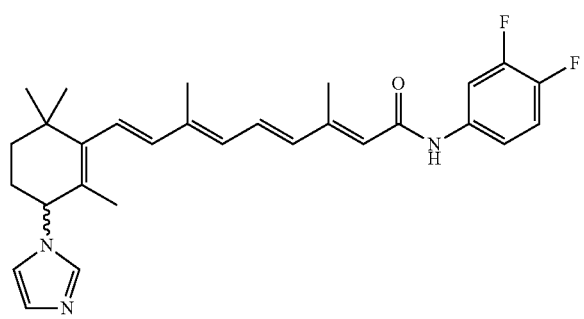
23
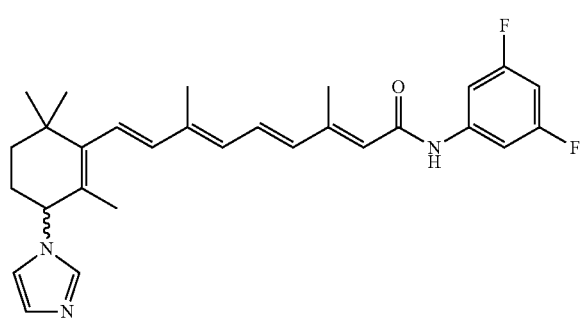
24
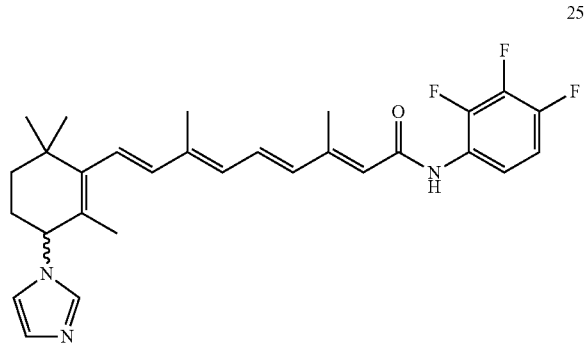
25
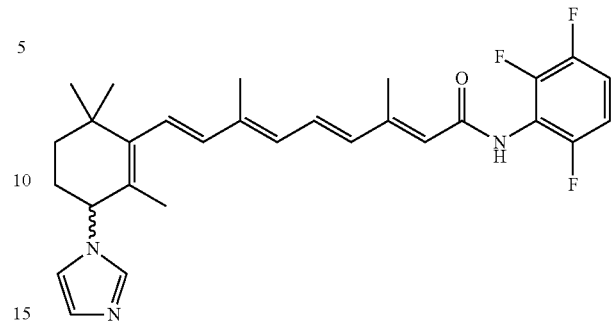
26
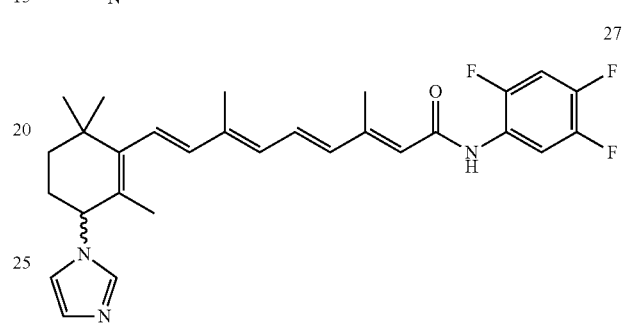
27
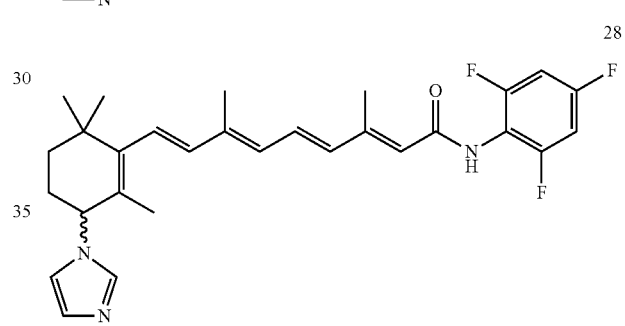
28
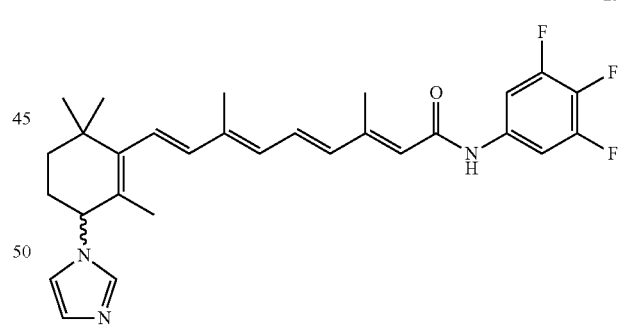
29
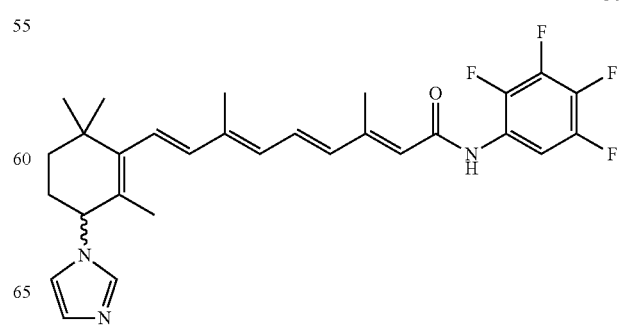
30

31

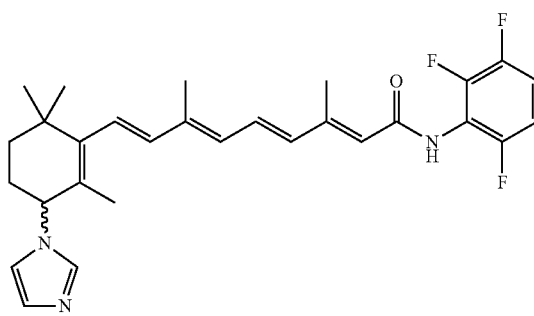

32

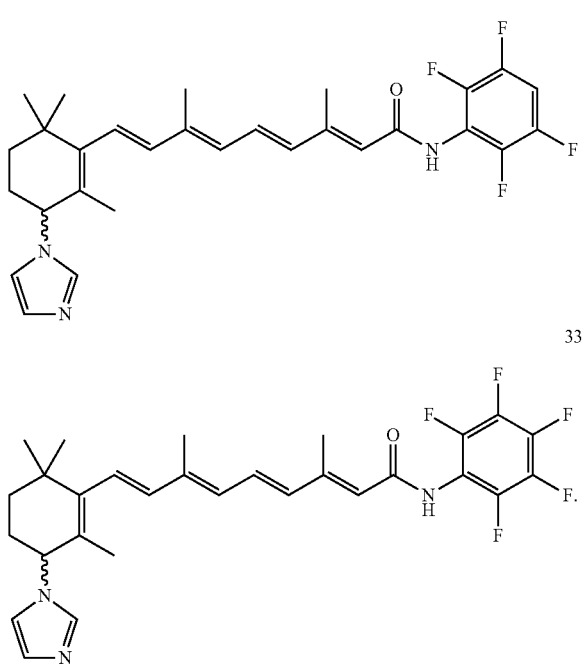

33

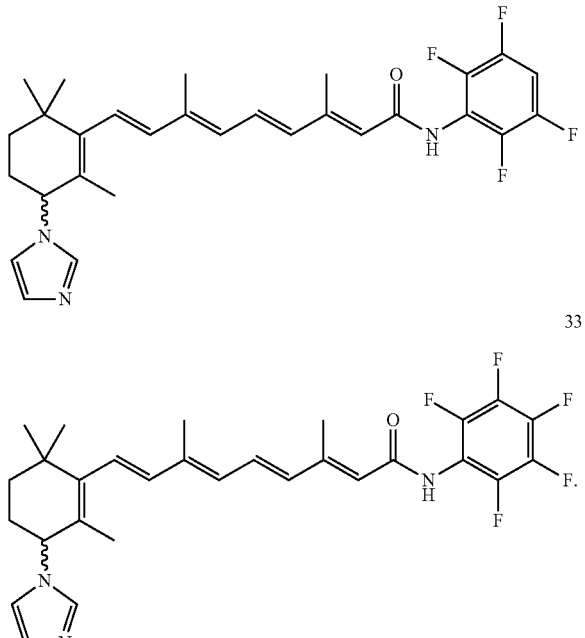

14. The method of treating breast or prostate cancer in a subject in need thereof of claim 11 wherein the structural formula is Formulae 3A', 3B', 3A" or 3B":

3A'

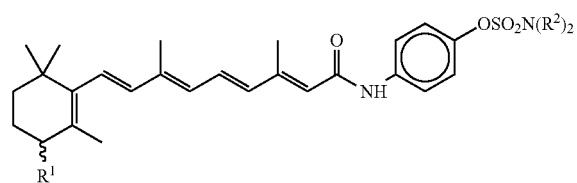

where R¹ and R² are the same as in Formula 3A;

3B'

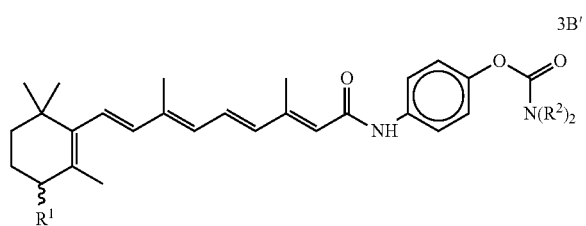

where R¹ and each R² are the same as in Formula 3A;

3A"

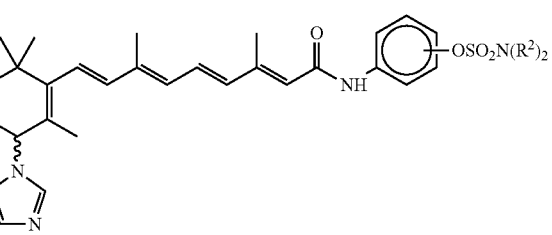

wherein each R² is independent and is the same as in Formula 3A;

3B"

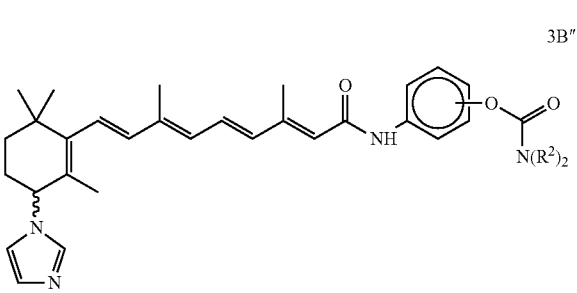

where each R² is independent and is the same as in Formula 3A.

15. The method of treating breast or prostate cancer in a subject in need thereof of claim 14 wherein the structural formula is Formula 34 or 35:

34

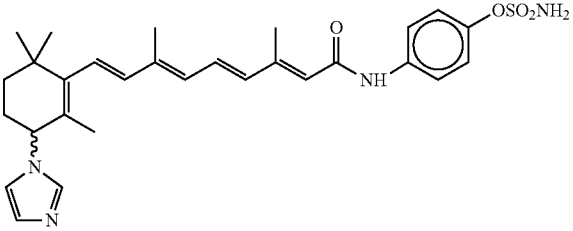

35

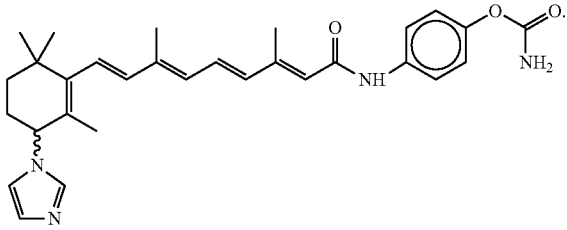

16. The method of treating breast or prostate cancer in a subject in need thereof of claim 11 wherein the structural formula is Formula 4A, 4B' or 4C':

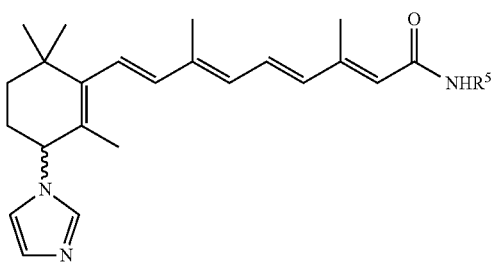
4A
where R⁵ is the same as in Formula 4B;
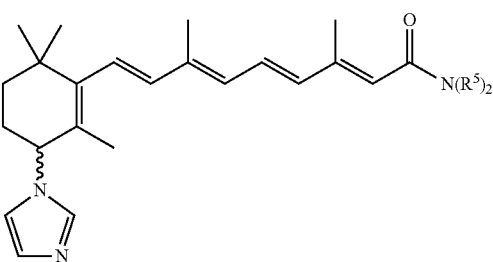
4B'
where each R⁵ is the same as in Formula 4B;
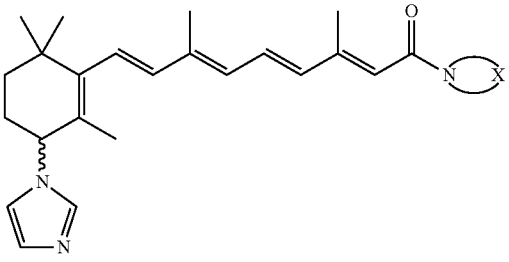
4C'
where X is the same as in Formula 4C.
17. A method of treating breast or prostate cancer in a subject in need thereof, comprising administering a therapeutically effective amount of at least one compound of structural formulae 36-38, 39 B-C, 40B-C, 41B-C, 42B-C, 43B-C, 44B-C, 45B, 45D, 46B-E, 47B-E, 48B-E, VNLG/145, VNLG/147 or VNLG/148:
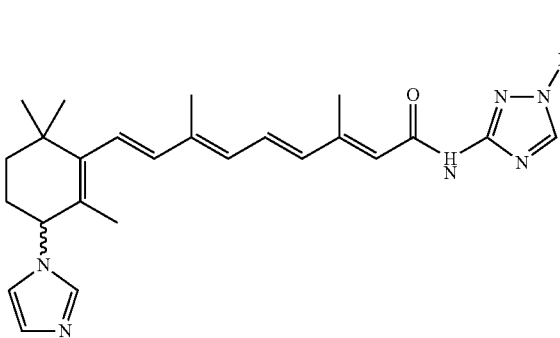
36
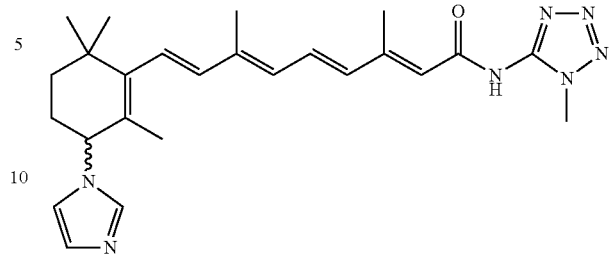
37
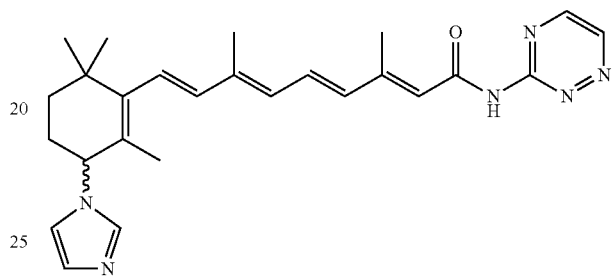
38
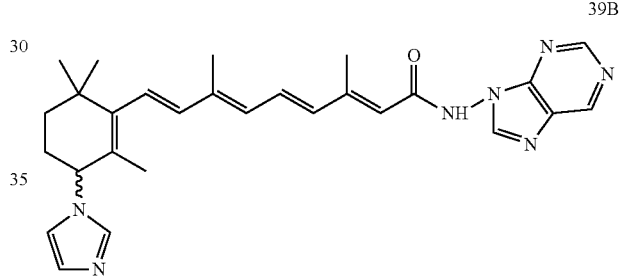
39B
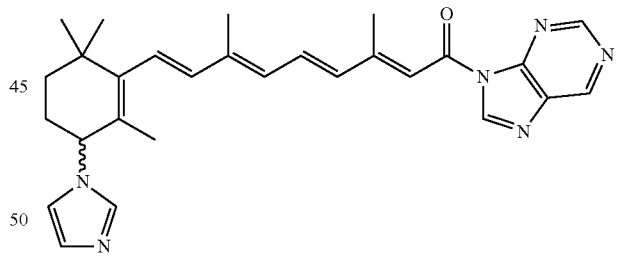
39C
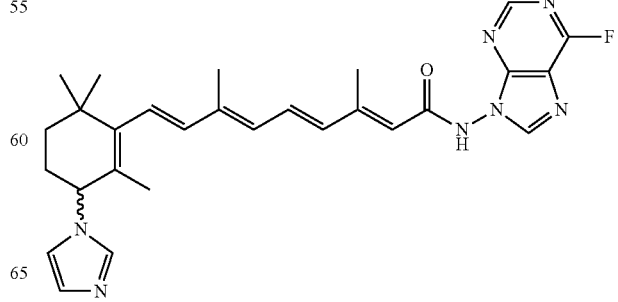
40B

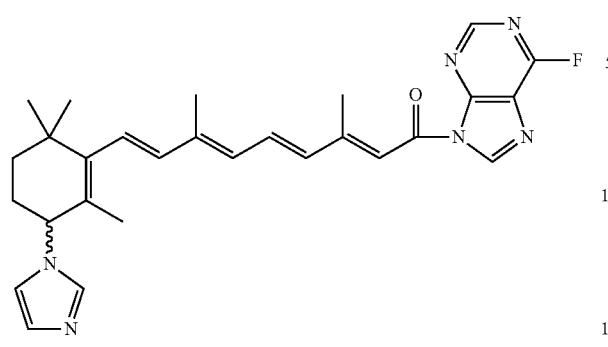
40C
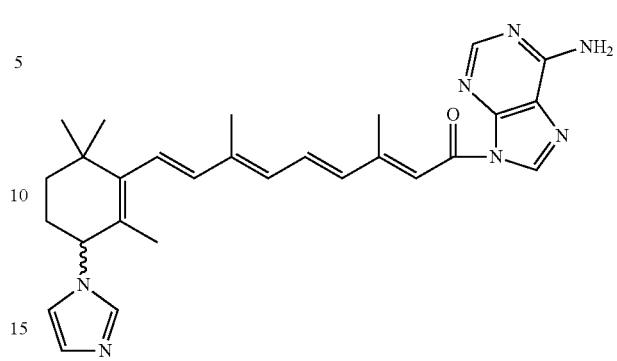
42C
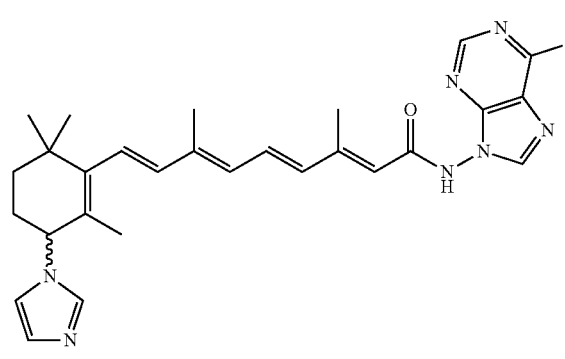
41B
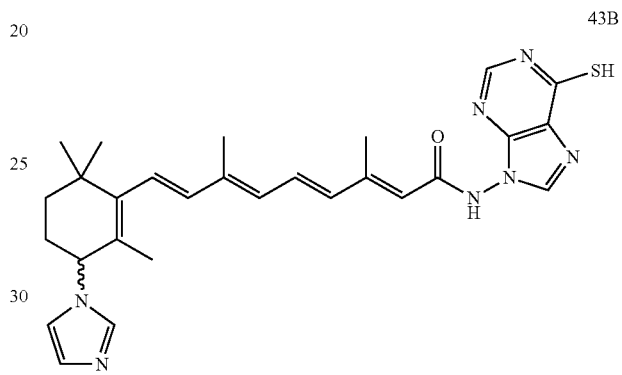
43B
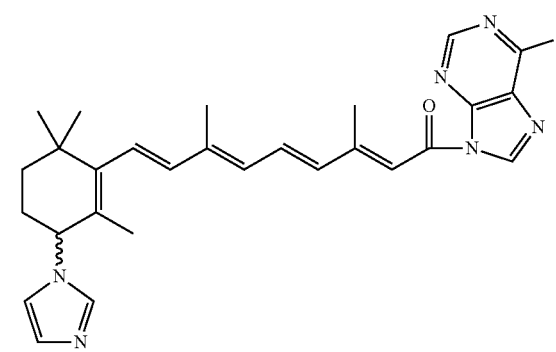
41C
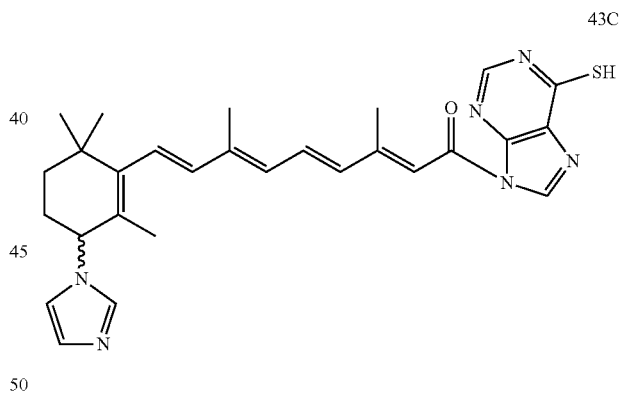
43C
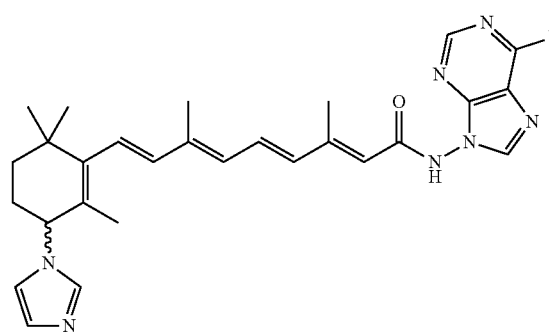
42B
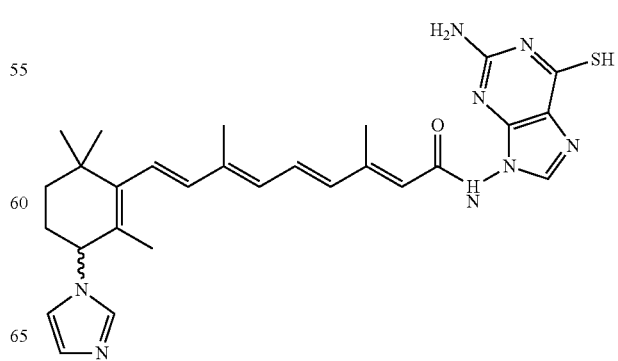
44B 44C
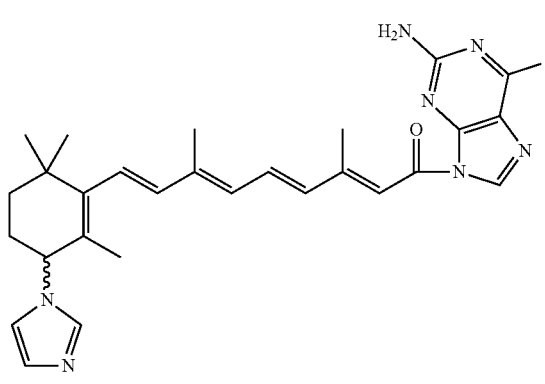
45B
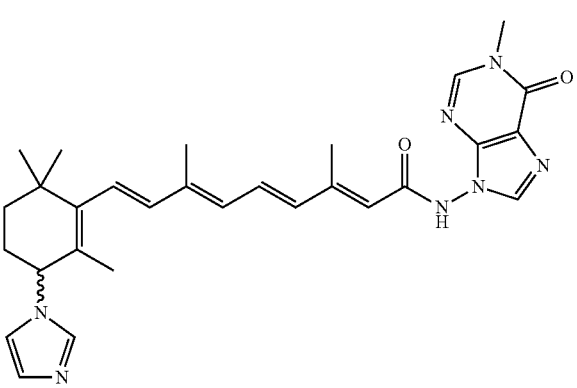
45D
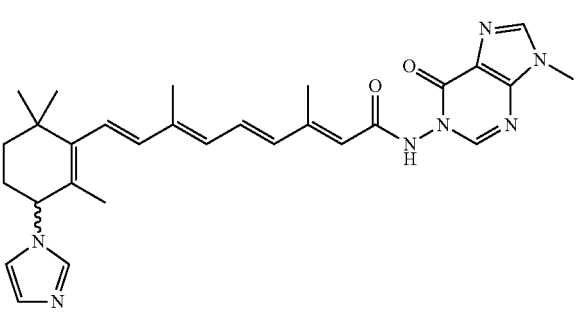
46B
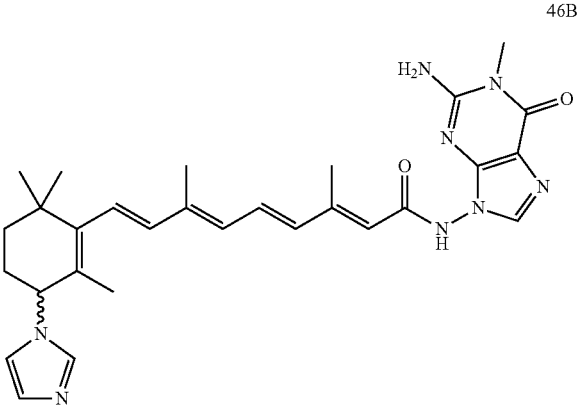
46C
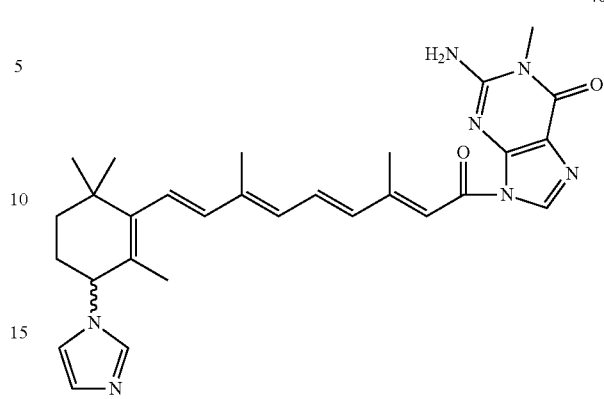
46D
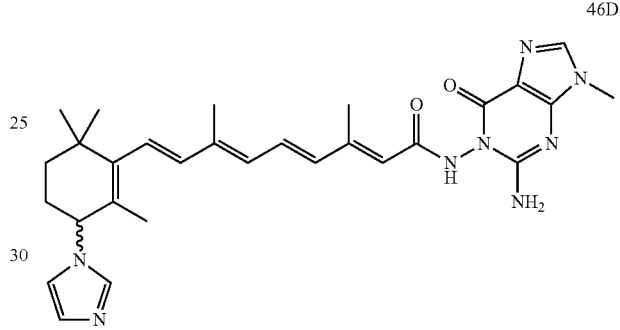
46E
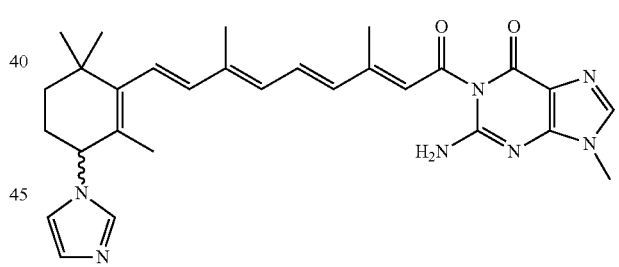
47B
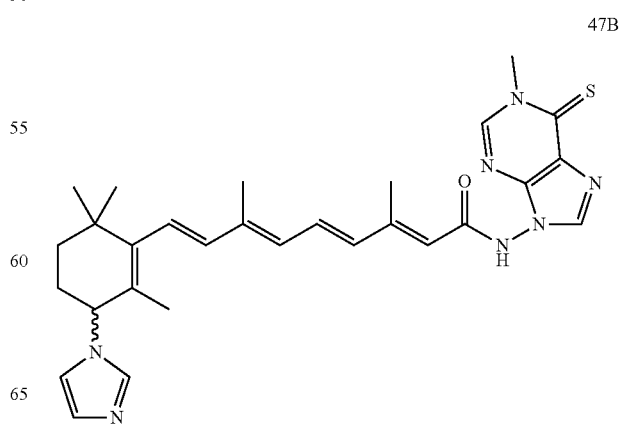

47C
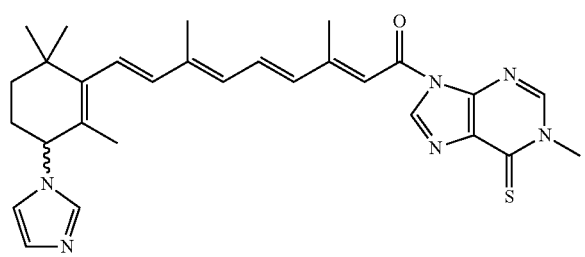
48D
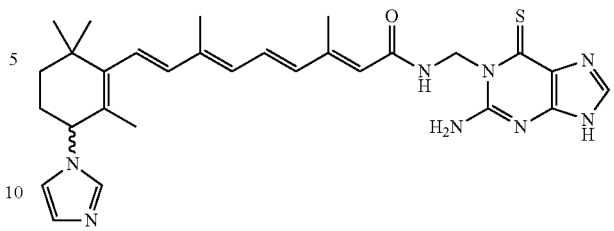
48B
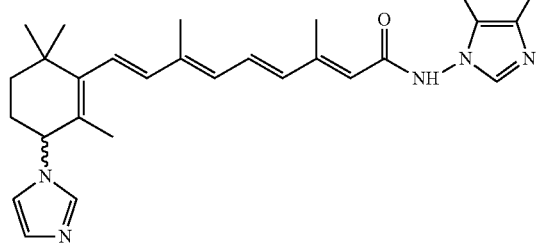
48E
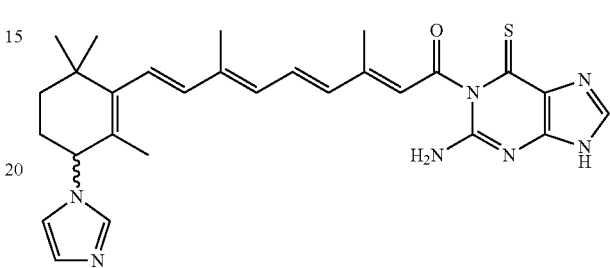
48C
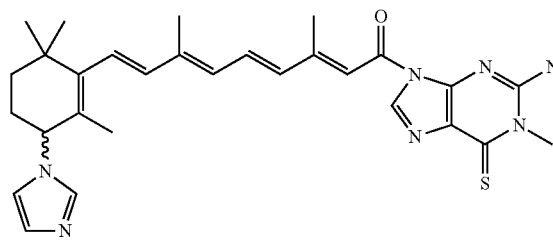
VNLG/145
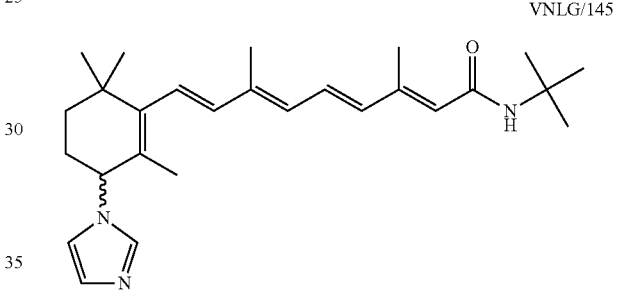
47D
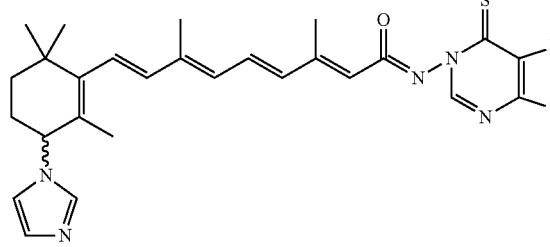
VNLG/147
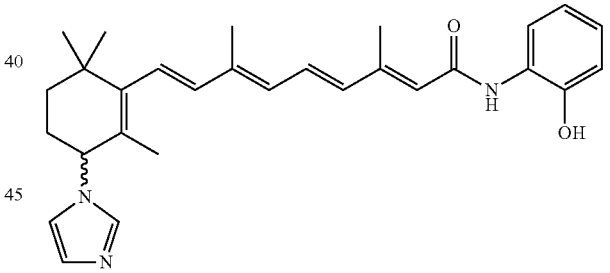
47E
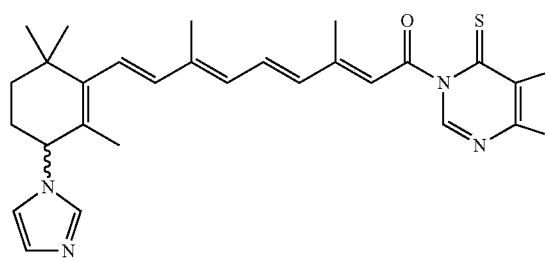
VNLG/148
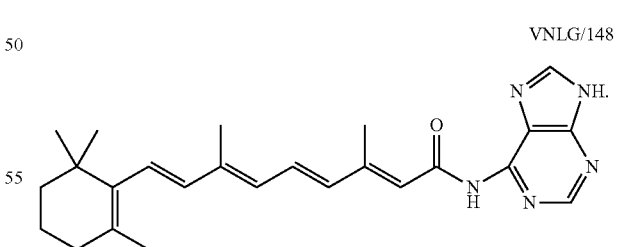
18. The method of treating breast or prostate cancer in a subject in need thereof of claim 11 wherein the structural formula is at least one selected from the group consisting of Formula VNLG/152, VNLG-153 and VNLG-146:

VNLG/152
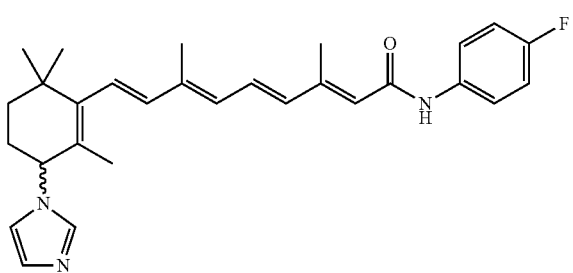
VNLG/153
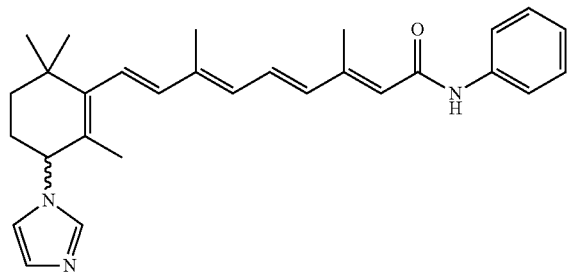
and
VNLG/146
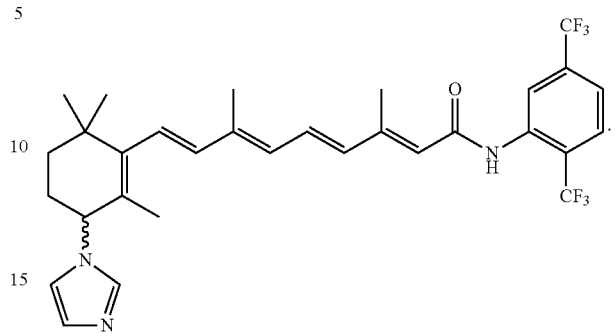
19. A method of treating breast or prostate cancer in a subject in need thereof, comprising administering a therapeutically effective amount of the pharmaceutical composition of claim 10.
* * * * *

UNITED STATES PATENT AND TRADEMARK OFFICE
CERTIFICATE OF CORRECTION

| | | |
|---|---|---|
| PATENT NO. | : 9,156,792 B2 | Page 1 of 1 |
| APPLICATION NO. | : 12/991822 | |
| DATED | : October 13, 2015 | |
| INVENTOR(S) | : Vincent Njar et al. | |

It is certified that error appears in the above-identified patent and that said Letters Patent is hereby corrected as shown below:

Specification

Column 1; Paragraph [0002] and the header above,
    Change

"This invention was made with government support under Grant Number CA117991 awarded by the National Institutes of Health and Grant Number W81XWH-04-1-0101 awarded by the Department of Defense. The U.S. government has certain rights in this invention."

To be:

--This invention was made with government support under Grant Number CA117991 awarded by the National Institutes of Health and Grant Number W81XWH-04-1-0101 awarded by the United States Army Medical Research and Material Command. The government has certain rights in the invention.--

Signed and Sealed this
First Day of March, 2016

Michelle K. Lee
*Director of the United States Patent and Trademark Office*